United States Patent
Lee et al.

(10) Patent No.: US 11,744,824 B2
(45) Date of Patent: Sep. 5, 2023

(54) 2-AMINO-3-CARBONYL IMIDAZOPYRIDINE AND PYRAZOLOPYRIDINE COMPOUNDS

(71) Applicant: 1ST Biotherapeutics, Inc., Gyeonggi-do (KR)

(72) Inventors: Jinhwa Lee, Gyeonggi-do (KR); Suyeon Jo, Gyeonggi-do (KR); Keonseung Lim, Gyeonggi-do (KR); A Yeong Park, Gyeonggi-do (KR); Gadhe Changdev Gorakshnath, Seoul (KR); Hwajung Nam, Busan (KR); Yeonguk Jeon, Gyeonggi-do (KR); Yejin Hwang, Gyeonggi-do (KR); Jae Eun Kim, Gyeonggi-do (KR); Misoon Kim, Gyeonggi-do (KR); Inyoung Yang, Seoul (KR)

(73) Assignee: 1ST Biotherapeutics, Inc., Gyeonggi-do (KR)

( * ) Notice: Subject to any disclaimer, the term of this patent is extended or adjusted under 35 U.S.C. 154(b) by 0 days.

(21) Appl. No.: 17/474,293

(22) Filed: Sep. 14, 2021

(65) Prior Publication Data
US 2022/0087985 A1  Mar. 24, 2022

Related U.S. Application Data

(60) Provisional application No. 63/078,372, filed on Sep. 15, 2020.

(51) Int. Cl.
| | |
|---|---|
| *C07D 471/04* | (2006.01) |
| *A61K 31/437* | (2006.01) |
| *C07D 519/00* | (2006.01) |
| *A61K 31/4709* | (2006.01) |
| *A61K 31/5377* | (2006.01) |
| *A61K 31/496* | (2006.01) |
| *A61K 31/506* | (2006.01) |
| *A61K 31/444* | (2006.01) |

(52) U.S. Cl.
CPC .......... *A61K 31/437* (2013.01); *A61K 31/444* (2013.01); *A61K 31/4709* (2013.01); *A61K 31/496* (2013.01); *A61K 31/506* (2013.01); *A61K 31/5377* (2013.01); *C07D 471/04* (2013.01); *C07D 519/00* (2013.01)

(58) Field of Classification Search
CPC .......................... C07D 471/04; A61K 31/437
USPC .................................................... 514/210.18
See application file for complete search history.

(56) References Cited

U.S. PATENT DOCUMENTS

| | | |
|---|---|---|
| 4,097,483 A | 6/1978 | Irikura |
| 2009/0318437 A1 | 12/2009 | Gaeta et al. |
| 2015/0158868 A1 | 6/2015 | Boyall et al. |

FOREIGN PATENT DOCUMENTS

| | | | |
|---|---|---|---|
| CN | 108084193 | * | 5/2018 |
| WO | WO-2006/114261 A1 | | 11/2006 |
| WO | WO-2012/102297 A1 | | 8/2012 |

OTHER PUBLICATIONS

International Search Report from corresponding PCT Application No. PCT/IB2021/058378, dated Dec. 17, 2021.
Arques, A. et al., "The reaction of 1-amino-4,6-diphenyl-2-methylthiopyridinium iodide with substituted acetonitriles", Synthesis, 1981, vol. 1981, No. 11, pp. 910-912.
Shestakov, A. S. et al., "Detailed studies of the alkylation sides of pyridin-2-yland 4,6-dimethylpyrimidin-2-yl-cyanamides", Journal of heterocyclic chemistry, 2017, vol. 54, No. 1, pp. 551-560.
Rauf, A. et al., "Synthesis, characterization, and urease inhibition of 5-substituted-8-methyl-2H-pyrido[1,2-a]pyrimidine-2,4(3H)-diones", Medicinal chemistry research, 2012, vol. 21, No. 1, pp. 60-74.

* cited by examiner

*Primary Examiner* — Niloofar Rahmani
(74) *Attorney, Agent, or Firm* — Harness, Dickey & Pierce, P.L.C.

(57) ABSTRACT

The present disclosure provides a compound of Formula (I) or pharmaceutically acceptable salt, stereoisomers thereof, a pharmaceutical composition comprising the compound, and a method for treating or preventing an inflammatory and autoimmune diseases, especially neuroinflammation diseases using the compound.

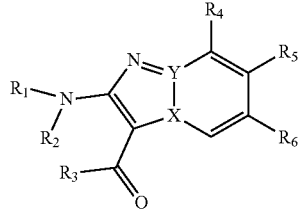

Formula I

22 Claims, No Drawings

2-AMINO-3-CARBONYL IMIDAZOPYRIDINE AND PYRAZOLOPYRIDINE COMPOUNDS

CROSS-REFERENCE TO RELATED APPLICATIONS

This application claims the benefit and priority to U.S. Provisional Patent Application No. 63/078,372, filed on 15 Sep. 2020. The entire disclosure of the application identified in this paragraph is incorporated herein by reference.

FIELD

The present disclosure generally relates to compounds having enzyme inhibitory activity, pharmaceutical compositions comprising the compound, and methods of using the compounds for treating diseases.

BACKGROUND

Receptor Interacting Protein Kinases (RIPKs) are a family of Ser/Thr and Tyr kinases with important roles in inflammation and innate immunity. The kinase activities of RIPK1 and RIPK3 were found to be critical for the activation of necroptotic cell death pathway by multiple stimuli, including TNFα family of cytokines, interferons (IFNs) and Toll-like receptor (TLR) ligands (Christofferson and Yuan, 2010; Vanlangenakker et al., 2012). Importantly, RIPK1/3 kinases have been implicated in a variety of pathologic settings that currently lack effective therapies, including stroke, myocardial infarction, retinal injuries, lethal Systemic Inflammatory Response Syndrome (SIRS) and chronic gut and skin inflammation, and acute pancreatitis (Linkermann and Green, 2014).

RIPK2 is another RIP kinase involved in the activation of NF-κB, mitogen-activated protein kinases (MAPKs) and apoptosis. The kinase activity of RIPK2 is dispensable for signaling via NF-κB and the MAPK JNK ('Jun N-terminal kinase') but is required for activation of the MAPK ERK2. The best-characterized function of RIPK2 is its mediation of signal transduction from the NOD ('nucleotide-binding oligomerization domain') proteins NOD1 and NOD2, which are cytosolic pathogen-recognition receptors that activate pro-inflammatory and antimicrobial responses in response to bacterial peptidoglycans in macrophages. NOD1 and NOD2 are homologous proteins composed of caspase recruitment domains (CARDs), nucleotide-binding domains and leucine-rich repeats. After recognition of its ligands, NOD1 or NOD2 recruits RIPK2 via CARD-CARD homotypic interactions. This process promotes the ubiquitination of RIPK2 and activation of the TAK1 and IKK complexes, which leads to the activation of NF-κB and MAPKs, as well as the production of pro-inflammatory cytokines by macrophages. RIPK2 also recruits various ubiquitin E3 ligases to the NOD2 complex, including XIAP ('X-chromosome-linked inhibitor of apoptosis'), cIAP1 and cIAP2, PELL3 and LUBAC. It has been demonstrated that XIAP deficiency causes impaired NOD1- or NOD2-mediated ubiquitination of RIPK2 and inflammatory signaling. XIAP is recruited to the NOD2-RIPK2 complex via binding to the kinase domain of RIPK2, which leads to K63-linked ubiquitination of RIPK2 and recruitment of LUBAC; this results in efficient activation of NF-κB and MAPKs, as well as cytokine production in macrophages. The ubiquitination sites of RIPK2 (Lys209, Lys410 and Lys538) are essential for its function in mediating signaling via NOD1 and NOD2. The D146N kinase-inactive mutant of RIPK2 retains the ability to bind XIAP and to activate NOD2 signaling, which suggests that the kinase activity of RIPK2 is not required for signaling via NOD1 and NOD2.

The NOD2-RIPK2 pathway has attracted special interest due to the role of this signaling node in granulomatous inflammatory diseases, including inflammatory bowel disease (IBD). Such pathologies can arise from either positive or negative dysregulation of the pathway (Caruso et al., 2014; Jostins et al., 2012; Philpott et al., 2014). Genetic variants in NOD2 are the strongest susceptibility factor to Crohn's disease (Hugot et al., 2001; Jostins et al., 2012; Ogura et al., 2001a). Crohn's disease-associated mutations that abrogate NOD2 binding to MDP may induce excessive inflammatory signaling from other pattern recognition receptors, including NOD1 (Couturier-Maillard et al., 2013; Inohara et al., 2003). In contrast, mutations in the second major Crohn's disease susceptibility factor, ATG16L1, disrupt an inhibitory interaction with NOD2 and consequently increase the activation of RIPK2 (Sorbara et al., 2013). Excessive RIPK2 activation has also been reported in pediatric Crohn's disease (Negroni et al., 2009). In addition, gain of function in the NOD2-RIPK2 pathway has been linked to Blau syndrome, early-onset sarcoidosis, allergic airway inflammation, and multiple sclerosis (Goh et al., 2013; Jun et al., 2013; Shaw et al., 2011). Overall, these data establish RIPK2 as a key molecule for the understanding of IBD pathogenesis as well as a potential therapeutic target in a wide spectrum of inflammatory and autoimmune diseases, including neuroinflammation diseases.

α-Synuclein is part of a large family of proteins including β- and γ-synuclein and synoretin. α-Synuclein is expressed in the normal state associated with synapses and is believed to play a role in neural plasticity, learning and memory. Several studies have implicated α-synuclein with a central role in Parkinson disease pathogenesis. Molecular changes in the α-synuclein protein that increase protein misfolding and aggregation have a direct role in disease pathogenesis. Aggregation of α-synuclein contributes to the formation of Lewy bodies and neutrites, the pathologic hallmarks of Parkinson disease and α-synucleinopathies. Activation of tyrosine kinase c-abl contributes to α-synuclein-induced neurodegeneration.

The tyrosine kinase c-abl is tightly regulated non-receptor protein tyrosine kinase involved in a wide range of cellular processes, including growth, survival and stress response (*Nat Rev Mol Cell Biol,* 2004, 5:33-44) and c-abl involved in regulation several cellular processes and has implicated in the development of the central nervous system by controlling neurogenesis. More recently, increasing evidence from various experimental model systems has also revealed that c-abl is activated in neurodegenerative disease such as Alzheimer's disease, Parkinson's disease, Neiman-Pick type C diseases and tauopathies (*Human Molecular Genetics,* 2014, Vol. 23, No. 11).

The stress-signaling non-receptor tyrosine kinase c-abl links parkin to sporadic forms of Parkinson's disease via tyrosine phosphorylation. Tyrosine phosphorylation of parkin by c-abl is a major post-translational modification that leads to loss of parkin function and disease progression in sporadic Parkinson disease. Inhibition of c-abl offers new therapeutic opportunities for blocking Parkinson disease progression (*The Journal of Neuroscience,* 2011, 31(1):157-163). Amyotrophic lateral sclerosis (ALS) is a fatal neurodegenerative disease characterized by progressive death of motor neurons. Knockdown of c-abl with small interfering RNAs (siRNAs) also rescued ALS motor neuron degeneration (Imamura et al., *Sci. Transl. Med.* 9, 2017). Multiple System Atrophy (MSA) is a rare, rapidly progressive neurodegenerative disease without any current treatment. In MSA there is accumulation of α-synuclein in the neurons and oligodendrocytes of the substantia nigra, striatum, olivopontocerebellar structures and spinal cord (*J Neural Transm* Vienna Austria 1996. 2016; 123(6)).

Administration of the tyrosine kinase inhibitor nilotinib decreases c-abl activity and ameliorates autophagic clearance of α-synuclein in transgenic and lentiviral gene transfer models. Activation of c-abl in the mouse forebrain induces neurodegeneration in the hippocampus and striatum. Therefore, an increase in c-abl activity via phosphorylation may be associated with the α-synuclein pathology detected in Parkinson disease and other neurodegenerative disease. (*Hum Mol Genet.* 2013 Aug. 15). c-Abl is a potential therapeutic target for α-synucleinopathy, Parkinson disease, Alzheimer disease, ALS, Dementia with Lewy body and MSA.

SUMMARY

The present disclosure provides a compound having RIPK2 and c-abl kinase inhibitory activity, a composition comprising the compound and a method useful to treat an inflammatory and/or autoimmune disease, especially neuroinflammation disease. In an embodiment, the compound is a compound of Formula (I):

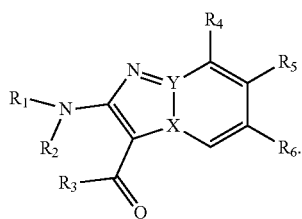

Formula I

In another embodiment, the present disclosure provides pharmaceutical compositions comprising a therapeutically effective amount of a compound described herein and a pharmaceutically acceptable carrier.

In yet another embodiment, the present disclosure provides methods of inhibiting or treating a neurodegenerative disease comprising administering to a subject in need thereof a therapeutically effective amount of one or more compounds described herein.

DETAILED DESCRIPTION

The following description is merely exemplary in nature and is not intended to limit the present disclosure, application, or uses.

Definitions

The generic terms used in the present disclosure are herein defined for clarity.

This specification uses the terms "substituent", "radical", "group", "moiety", and "fragment" interchangeably.

As used herein, the term "alkenyl" refers to a straight or branched hydrocarbonyl group with at least one site of unsaturation, i.e., a carbon-carbon, sp2 double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

As used herein, the term "alkoxy" is RO— where R is alkyl. Non-limiting examples of alkoxy groups include methoxy, ethoxy and propoxy.

As used herein, the term "alkoxyalkyl" refers to an alkyl moiety substituted with an alkoxy group. Examples of alkoxyalkyl groups include methoxymethyl, methoxyethyl, methoxypropyl and ethoxyethyl.

As used herein, the term "alkoxycarbonyl" is ROC(O)—, where R is an alkyl group as defined herein. In various embodiments, R is a $C_1$-$C_{10}$ alkyl group or a $C_1$-$C_6$ alkyl group.

As used herein, the term "alkyl" refers to a straight or branched chain hydrocarbonyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl. "Lower alkyl" means alkyl having from 1 to 4 carbon atoms.

As used herein, if the term "$C_1$-$C_6$" is used, it means the number of carbon atoms is from 1 to 6. For example, $C_1$-$C_6$ alkyl means an alkyl which carbon number is any integer of from 1 to 6.

As used herein, the term "alkylamino" refers to an amino group substituted with one or more alkyl groups. "N-(alkyl) amino" is RNH— and "N,N-(alkyl)$_2$amino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamino.

As used herein, the term "alkylaminoalkyl" refers to an alkyl moiety substituted with an alkylamino group, wherein alkylamino is as defined herein. Examples of alkylaminoalkyl groups include methylaminomethyl and ethylaminomethyl.

As used herein, the term "alkynyl" refers to a straight or branched carbon-chain group with at least one site of unsaturation, i.e., a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—$CH_2$C≡CH).

As used herein, the term "aryl" refers to any monocyclic or bicyclic carbon ring of up to 7 atoms in each ring, wherein at least one ring is aromatic, or an aromatic ring system of 5 to 14 carbon atoms which includes a carbocyclic aromatic group fused with a 5- or 6-membered cycloalkyl group. Representative examples of aryl groups include, but are not limited to, phenyl, tolyl, xylyl, naphthyl, tetrahydronaphthyl, anthracenyl, fluorenyl, indenyl, azulenyl and indanyl. A carbocyclic aromatic group can be unsubstituted or optionally substituted.

As used herein, the term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl. "Cycloalkyloxy" is RO—, where R is cycloalkyl.

As used herein, the terms "halogen" and "halo" refers to chloro (—Cl), bromo (—Br), fluoro (—F) or iodo (—I).

"Haloalkoxy" refers to an alkoxy group substituted with one or more halo groups and examples of haloalkoxy groups include, but are not limited to, —OCF$_3$, —OCHF$_2$ and —OCH$_2$F. "Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl. "Haloalkyl" refers to an alkyl moiety substituted with one or more halo groups. Examples of haloalkyl groups include —CF$_3$ and —CHF$_2$.

As used herein, the term "heteroalkyl" refers to a straight- or branched-chain alkyl group having from 2 to 14 carbons (in some embodiments, 2 to 10 carbons) in the chain, one or more of which has been replaced by a heteroatom selected from S, O, P and N. Exemplary heteroalkyls include alkyl ethers, secondary and tertiary alkyl amines, amides, alkyl sulfides, and the like.

As used herein, the term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments, the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. "Heterocyclyloxy" is RO—, where R is heterocyclyl. "Heterocyclylthio" is RS—, where R is heterocyclyl.

As used herein, the term "3- or 4-membered heterocyclyl" refers to a monocyclic ring having 3 or 4 ring atoms wherein at least one ring atom is heteroatom selected from the group consisting of N, O and S. Non-limiting examples of 3- or 4-membered heterocyclyl include aziridinyl, 2H-azirinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

As used herein, the term "heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl. "Heteroaryloxy" is RO—, where R is heteroaryl.

As used herein, the term "hydroxyalkoxy" refers to an alkoxy group substituted with a hydroxyl group (—OH), wherein alkoxy is as defined herein. An example of hydroxyalkoxy is hydroxyethoxy.

As used herein, the term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

As used herein, the term "pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

As used herein, the term "pharmaceutically acceptable carrier" refers to a diluent, adjuvant, excipient, or carrier, or other ingredient which is pharmaceutically acceptable and with which a compound of the invention is administered.

As used herein, the term "pharmaceutically acceptable salt" refers to a salt which may enhance desired pharmacological activity. Examples of pharmaceutically acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentane-propionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

As used herein, the term "substituted" means any of above groups (i.e., alkyl, aryl, heteroaryl, heterocycle or cycloalkyl) wherein at least one hydrogen atom of the moiety being substituted is replaced with a substituent. In one embodiment, each carbon atom of the group being substituted is substituted with no more than two substituents. In another embodiment, each carbon atom of the group being substituted is substituted with no more than one substituent. In the case of a keto substituent, two hydrogen atoms are replaced with an oxygen which is attached to the carbon via a double bond. Unless specifically defined, substituents include halogen, hydroxyl, (lower) alkyl, haloalkyl, mono- or di-alkylamino, aryl, heterocycle, —NO$_2$, B(OH)$_2$, BPin, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —NR$_a$SO$_2$R$_b$, —PO$_3$R$_a$, —PO(OR$_a$)(OR$_b$), —SO$_2$R$_a$, —S(O)R$_a$, —SO(N)R$_a$ (e.g., sulfoximine), —(R$_a$)S=NR$_b$ (e.g., sulfilimine) and —SR$_a$, wherein R$_a$ and R$_b$ are the same or different and independently hydrogen, halogen, amino, alkyl, haloalkyl, aryl or heterocycle, or wherein R$_a$ and R$_b$ taken together with the nitrogen atom to which they are attached form a heterocycle. R$_a$ and R$_b$ may be in the plural based on atoms which those are attached to.

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

In another embodiment, the compounds of Formula (I) are used for modulating the activity of a RIPK2 protein.

As used herein, the term "modulating" or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

The three main classes that pharmacological inhibitors of kinase activity are categorized by are (1) Type I, or "DFG-in" ATP competitive inhibitors, which directly compete with ATP in the ATP binding site (i.e., dual SRC ABL inhibitor dasatinib, (2) Type II, or "DFG-out" ATP competitive inhibitors, which, in addition to binding the ATP binding site also engage an adjacent hydrophobic binding site that is only accessible when the kinase is in an inactivated configuration (i.e., the activation loop is oriented in a conformation that would block substrate binding) (i.e., imatinib, nilotinib), and (3) non-ATP competitive inhibitors that bind at sites outside the ATP binding site that affect the activity of the kinase (i.e. GNF-2).

As used herein, the phrase "compound(s) of this/the disclosure" includes any compound(s) of Formula (I), as well as clathrates, hydrates, solvates, or polymorphs thereof. And, even if the term "compound(s) of the disclosure" does not mention its pharmaceutically acceptable sat, the term includes salts thereof. In one embodiment, the compounds of this disclosure include stereochemically pure compounds, e.g., those substantially free (e.g., greater than 85% ee, greater than 90% ee, greater than 95% ee, greater than 97% ee, or greater than 99% ee) of other stereoisomers. That is, if the compounds of Formula (I) according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

Compounds of the Present Disclosure

The present disclosure provides a compound of Formula (I):

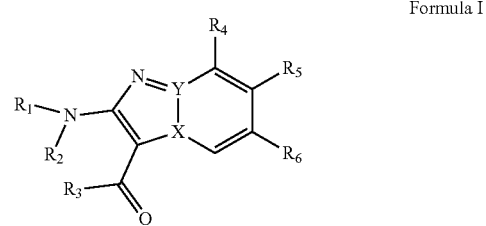

Formula I or a pharmaceutically acceptable salt thereof, wherein:

$R^1$ and $R^2$ are independently —H, $C_1$-$C_6$ alkyl, $C_3$-$C_6$ carbocyclyl, $C_1$-$C_4$ alkanoyl (i.e., —(CO)$C_1$-$C_4$ alkyl), —(CO)$C_3$-$C_6$ carbocyclyl, aryl, or heteroaryl, wherein each carbon is optionally substituted with one or more groups selected from the group consisting of halo, alkyl, hydroxyalkyl, haloalkyl, and monoalkylaminoalkyl; or $R^1$ and $R^2$ together form a 5-member heterocycle;

$R^3$ is —H, alkyl, alkoxy, cycloalkyl, heterocyclyl, aryl, heteroaryl, —O-cycloalkyl, —O-heterocyclyl, —O-aryl, —O-heteroaryl, —$NR_c$-alkyl, —$NR_c$-cycloalkyl, —$NR_c$-heterocyclyl, —$NR_c$-aryl, —$NR_c$-heteroaryl, —$NR_c$—$NR_c$ C(=O)$R_c$ or —$CF_3$, wherein each carbon is optionally substituted with one or more groups selected from the group consisting of halo, alkyl, hydroxyalkyl, haloalkyl, and monoalkylaminoalkyl;

$R^4$ and $R^5$ are independently —H, —OH, halo, $C_1$-$C_6$ alkyl, $C_1$-$C_6$ alkoxy, aryl, heteroaryl, heterocyclyl, or heteroalkyl, amino, —$SCH_3$, or —CN;

$R^6$ is selected from the group consisting of —H, halo, $C_1$-$C_6$ alkyl, $C_1$-$C_6$ alkoxy, $C_3$-$C_6$ carbocyclyl, heterocyclyl, aryl, heteroaryl, —$NR_c$-aryl, —$NR_c$-heteroaryl, —O-aryl, —O-heteroaryl, wherein $R^6$ is optionally substituted with one or more groups selected from the group consisting of halo, hydroxyl, alkyl, alkenyl, alkynyl, haloalkyl, hydroxyalkyl, aminoalkyl, trimethylsilylethoxymethyl, morpholinyl, piperazinyl, methylpiperazinyl, alkoxyalkenyl, —$NO_2$, —$NR_aR_b$, —$NR_aC(=O)R_b$, —$NR_aC(=O)NR_aR_b$, —$NR_aC(=O)OR_b$, —$OR_a$, —$SR_a$, —CN, —$C(=O)R_a$, —$C(=O)OR_a$, —$C(=O)NR_aR_b$, —$OC(=O)R_a$, —$OC(=O)OR_a$, and —$OC(=O)NR_aR_b$;

$R_a$ and $R_b$ are independently —H, halo, amino, alkyl, or haloalkyl;

$R_c$ is —H, $C_1$-$C_3$ alkyl, or cyclopropyl; and

X and Y are independently carbon or nitrogen, wherein X is N when Y is C, or X is C when Y is N.

In some embodiments, $R^3$ is selected from the group consisting of —H, methyl, isopropyl, butyl, methoxy, pyridinyl, phenyl, cyclopropyl, cyclobutyl, pyrazolyl, azetidinyl, pyrimidinyl, pyrrolidinyl, cyclopropylamino, and indazolyl, wherein $R^3$ is optionally substituted with one or more groups selected from the group consisting of halo, alkyl, hydroxyalkyl, haloalkyl, and monoalkylaminoalkyl. Non-limiting, representative compounds having such substitutions can be found in Table 1.

In some embodiments, $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoalkyl, alkylamino, trimethylsilylethoxymethyl, morpholinyl, piperazinyl, methylpiperazinyl, and alkoxyalkenyl. Non-limiting, representative compounds having such substitutions can be found in Table 1.

In one embodiment, the compound of Formula (I) is selected from compounds according to Formula (II) and pharmaceutically acceptable salts thereof:

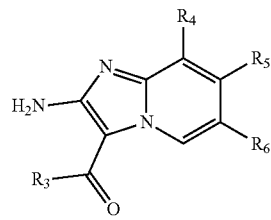

Formula II wherein $R^3$, $R^4$, $R^5$ and $R^6$ are as defined above.

In some embodiments, $R^3$ is fluorocyclopropyl and $R^6$ is indolyl which is optionally substituted with one or more groups selected from the group consisting of halo, hydroxyl, alkyl, haloalkyl, hydroxyalkyl, aminoalkyl, and tert-butoxycarbonyl. Non-limiting, representative compounds having such substitutions can be found in Table 1.

In some embodiments, $R^3$ is fluorocyclopropyl, and $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoalkyl, alkylamino, trimethylsilylethoxymethyl, morpholinyl, piperazinyl, methylpiperazinyl, and alkoxyalkenyl. Non-limiting, representative compounds having such substitutions can be found in Table 1.

In some embodiments, $R^3$ is cyclopropyl and $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoalkyl, alkylamino, trimethylsilylethoxymethyl, morpholinyl, piperazinyl, methylpiperazinyl, and alkoxyalkenyl. Non-limiting, representative compounds having such substitutions can be found in Table 1.

In some embodiments, $R^3$ is selected from the group consisting of methyl, isopropyl, butyl, methoxy, pyridinyl, phenyl, cyclobutyl, pyrazolyl, azetidinyl, pyrimidinyl, pyrrolidinyl, cyclopropylamino, and indazolyl, wherein $R^3$ is optionally substituted with one or more groups selected from the group consisting of halo, alkyl, hydroxyalkyl, haloalkyl, and monoalkylaminoalkyl. Non-limiting, representative compounds having such substitutions can be found in Table 1.

In another embodiment, the compound of Formula (I) is selected from compounds according to Formula (III) and pharmaceutically acceptable salts thereof:

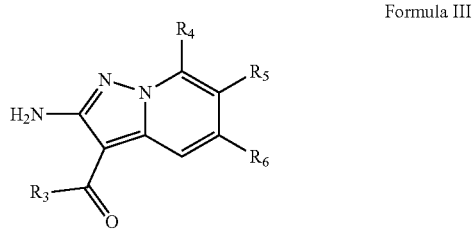

Formula III wherein $R^3$, $R^4$, $R^5$ and $R^6$ are as defined above. Non-limiting, representative compounds having such substitutions can be found in Table 1.

In some embodiments, the compounds of Formula I have $R^1$ and $R^2$ which are independently —H, alkyl, acetyl, tert-butoxycarbonyl, aminoethyl, dimethylaminoethyl, or methylaminoethyl; or $R^1$ and $R^2$ together forming a 5-member heterocyclic group. Non-limiting, representative compounds having such substitutions can be found in Table 1, wherein $R^3$ to $R^6$ are as defined above for Formula (I).

The present disclosure provides pharmaceutically acceptable salts of the compounds described above. The pharmaceutically acceptable salts are as defined above in the definition section. In some embodiments, the salt is hydrochloric acid salt, tartaric acid salt, phosphoric acid salt, or maleic acid salt.

Medical Uses and Methods of Treatment Using the Compounds According to the Present Disclosure The present disclosure further provides methods for treating a neurodegenerative disease or disorder in a subject having or susceptible to having such a disease or disorder, by administering to the subject a therapeutically effective amount of one or more compounds as described above. In one embodiment, the treatment is preventative treatment. In another embodiment, the treatment is palliative treatment. In another embodiment, the treatment is restorative treatment.

1. Diseases or Conditions

The compound of the present disclosure for inhibiting RIPK2 and c-abl activity is useful for treatment or prevention of a neurodegenerative disease or disorder. The compound can be used for inhibiting or hindering RIPK2 and c-abl kinase activity, and for treating a neurodegenerative disease or disorder, or for preventing aggravation of such disease. Thus, the present disclosure provides a method for inhibiting or hindering RIPK2 and c-abl activity in a cell, wherein the cell is contacted with an effective amount of a compound of the present disclosure. In one embodiment, such cell is present in a subject (for example, Alzheimer patients). In another embodiment, there is provided a medical use for treating or preventing an inflammatory and/or autoimmune disease, especially neuroinflammation diseases or disorder in a subject, using the compound according to the present disclosure. The method of the present disclosure comprises administering to a subject in need of treatment or prevention a pharmaceutical composition containing a therapeutically or prophylactically effective amount of RIPK2 and c-abl inhibitor. The inflammatory and autoimmune diseases, especially neuroinflammation diseases or disorder includes, but is not limited to, α-synucleinopathy, Parkinson's disease, dementia with Lewy body, multiple system atrophy (MSA), Alzheimer's disease or amyotrophic lateral sclerosis (ALS).

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development. In one embodiment, the suitable subject to be treated according to the present disclosure is human.

3. Administration and Dosing

The compounds of the present disclosure are generally administered in a therapeutically effective amount. The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release. Most parenteral formulations are aqueous solutions containing excipients, including salts, buffering agents and isotonic agents. Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Transdermal Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical or transdermal administration can also be performed by electroporation, iontophoresis, phonophoresis and the like.

Compositions for topical administration may be formulated as immediate or modified release, including delayed or sustained release.

Combination Therapy

A pharmaceutical composition according to the present disclosure may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by RIPKs and c-abl kinase. Examples of such active ingredients are, without limitation, agents to treat inflammatory and autoimmune diseases or disorder.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* (7th ed.), *Remington: The Science and Practice of Pharmacy* (20th ed.), *Encyclopedia of Pharmaceutical Technology* (3rd ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

The present disclosure provides a compound having various pharmacological effects by inhibiting RIPK2 and c-abl activity, a pharmaceutical composition having the compound as an effective agent, a medical use, particularly for treating a neurodegenerative disease or disorder, of the compound, and a method of treatment or prevention comprising administering the compound to a subject in need of such treatment or prevention. The compounds of the present disclosure and pharmaceutically acceptable salts thereof have good safety and high selectivity for RIPK2 and c-abl, and thus exhibit superior property as a drug.

DETAILED DESCRIPTION

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all of its material advantages.

Synthesis of Formula (I) Compounds

Synthetic methods from A to S were used to prepare the compounds of the following. Below, the illustrating synthetic examples of some compounds of the present disclosure are described, and other compounds can be prepared by the similar method to the one described below with different starting or reacting materials.

Synthetic Method A

Example 1. (2-amino-6-bromoimidazo[1,2-a]pyridin-3-yl)(cyclopropyl)methanone

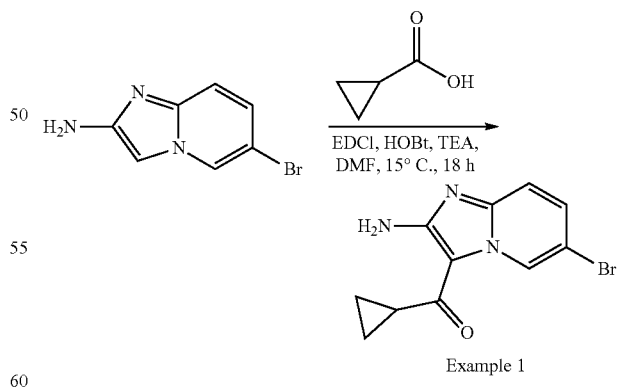

Example 1

To a solution of cyclopropanecarboxylic acid (3.17 g, 36.78 mmol, 2.91 mL, 1.3 eq) in DMF (50 mL) was added EDCI (6.51 g, 33.95 mmol, 1.2 eq), HOBt (4.59 g, 33.95 mmol, 1.2 eq) and TEA (8.59 g, 84.89 mmol, 11.82 mL, 3 eq). The mixture was stirred at 15° C. for 1 hr. then added 6-bromoimidazo[1,2-a]pyridin-2-amine (6 g, 28.30 mmol, 1 eq). The final mixture was stirred at 15° C. for 18 hr. The mixture was poured into water (200 mL) and extracted with ethyl acetate (300 mL*3), the organic phase was washed with brine (500 mL*2) and dried with anhydrous sodium sulfate (Na$_2$SO$_4$), filtered and concentrated in vacuum. The residue was purified by trituration with ethyl acetate (50 mL), filtered and the filter cake was concentrated. Example 1 (2.4 g, 8.25 mmol, 30.28% yield, 96.3% purity) was obtained as yellow solid.

$^1$H NMR (400 MHz, DMSO-d$_6$) δ 9.70 (d, J=1.2 Hz, 1H), 7.60 (dd, J=2.1, 9.3 Hz, 1H), 7.32 (d, J=9.3 Hz, 1H), 6.62 (s, 2H), 2.46-2.37 (m, 1H), 1.02-0.90 (m, 4H); LCMS (electrospray) m/z 282.10 (M+2H)+.

Synthetic Method B

Example 6. 1-(2-amino-6-(3-fluoro-2-methylphenyl) imidazo[1,2-a]pyridin-3-yl)ethan-1-one

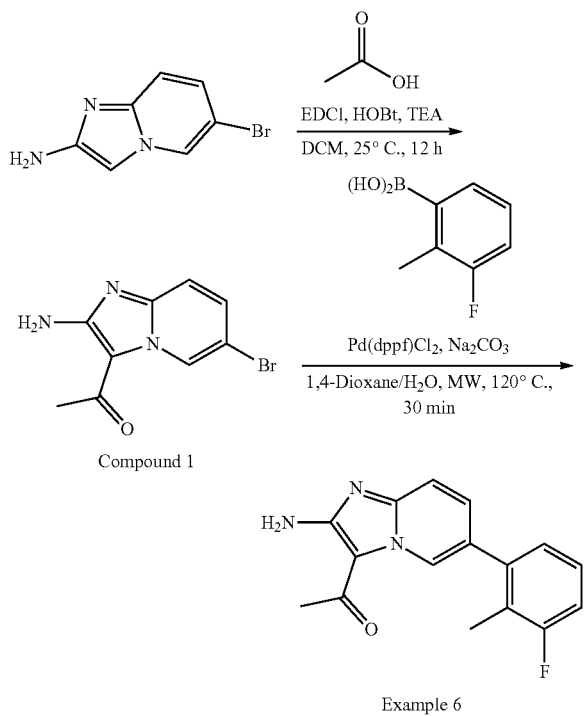

Step 1) 1-(2-amino-6-bromoimidazo[1,2-a]pyridin-3-yl)ethan-1-one

To a solution of 6-bromoimidazo[1,2-a]pyridin-2-amine (260 mg, 1.23 mmol, 1 eq) in DCM (20 mL) were added EDCI (358 mg, 1.84 mmol, 1.5 eq), HOBt (249 mg, 1.84 mmol, 1.5 eq), TEA (186 mg, 1.84 mmol, 256 μL, 1.5 eq), the mixture was stirred at 25° C. for 1 hr, then acetic acid (81 mg, 1.35 mmol, 1.1 eq) was added. The mixture was stirred at 25° C. for 12 hr. The reaction mixture was concentrated under reduced pressure to remove DCM solution to give a residue. The crude product was purified by silica gel chromatography (product came out at hexane/ethyl acetate=1/2) to afford Compound 1 (177 mg, 0.67 mmol, 57% yield) as a white solid.

$^1$H NMR (400 MHz, DMSO-d$_6$) δ 9.66 (s, 1H), 7.61 (dd, J=9.3, 2.2 Hz, 1H), 7.33 (d, J=9.3 Hz, 1H), 6.51 (s, 2H), 2.43 (s, 3H).

Step 2) 1-(2-amino-6-(3-fluoro-2-methylphenyl) imidazo[1,2-a]pyridin-3-yl)ethan-1-one To a solution of Compound 1 (150 mg, 0.590 mmol, 1 eq) in dioxane (6 mL) and H$_2$O (2 mL) were added (3-fluoro-2-methylphenyl)boronic acid (136 mg, 0.883 mmol, 1.5 eq), Na$_2$CO$_3$ (125 mg, 1.179 mmol, 2.0 eq), Pd(dppf)Cl$_2$ (43 mg, 0.06 mmol, 0.1 eq) at the room temperature and then heated at 120° C. under the microwaves for 30 min, cooled down to the room temperature, filtered through a celite pad to remove solids, and partitioned between ethyl acetate and saturated aqueous sodium bicarbonate solution. The organic layer was washed with saturated aqueous sodium chloride solution, separated, dried over anhydrous Na$_2$SO$_4$, filtered, and concentrated in vacuo. The residue was purified by silica gel chromatography (hexane/ethyl acetate=1/1) to afford Example 6 (122 mg, 0.430 mmol, 73% yield) as an ivory solid.

$^1$H NMR (400 MHz, DMSO-d$_6$) δ 9.49 (s, 1H), 7.51 (dd, J=9.2, 1.8 Hz, 1H), 7.41 (d, J=8.2 Hz, 1H), 7.38-7.29 (m, 1H), 7.23 (t, J=8.5 Hz, 1H), 7.16 (d, J=7.1 Hz, 1H), 6.47 (s, 2H), 2.44 (s, 3H), 2.16 (d, J=2.2 Hz, 3H); LCMS (electrospray) m/z 284.10 (M+H)+.

Synthetic Method C

Example 24. (2-((2-(dimethylamino)ethyl)amino)-6-(3-fluoro-2-methylphenyl)imidazo[1,2-a]pyridin-3-yl)((1S,2S)-2-fluorocyclopropyl)methanone

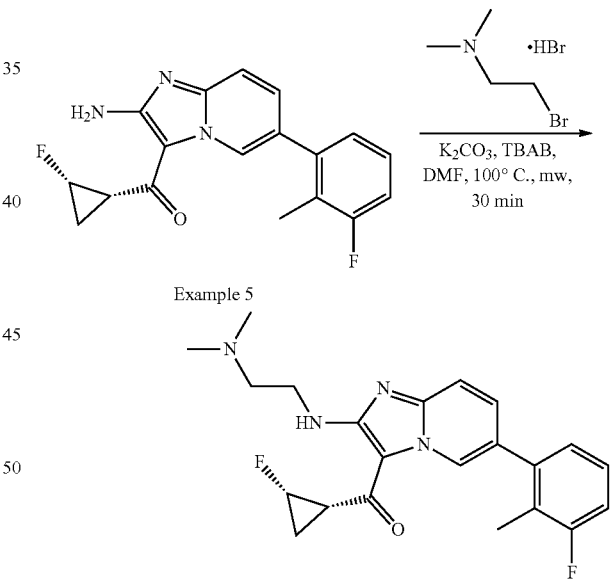

To a solution of Example 5 (100 mg, 0.30 mmol, 1 eq) in DMF (1.5 mL) were added 2-bromo-N,N-dimethylethan-1-amine·HBr (105 mg, 0.45 mmol, 1.5 eq), K$_2$CO$_3$ (124 mg, 0.90 mmol, 3 eq) and TBAB (9.6 mg, 0.03 mmol, 0.1 eq). The reaction mixture was heated to 100° C. under microwave for 30 min. The reaction mixture was diluted with water 10 mL and extracted with ethyl acetate (10 mL*2). The combined organic layers were washed with brine (10 mL), dried over Na$_2$SO$_4$, filtered and the filtrate was concentrated. The residue was purified by silica gel column chromatography (0 to 20% gradient MeOH in DCM) to obtain Example 24 (10 mg, 8.3% yield).

$^1$H NMR (400 MHz, DMSO-$d_6$) δ 9.77 (s, 1H), 8.22-8.09 (m, 2H), 7.44-7.40 (m, 1H), 7.35-7.28 (m, 1H), 7.24-7.12 (m, 1H), 5.37-5.16 (m, 1H), 4.54 (s, 2H), 4.09 (d, J=4.9 Hz, 2H), 3.17 (d, J=3.8 Hz, 6H), 2.83-2.66 (m, 4H), 2.33-2.08 (m, 3H), 1.96 (dtd, J=23.5, 6.8, 3.2 Hz, 1H), 1.33-1.23 (m, 1H); LCMS (electrospray) m/z 399.2 (M+H)+.

Synthetic Method D

Example 28. (2-amino-6-(5-methylthiazol-4-yl)imidazo[1,2-a]pyridin-3-yl)((1S,2S)-2-fluorocyclopropyl)methanone

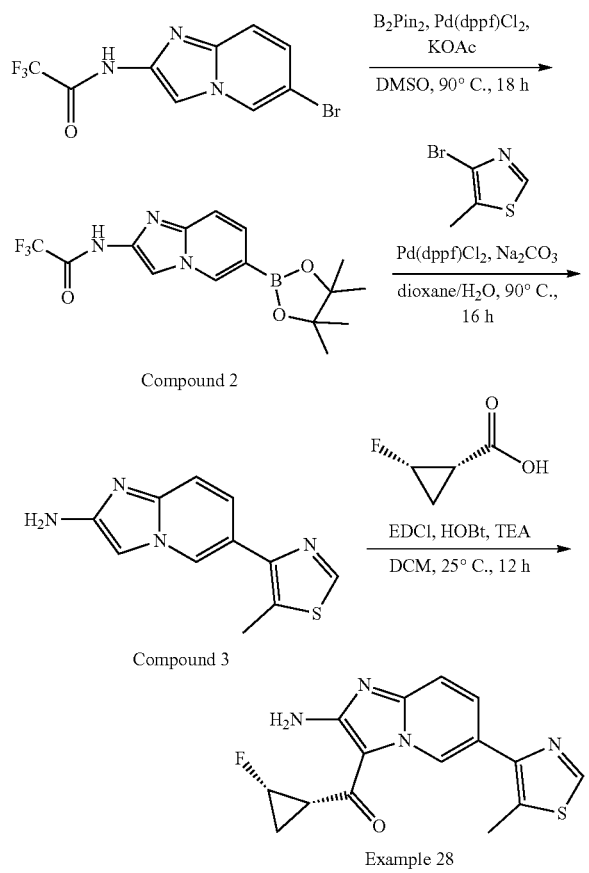

Step 1) 2,2,2-trifluoro-N-(6-(4,4,5,5-tetramethyl-1,3,2-dioxaborolan-2-yl)imidazo[1,2-a]pyridin-2-yl)acetamide To a solution of N-(6-bromoimidazo[1,2-a]pyridin-2-yl)-2,2,2-trifluoroacetamide (1.0 g, 3.24 mmol, 1 eq) in DMSO (30 mL) were added Bis(pinacolato)diboron (1.0 g, 4.21 mmol, 1.3 eq), Pd(dppf)Cl$_2$ (234 mg, 0.32 mmol, 0.1 eq), KOAc (953 mg, 9.72 mmol, 3 eq) at the room temperature and then heated at 90° C. for 7 hr, cooled down to the room temperature, filtered through a celite pad to remove solids, and partitioned between ethyl acetate and saturated aqueous sodium bicarbonate solution. The organic layer was washed with saturated aqueous sodium chloride solution, separated, dried over anhydrous MgSO$_4$, filtered, and concentrated in vacuo. The residue was purified by silica gel chromatography (hexane/ethyl acetate=1/2) to afford Compound 2 (602 mg, 1.69 mmol, 52.4% yield) as beige solid.

Step 2) 6-(5-methylthiazol-4-yl)imidazo[1,2-a]pyridin-2-amine

To a solution of 4-bromo-5-methylthiazole (200 mg, 1.12 mmol, 1 eq) in dioxane (4 mL) and H$_2$O (1 mL) were added Compound 2 (598.35 mg, 1.68 mmol, 1.5 eq), Na$_2$CO$_3$ (238.11 mg, 2.25 mmol, 2 eq), Pd(dppf)Cl$_2$ (82.19 mg, 112.33 μmol, 0.1 eq), then the mixture was stirred at 90° C. for 16 hours under N$_2$. The reaction mixture was concentrated under reduced pressure to remove H$_2$O and dioxane solution to give the residue. The residue was purified by reversed-phase flash chromatography (MeCN/H$_2$O, 0.05% TFA, 25%~30%) to give product. Compound 3 (80 mg, 347.39 μmol, 30.93% yield) was obtained as a yellow solid.

Step 3) (2-amino-6-(5-methylthiazol-4-yl)imidazo[1,2-a]pyridin-3-yl)((1S,2S)-2-fluorocyclopropyl)methanone To a solution of (1S,2S)-2-fluorocyclopropane-1-carboxylic acid (31.64 mg, 303.97 μmol, 1 eq) in DCM (2 mL) was added EDCI (69.93 mg, 364.76 μmol, 1.2 eq), HOBt (49.29 mg, 364.76 μmol, 1.2 eq), TEA (92.27 mg, 911.90 μmol, 126.92 μL, 3 eq), the mixture was stirred at 25° C. for 1 hr, then were added Compound 3 (70 mg, 303.97 μmol, 1 eq). The mixture was stirred at 25° C. for 11 hr. The reaction mixture was concentrated under reduced pressure to remove DCM solution to give a residue. The residue was purified by prep-HPLC (column: Waters Xbridge 150*25 mm*5 um; mobile phase: [water (0.05% ammonia hydroxide v/v)-ACN]; B %: 15%-45%, 10 min). Example 28 (53 mg, 167.53 μmol, 55.12% yield) was obtained as a white solid.

$^1$H NMR (400 MHz, DMSO-$d_6$) δ 10.01-9.88 (m, 1H), 8.99 (br d, J=0.9 Hz, 1H), 7.91-7.84 (m, 1H), 7.44 (br d, J=9.0 Hz, 1H), 6.68 (br s, 2H), 5.29-5.07 (m, 1H), 2.68-2.58 (m, 5H), 1.93-1.84 (m, 1H), 1.20-1.08 (m, 1H); LCMS (electrospray) m/z 317.20 (M+H)+.

Synthetic Method E

Example 33. N-(3-acetyl-6-(3-fluoro-2-methylphenyl)imidazo[1,2-a]pyridin-2-yl)acetamide and Example 37. N-acetyl-N-(3-acetyl-6-(3-fluoro-2-methylphenyl)imidazo[1,2-a]pyridin-2-yl)acetamide

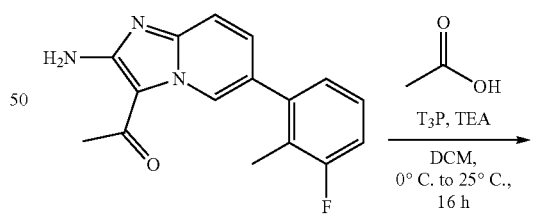

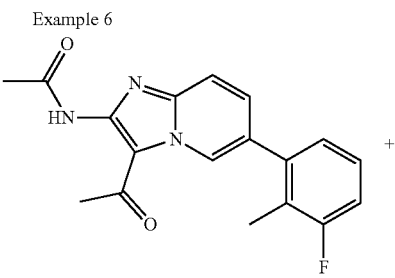

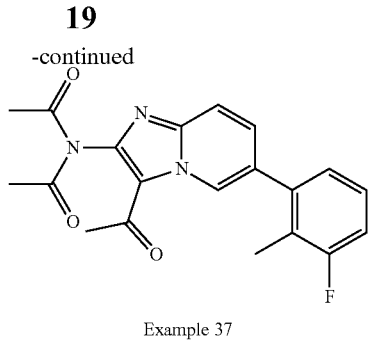

Example 37

To a solution of Example 6 (250 mg, 0.88 mmol, 1 eq) in DCM (10 mL) were added T$_3$P 50% solution (842 mg, 1.32 mmol, 1.5 eq), TEA (295 mg, 2.91 mmol, 406 μL, 3.3 eq), the mixture was stirred at 0° C. for 1 hr, then acetic acid (132 mg, 2.21 mmol, 2.5 eq) was added. The mixture was stirred at 25° C. for 15 hr. The reaction mixture was concentrated under reduced pressure to remove DCM solution to give a residue. The crude product was purified by silica gel chromatography (hexane/ethyl acetate=1/2) to afford Example 33 (24.9 mg, 0.077 mmol, 8.7% yield) and Example 37 (81.7 mg, 0.222 mmol, 25.3% yield) as a white solid.

Example 33; $^1$H NMR (400 MHz, DMSO-d$_6$) δ 10.51 (s, 1H), 9.51 (s, 1H), 7.81 (d, J=9.3 Hz, 1H), 7.68 (dd, J=9.1, 1.9 Hz, 1H), 7.37 (dd, J=14.0, 8.0 Hz, 1H), 7.28 (t, J=8.5 Hz, 1H), 7.20 (d, J=7.7 Hz, 1H), 2.44 (s, 3H), 2.22-2.12 (m, 6H); LCMS (electrospray) m/z 326.10 (M+H)+.

Example 37; $^1$H NMR (400 MHz, DMSO-d$_6$) δ 1H NMR (400 MHz, DMSO-d6) δ 9.57 (d, J=1.1 Hz, 1H), 7.99-7.91 (m, 1H), 7.80 (dd, J=9.1, 1.9 Hz, 1H), 7.44-7.35 (m, 1H), 7.34-7.26 (m, 1H), 7.23 (d, J=7.7 Hz, 1H), 2.37 (s, 3H), 2.35 (s, 6H), 2.20 (d, J=2.7 Hz, 3H); LCMS (electrospray) m/z 368.10 (M+H)+.

Synthetic Method F

Example 54. (6-(3-fluoro-2-methylphenyl)-2-(methylamino)imidazo[1,2-a]pyridin-3-yl)((1S,2S)-2-fluorocyclopropyl)methanone

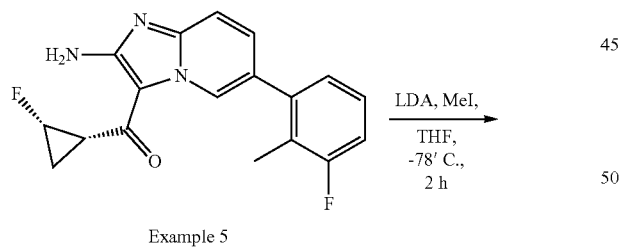

To a solution of Example 5 (50 mg, 0.15 mmol, 1 eq) in THF (0.8 mL) were added 2M LDA solution in THF (113 μl, 0.225 mmol, 1.5 eq) dropwise at −78° C. After 30 min, MeI (20 μl, 0.3 mmol, 2 eq) was added. The reaction mixture was stirred at −78° C. for 2 h. Then the mixture was diluted with water 10 mL and extracted with ethyl acetate (10 mL*2). The combined organic layers were washed with brine (10 mL), dried over Na$_2$SO$_4$, filtered and the filtrate was concentrated. The residue was purified by silica gel column chromatography (0 to 10% gradient MeOH in DCM) to obtain Example 54 (3 mg, 5.8% yield) was obtained.

$^1$H NMR (400 MHz, DMSO-d$_6$) δ 9.56 (s, 1H), 7.59-7.53 (m, 3H), 7.35 (dd, J=13.7, 8.2 Hz, 1H), 7.27-7.18 (m, 3H), 5.28-5.08 (m, 1H), 4.80 (s, 1H), 3.07 (d, J=4.4 Hz, 3H), 2.31 (d, J=18.7 Hz, 1H), 2.18 (d, J=2.2 Hz, 3H), 1.91-1.76 (m, 1H), 1.48 (s, 1H), 1.17-1.08 (m, 1H); LCMS (electrospray) m/z 342.10 (M+H)+.

Synthetic Method G

Example 55. (2-(dimethylamino)-6-(3-fluoro-2-methylphenyl)imidazo[1,2-a]pyridin-3-yl)((1R,2S)-2-fluorocyclopropyl)methanone

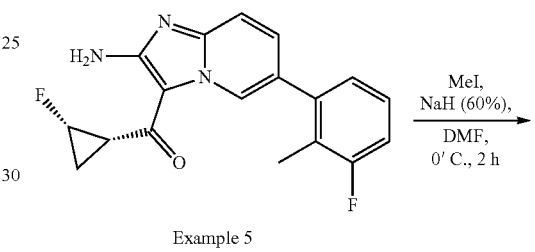

Example 5

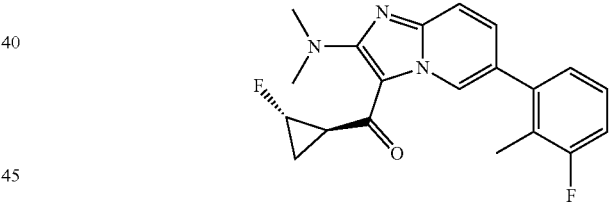

Example 55

To a solution of Example 5 (50 mg, 0.15 mmol, 1 eq) in DMF (0.8 mL) were added NaH (9 mg, 0.375 mmol, 2.5 eq) portion-wise at 0° C. After 30 min, MeI (30 μl, 0.45 mmol, 3 eq) was added. The reaction mixture was stirred at 0° C. for 2 h. Then the mixture was diluted with water 10 mL and extracted with ethyl acetate (10 mL*2). The combined organic layers were washed with brine (10 mL), dried over Na$_2$SO$_4$, filtered and the filtrate was concentrated. The residue was purified by silica gel column chromatography (0 to 8% gradient MeOH in DCM) to obtain Example 55 (18 mg, 33.7% yield) was obtained.

$^1$H NMR (400 MHz, DMSO-d$_6$) δ 9.49 (t, J=1.4 Hz, 1H), 7.70-7.63 (m, 2H), 7.35 (dd, J=13.7, 8.2 Hz, 1H), 7.26 (t, J=8.5 Hz, 1H), 7.16 (d, J=7.7 Hz, 1H), 5.02 (dd, J=67.3, 1.9 Hz, 1H), 3.07 (d, J=12.6 Hz, 6H), 2.16 (d, J=2.2 Hz, 3H), 1.73-1.63 (m, 1H), 1.50 (td, J=12.9, 6.4 Hz, 1H); LCMS (electrospray) m/z 356.10 (M+H)+.

Synthetic Method H

Example 70. tert-butyl (6-(3-fluoro-2-methylphenyl)-3-((1S,2S)-2-fluorocyclopropane-1-carbonyl)imidazo[1,2-a]pyridin-2-yl)carbamate

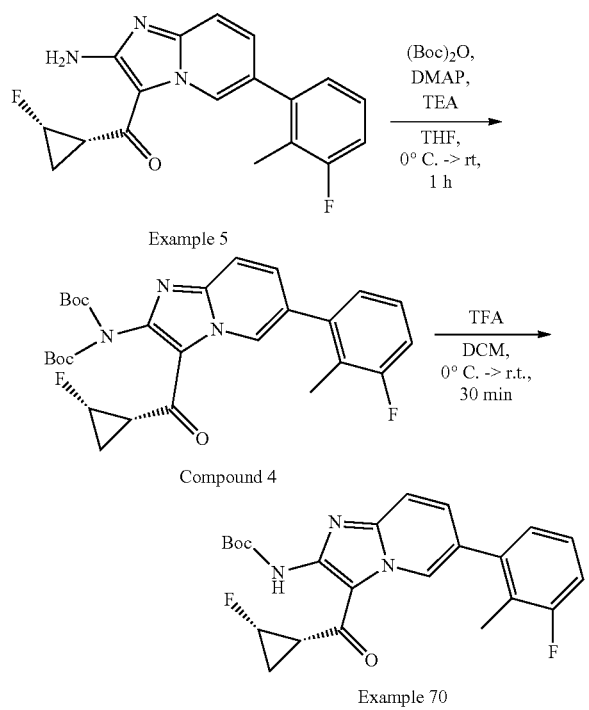

Example 5

Compound 4

Example 70

Step 1) tert-butyl (6-(3-fluoro-2-methylphenyl)-3-((1S,2S)-2-fluorocyclopropane-1-carbonyl)imidazo[1,2-a]pyridin-2-yl)dicarbamate To a solution of Example 5 (500 mg, 1.52 mmol, 1 eq) in THF (7 mL) were added TEA (0.414 mL, 3.04 mmol, 2 eq) and DMAP (92 mg, 0.76 mmol, 0.5 eq) at the room temperature and then cooled to 0° C. Then, Boc anhydride (499 mg, 2.29 mmol, 1.5 eq) was added slowly to reaction mixture, stirred at the room temperature for 1 hr. The reaction mixture was extracted with ethyl acetate and washed with water, separated, dried over anhydrous MgSO$_4$, filtered, and concentrated in vacuo. The residue was purified by silica gel chromatography (product came out at hexane/ethyl acetate=1/2) to afford Compound 4 (720 mg, 1.36 mmol, 89.8% yield) as a white solid.

Step 2) tert-butyl (6-(3-fluoro-2-methylphenyl)-3-((1S,2S)-2-fluorocyclopropane-1-carbonyl)imidazo[1,2-a]pyridin-2-yl)carbamate To a solution of Compound 4 (70 mg, 0.132 mmol, 1 eq) in DCM (1.30 mL) were cooled to 0° C. then TFA (0.101 mL, 1.32 mmol, 10 eq) was added dropwise. The reaction mixture was stirred at rt for 30 min. After the Compound 4 was consumed, the reaction mixture was concentrated and neutralized with saturated aqueous sodium bicarbonate solution. The reaction mixture was extracted with ethyl acetate, separated, dried over anhydrous MgSO$_4$, filtered, and concentrated in vacuo. The residue was purified by silica gel chromatography (product came out at hexane/ethyl acetate=4/6) to afford Example 70 (20 mg, 0.046 mmol, 35% yield) as an ivory solid.

$^1$H NMR (400 MHz, DMSO-d$_6$) δ 9.85 (s, 1H), 9.47 (d, J=1.2 Hz, 1H), 7.80 (d, J=9.2 Hz, 1H), 7.68 (dd, J=9.6, 2.0 Hz, 1H), 7.38-7.33 (m, 1H), 7.27 (t, J=8.8 Hz, 1H), 7.20 (d, J=7.6 Hz, 1H), 5.06-4.83 (m, 1H), 2.91-2.83 (m, 1H), 2.17 (d, J=2.0 Hz, 3H), 1.91-1.80 (m, 1H), 1.46 (s, 9H), 1.28-1.21 (m, 1H); LCMS (electrospray) m/z 428.20 (M+H)+.

Synthetic Method I

Example 71. (6-(3-fluoro-2-methylphenyl)-2-(pyrrolidin-1-yl)imidazo[1,2-a]pyridin-3-yl)((1S,2S)-2-fluorocyclopropyl)methanone

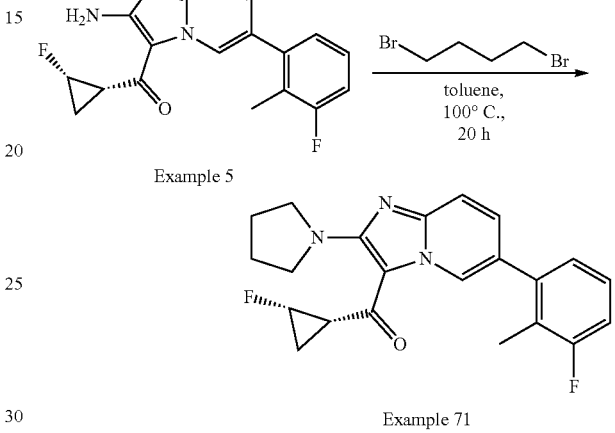

Example 5

Example 71

To a solution of Example 5 (200 mg, 611.01 μmol, 1 eq) in toluene (3 mL) was added DIPEA (157.94 mg, 1.22 mmol, 212.85 μL, 2 eq), DMAP (7.46 mg, 61.10 μmol, 0.1 eq) and 1,4-dibromobutane (791.55 mg, 3.67 mmol, 442.21 μL, 6 eq) under N$_2$. The reaction mixture was stirred at 110° C. for 20 hr. Water (15 mL) was added and the aqueous phase was extracted with EtOAc (10 mL*2). The combined organic phase was washed with saturated brine (10 mL*2) and concentrated in vacuum. The crude product was purified by reversed-phase flash chromatography (MeCN/H$_2$O, 0.05% FA, 70%~85%) to give Example 71 (19.8 mg, 50.20 μmol, 8.22% yield, 96.7% purity) as a light yellow solid.

$^1$H NMR (400 MHz, DMSO-d$_6$) δ 9.64-9.51 (m, 1H), 8.44 (br s, 1H), 7.64-7.55 (m, 2H), 7.42-7.30 (m, 1H), 7.29-7.22 (m, 1H), 7.17 (d, J=7.2 Hz, 1H), 5.37-4.94 (m, 1H), 4.05-3.73 (m, 2H), 2.19 (br s, 1H), 2.16 (d, J=2.3 Hz, 3H), 2.08 (s, 2H), 2.04-1.96 (m, 2H), 1.92 (br dd, J=3.4, 6.3 Hz, 1H), 1.87-1.79 (m, 2H), 1.30-1.11 (m, 1H); LCMS (electrospray) m/z 382.00 (M+H)+.

Synthetic Method J

Example 87. (6-(3-fluoro-2-methylphenyl)-2-((2-(methylamino)ethyl)amino)imidazo[1,2-a]pyridin-3-yl)((1S,2S)-2-fluorocyclopropyl)methanone

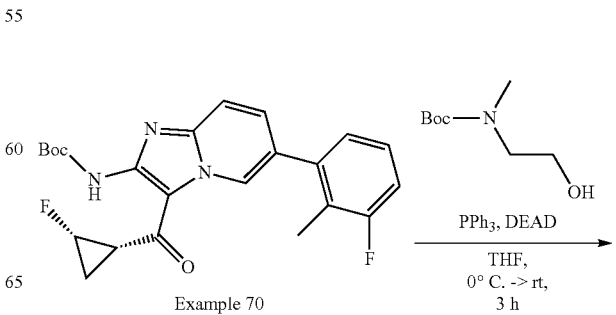

Example 70

23

-continued

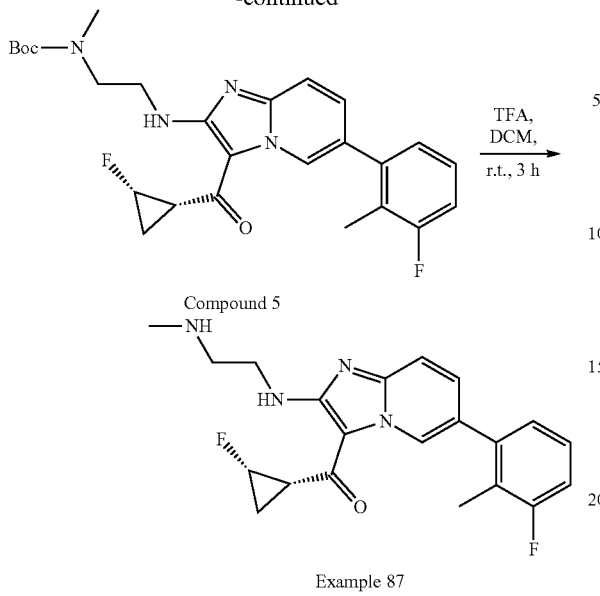

Compound 5

Example 87

Step 1) tert-butyl (2-((6-(3-fluoro-2-methylphenyl)-3-((1S,2S)-2-fluorocyclopropane-1-carbonyl)imidazo[1,2-a]pyridin-2-yl)amino)ethyl)(methyl)carbamate To a solution of Example 70 (300 mg, 0.701 mmol, 1.5 eq) in THF (3 mL) were added PPh₃ (183 mg, 0.701 mmol, 1.5 eq) and tert-butyl (2-hydroxyethyl)(methyl)carbamate (81 mg, 0.467 mmol, 1 eq) at the room temperature and then cooled to 0° C. Then, DEAD (0.318 mL, 0.701 mmol, 1.5 eq) was added slowly to reaction mixture, stirred at the room temperature for 3 hr. The reaction mixture was extracted with ethyl acetate and washed with water, separated, dried over anhydrous MgSO₄, filtered, and concentrated in vacuo. The residue was purified by silica gel chromatography (product came out at hexane/ethyl acetate=6/4) to afford Compound 5 (241 mg, 0.412 mmol, 88% yield) as a white solid.

Step 2) (6-(3-fluoro-2-methylphenyl)-2-((2-(methylamino)ethyl)amino)imidazo[1,2-a]pyridin-3-yl)((1S,2S)-2-fluorocyclopropyl)methanone To a solution of Compound 5 (100 mg, 0.171 mmol, 1 eq) in DCM (1.71 mL) were cooled to 0° C. then TFA (0.261 mL, 3.42 mmol, 20 eq) was added dropwise. The reaction mixture was stirred at rt for 3 hrs. After the Compound 5 was consumed, the reaction mixture was concentrated and neutralized with saturated aqueous sodium bicarbonate solution. The reaction mixture was extracted with ethyl acetate, separated, dried over anhydrous MgSO₄, filtered, and concentrated in vacuo. The residue was purified by silica gel chromatography (product came out at DCM/Methanol=10/1) to afford Example 87 (37 mg, 0.096 mmol, 56% yield) as an ivory solid.

¹H NMR (400 MHz, DMSO-d₆) δ 9.50 (br s, 1H), 7.57-7.51 (m, 2H), 7.36-7.31 (m, 1H), 7.26-7.17 (m, 2H), 5.27-5.07 (m, 1H), 3.58 (q, 6.0 Hz, 2H), 2.76 (t, J=6.0 Hz, 2H), 2.63-2.52 (m, 1H), 2.33 (s, 3H), 2.17 (d, J=1.6 Hz, 3H), 1.89-1.79 (m, 1H), 1.24-1.10 (m, 1H); LCMS (electrospray) m/z 385.15 (M+H)+.

24

Synthetic Method K

Example 88. N-(6-(3-fluoro-2-methylphenyl)-3-((1S,2S)-2-fluorocyclopropane-1-carbonyl)imidazo[1,2-a]pyridin-2-yl)acetamide

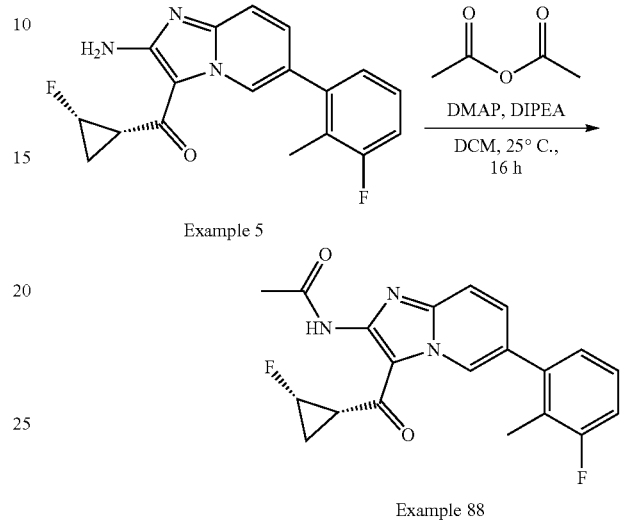

Example 5

Example 88

To a solution of Example 5 (78 mg, 0.24 mmol, 1 eq) in DCM (3 mL) were added acetic anhydride (49 mg, 0.48 mmol, 2.0 eq), DMAP (29 mg, 0.12 mmol, 0.5 eq), DIPEA (62 mg, 0.48 mmol, 2.0 eq). The mixture was stirred at 25° C. for 16 hr. Partitioned between DCM and saturated aqueous sodium bicarbonate solution. The organic layer was washed with saturated aqueous sodium chloride solution, separated, dried over anhydrous Na₂SO₄, filtered, and concentrated in vacuo. The residue was purified by silica gel chromatography (product came out at hexane/ethyl acetate=1/1) to afford Example 88 (19 mg, 0.051 mmol, 21% yield) as an ivory solid.

¹H NMR (400 MHz, DMSO-d₆) δ 10.56 (s, 1H), 9.51 (d, J=1.1 Hz, 1H), 7.83 (d, J=8.8 Hz, 1H), 7.70 (dd, J=9.3, 1.6 Hz, 1H), 7.43-7.32 (m, 1H), 7.28 (t, J=9.1 Hz, 1H), 7.21 (d, J=7.7 Hz, 1H), 5.12-4.82 (m, 1H), 2.87-2.73 (m, 1H), 2.18 (d, J=2.2 Hz, 3H), 2.16 (s, 3H), 1.92-1.75 (m, 1H), 1.30-1.13 (m, 1H); LCMS (electrospray) m/z 370.10 (M+H)+.

Synthetic Method L

Example 89. (2-amino-6-(4-methyl-1H-indol-5-yl)imidazo[1,2-a]pyridin-3-yl)((1S,2S)-2-fluorocyclopropyl)methanone

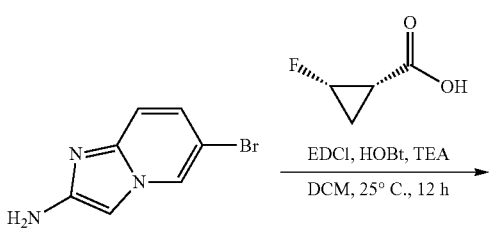

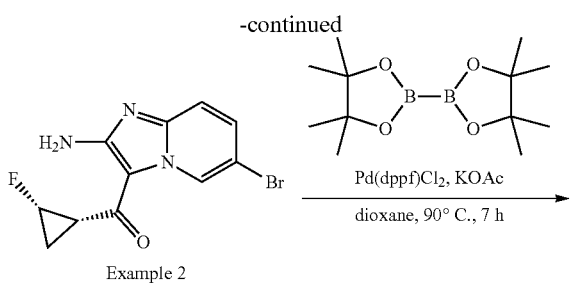

Example 2

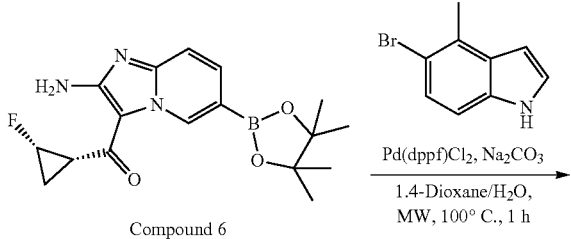

Compound 6

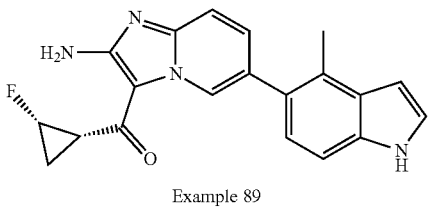

Example 89

Step 1) (2-amino-6-bromoimidazo[1,2-a]pyridin-3-yl)((1S,2S)-2-fluorocyclopropyl)methanone To a solution of 6-bromoimidazo[1,2-a]pyridin-2-amine (5.81 g, 27.4 mmol, 1 eq) in DCM (500 mL) was added EDCI (7.88 g, 41.1 mmol, 1.5 eq), HOBt (6.29 g, 41.1 mmol, 1.5 eq), TEA (4.16 g, 41.1 mmol, 5.73 mL, 1.5 eq), the mixture was stirred at 25° C. for 1 hr, then were added (1S,2S)-2-fluorocyclopropane-1-carboxylic acid (3.42 g, 32.9 mmol, 1.2 eq). The mixture was stirred at 25° C. for 11 hr. The reaction mixture was concentrated under reduced pressure to remove DCM solution to give a residue. The crude product was purified by silica gel chromatography (hexane/ethyl acetate=1/2) to afford Example 2 (6.03 g, 19.62 mmol, 71.6% yield) as a white solid.

$^1$H NMR (400 MHz, DMSO-$d_6$) δ 9.69 (s, 1H), 7.63 (d, J=9.2 Hz, 1H), 7.34 (d, J=10 Hz, 1H), 6.71 (s, 2H), 5.25-5.06 (m, 1H), 2.62-2.51 (m, 1H), 1.91-1.80 (m, 1H), 1.18-1.09 (m, 1H); LCMS (electrospray) m/z 299.00 (M+H)+.

Step 2) (2-amino-6-(4,4,5,5-tetramethyl-1,3,2-dioxaborolan-2-yl)imidazo[1,2-a]pyridin-3-yl)((1S,2S)-2-fluorocyclopropyl)methanone To a solution of Example 2 (3.0 g, 10.06 mmol, 1 eq) in dioxane (50 mL) were added 4,4,4',4',5,5,5',5'-octamethyl-2,2'-bi(1,3,2-dioxaborolane) (3.32 g, 13.08 mmol, 1.3 eq), Pd(dppf)Cl$_2$ (736 mg, 1.00 mmol, 0.1 eq), KOAc (2.96 g, 30.20 mmol, 3 eq) at the room temperature and then heated at 90° C. for 7 hr, cooled down to the room temperature, filtered through a celite pad to remove solids, and partitioned between ethyl acetate and saturated aqueous sodium bicarbonate solution. The organic layer was washed with saturated aqueous sodium chloride solution, separated, dried over anhydrous MgSO$_4$, filtered, and concentrated in vacuo. The residue was purified by silica gel chromatography (hexane/ethyl acetate=1/2) to afford Compound 6 (1.9 g, 5.504 mmol, 54.7% yield) as beige color solid.

$^1$H NMR (400 MHz, DMSO-$d_6$) δ 9.83 (s, 1H), 7.59 (d, J=9.0 Hz, 1H), 7.32 (d, J=9.7 Hz, 1H), 6.73 (s, 2H), 5.23-5.05 (m, 1H), 2.51-2.50 (m, 1H), 1.90-1.81 (m, 1H), 1.31 (s, 9H), 1.15-1.06 (m, 1H); LCMS (electrospray) m/z 346.10 (M+H)+, 264.10 (M−82)+.

Step 3) (2-amino-6-(4-methyl-1H-indol-5-yl)imidazo[1,2-a]pyridin-3-yl)((1S,2S)-2-fluorocyclopropyl)methanone To a solution of Compound 6 (600 mg, 1.738 mmol, 1 eq) in dioxane (7 mL) and water (1.75 mL) were added 5-bromo-4-methyl-1H-indole (365 mg, 1.738 mmol, 1 eq), Na$_2$CO$_3$ (553 mg, 5.21 mmol, 3 eq), Pd(dppf)Cl$_2$ (127 mg, 0.174 mmol, 0.1 eq) at the room temperature and then heated at 100° C. under the microwaves for 1 h, cooled down to the room temperature, filtered through a celite pad to remove solids, and partitioned between ethyl acetate and saturated aqueous sodium bicarbonate solution. The organic layer was washed with saturated aqueous sodium chloride solution, separated, dried over anhydrous MgSO$_4$, filtered, and concentrated in vacuo. The residue was purified by silica gel chromatography (hexane/ethyl acetate=1/1) to afford Example 89 (121 mg, 0.347 mmol, 19.9% yield) as an ivory solid.

$^1$H NMR (400 MHz, DMSO-$d_6$) δ 11.15 (s, 1H), 9.47 (s, 1H), 7.50 (dd, J=9.1, 1.9 Hz, 1H), 7.41-7.32 (m, 2H), 7.28 (d, J=8.2 Hz, 1H), 6.98 (d, J=8.2 Hz, 1H), 6.53 (d, J=33.0 Hz, 3H), 5.30-4.98 (m, 1H), 2.60-2.49 (m, 1H), 2.38 (s, 3H), 1.90-1.68 (m, 1H), 1.11-0.96 (m, 1H); LCMS (electrospray) m/z 349.10 (M+H)+.

Synthetic Method M

Example 99. (2-amino-8-fluoro-6-(3-fluoro-2-methylphenyl)imidazo[1,2-a]pyridin-3-yl)((1S,2S)-2-fluorocyclopropyl)methanone

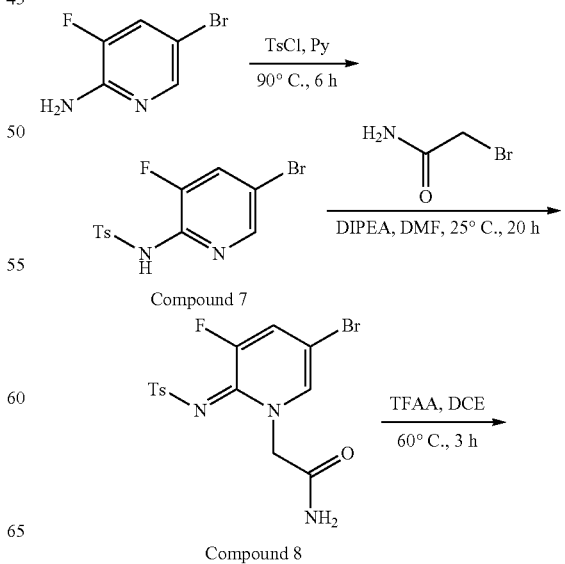

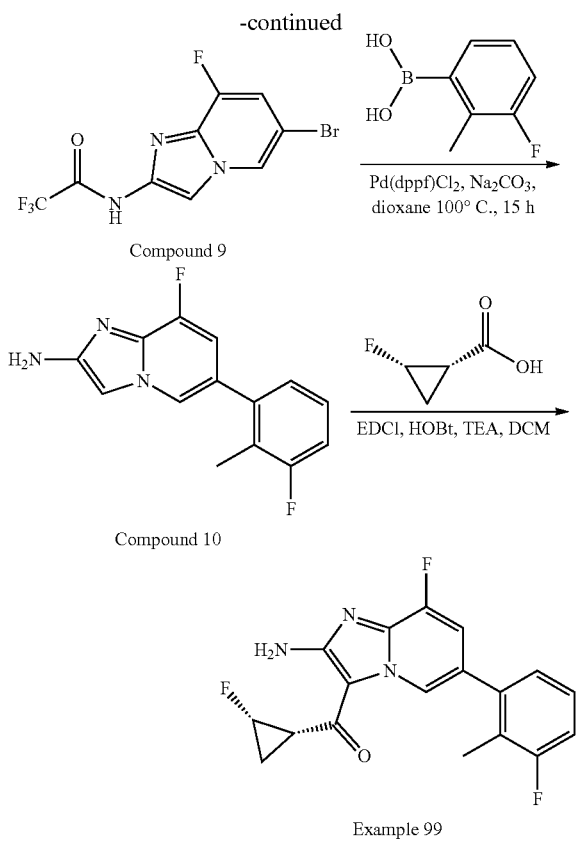

Step 1) N-(5-bromo-3-fluoropyridin-2-yl)-4-methyl-benzenesulfonamide

To a solution of 5-bromo-3-fluoropyridin-2-amine (10 g, 52.36 mmol, 1 eq) in pyridine (100 mL) was added TsCl (10.98 g, 57.59 mmol, 1.1 eq) at 20° C. The mixture was stirred at 90° C. for 16 hr. The mixture was diluted with NaHCO₃ (200 mL) and extracted with ethyl acetate (300 mL). The organic layer was concentrated. The residue was purified by column chromatography (SiO₂, petroleum ether/ethyl acetate=5/1 to 3/1). Compound 7 (10 g, 28.97 mmol, 55.33% yield) was obtained as yellow solid.

Step 2) (E)-2-(5-bromo-3-fluoro-2-(tosylimino)pyridin-1(2H)-yl)acetamide

To a solution of Compound 7 (9 g, 26.07 mmol, 1 eq) in DMF (10 mL) was added DIPEA (3.71 g, 28.68 mmol, 5.00 mL, 1.1 eq) and 2-bromoacetamide (3.96 g, 28.68 mmol, 1.1 eq). The mixture was stirred at 20° C. for 16 hr. The mixture was concentrated. Compound 8 (10 g, crude) was obtained as brown solid.

Step 3) N-(6-bromo-8-fluoroimidazo[1,2-a]pyridin-2-yl)-2,2,2-trifluoroacetamide

To a solution of Compound 8 (5 g, 12.43 mmol, 1 eq) in DCE (10 mL) was added TFAA (31.33 g, 149.17 mmol, 20.75 mL, 12 eq). The mixture was stirred at 60° C. for 3 hr. The mixture was neutralized with saturated NaHCO₃ and extracted with ethyl acetate (300 mL). The organic layer was concentrated. The residue was purified by reversed-phase flash chromatography (0.1% FA condition, 5-70% water/MeCN) and lyophilized to give Compound 9 (2 g, 6.13 mmol, 24.67% yield) as yellow solid.

Step 4) 8-fluoro-6-(3-fluoro-2-methylphenyl)imidazo[1,2-a]pyridin-2-amine

To a solution of Compound 9 (0.5 g, 1.53 mmol, 1 eq) in dioxane (4 mL) and H₂O (1 mL) was added (3-fluoro-2-methylphenyl)boronic acid (283.30 mg, 1.84 mmol, 1.2 eq), Pd(dppf)Cl₂ (112.21 mg, 153.35 μmol, 0.1 eq) and Na₂CO₃ (487.61 mg, 4.60 mmol, 3 eq). The mixture was stirred at 90° C. for 16 hr and concentrated. The residue was purified by reversed-phase flash chromatography (0.1% FA condition, 5-70% water/MeCN) and lyophilized to give Compound 10 (0.35 g, 1.35 mmol, 88.03% yield) as white solid.

Step 5) (2-amino-8-fluoro-6-(3-fluoro-2-methylphenyl)imidazo[1,2-a]pyridin-3-yl)((1S,2S)-2-fluorocyclopropyl)methanone To a solution of Compound 10 (60.22 mg, 578.58 μmol, 1 eq) in DCM (4 mL) was added EDCI (133.10 mg, 694.30 μmol, 1.2 eq), HOBt (93.82 mg, 694.30 μmol, 1.2 eq) and TEA (70.26 mg, 694.30 μmol, 96.64 μL, 1.2 eq). The mixture was stirred at 20° C. for 1 hr, then (1S,2S)-2-fluorocyclopropane-1-carboxylic acid (0.15 g, 578.58 μmol, 1 eq) was added. The mixture was stirred at 20° C. for 15 hr and concentrated. The residue was purified by reversed-phase flash chromatography (0.1% FA condition, 5-70% H₂O/MeCN) and lyophilized to give Example 99 (68 mg, 185.50 μmol, 32.06% yield, 94.2% purity, white solid).
¹H NMR (400 MHz, DMSO-d₆) δ 9.35 (s, 1H), 7.62-7.59 (m, 1H), 7.36-7.19 (m, 3H), 6.87 (s, 1H), 5.29-5.10 (m, 1H), 2.61-2.52 (m, 1H), 2.19 (s, 3H), 1.89-1.84 (m, 1H), 1.17-1.13 (m, 1H); LCMS (electrospray) m/z 346.10 (M+H)+.

Synthetic Method N

Example 107. 2-amino-N-cyclopropyl-6-(3-fluoro-2-methylphenyl)-N-methylimidazo[1,2-a]pyridine-3-carboxamide

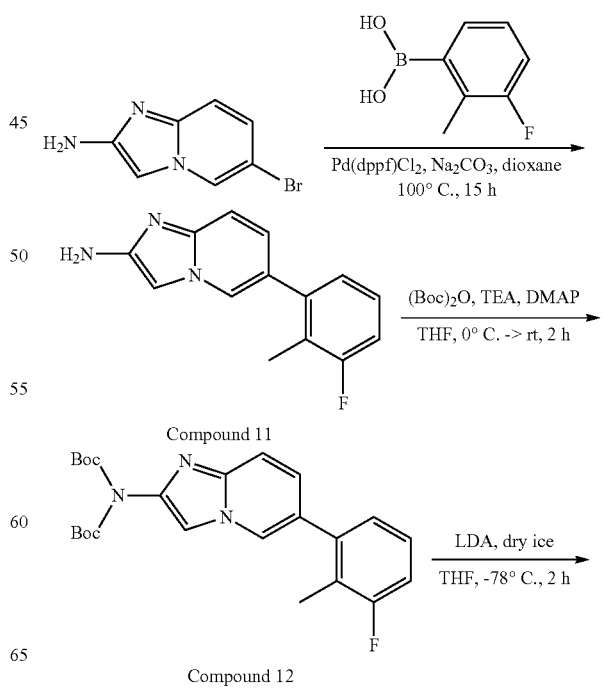

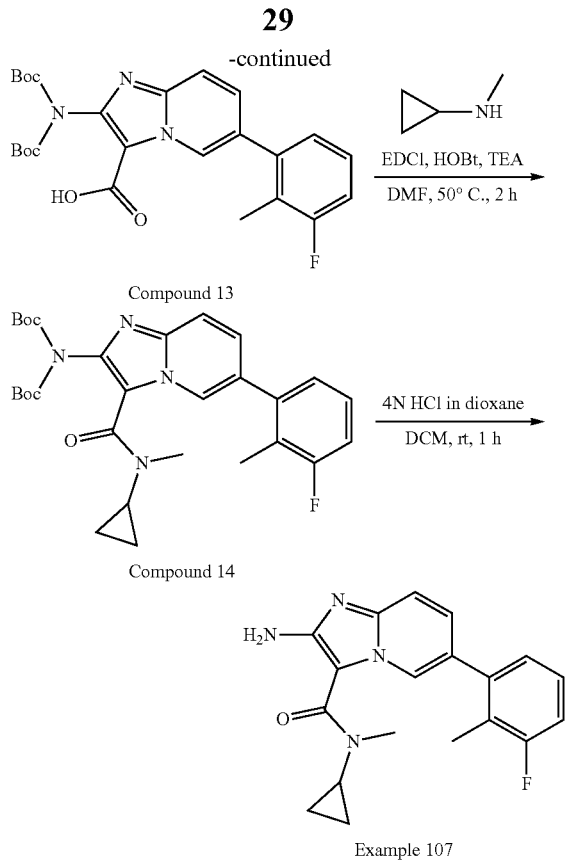

Compound 13

Compound 14

Example 107

Step 1) 6-(3-fluoro-2-methylphenyl)imidazo[1,2-a]pyridin-2-amine

To a solution of 6-bromoimidazo[1,2-a]pyridin-2-amine (324 mg, 1.53 mmol, 1 eq) in dioxane (4 mL) and $H_2O$ (1 mL) was added (3-fluoro-2-methylphenyl)boronic acid (283.30 mg, 1.84 mmol, 1.2 eq), Pd(dppf)Cl$_2$ (112.21 mg, 153.35 μmol, 0.1 eq) and Na$_2$CO$_3$ (487.61 mg, 4.60 mmol, 3 eq). The mixture was stirred at 90° C. for 16 hr. The mixture was concentrated. The residue was purified by reversed-phase flash chromatography (0.1% FA condition, 5-70% H$_2$O/MeCN) and lyophilized to give Compound 11 (107 mg, 1.07 mmol, 70.00% yield) as white solid.

Step 2) Di-tert-butyl (6-(3-fluoro-2-methylphenyl)imidazo[1,2-a]pyridin-2-yl)carbamate To a solution of Compound 11 (500 mg, 2.07 mmol, 1 eq) in THF (10 mL) were added TEA (0.577 mL, 4.14 mmol, 2 eq) and DMAP (126 mg, 1.03 mmol, 0.5 eq) at the room temperature and then cooled to 0° C. Then, Boc anhydride (903 mg, 4.14 mmol, 2.0 eq) was added slowly to reaction mixture and the mixture was stirred at the room temperature for 1 hr. The reaction mixture was extracted with ethyl acetate and washed with water, separated, dried over anhydrous MgSO$_4$, filtered, and concentrated in vacuo. The residue was purified by silica gel chromatography (hexane/ethyl acetate=6/4) to afford Compound 12 (445 mg, 1.00 mmol, 48% yield) as a white solid.

Step 3) 2-(di(tert-butoxycarbonyl)amino)-6-(3-fluoro-2-methylphenyl)imidazo[1,2-a]pyridine-3-carboxylic acid To a solution of Compound 12 (200 mg, 0.453 mmol, 1 eq) in THF (2.26 mL) was cooled to −78° C. and was added LDA (0.906 mL, 1.81 mmol, 4 eq) dropwise then stirred at the same temperature for 30 min. Dry ice was added portion-wise, the reaction mixture was stirred at −78° C. for 2 hrs. Then the reaction mixture was quenched with ice, extracted with DCM, the combined organic phase was washed with water (100 mL), dried over anhydrous MgSO$_4$, filtered, and concentrated in vacuo. The crude product was purified by silica gel chromatography (DCM/Methanol=10/1) to afford Compound 13 (81 mg, 0.166 mmol, 36% yield) as a white solid.

Step 4) Di-tert-butyl (3-(cyclopropyl(methyl)carbamoyl)-6-(3-fluoro-2-methylphenyl)imidazo[1,2-a]pyridin-2-yl)carbamate To a solution of Compound 13 (81 mg, 0.164 mmol, 1 eq) in DMF (0.8 mL) were added N-methylcyclopropanamine (17 mg, 0.247 mmol, 1.5 eq), EDCI (62 mg, 0.328 mmol, 2.0 eq), HOBt (44 mg, 0.328 mmol, 2 eq), TEA (0.068 mL, 0.492 mmol, 3 eq), the mixture was stirred at 50° C. for 2 hr. The reaction mixture was extracted with ethyl acetate and the combined organic phase was washed with aqueous saturated sodium chloride solution (100 mL), dried over anhydrous MgSO$_4$, filtered, and concentrated in vacuo. The crude product was purified by silica gel chromatography (hexane/ethyl acetate=6/4) to afford Compound 14 (49 mg, 0.090 mmol, 55% yield) as a white solid.

Step 5) 2-amino-N-cyclopropyl-6-(3-fluoro-2-methylphenyl)-N-methylimidazo[1,2-a]pyridine-3-carboxamide To a solution of Compound 14 (45 mg, 0.083 mmol, 1 eq) in DCM (0.4 mL) was added 4 N HCl in dioxane (0.2 mL, 0.835 mmol, 10 eq) dropwise. The reaction mixture was stirred at rt for 1 hr. After the Compound 14 was consumed, the reaction mixture was concentrated and neutralized with saturated aqueous sodium bicarbonate solution. The reaction mixture was extracted with ethyl acetate, separated, dried over anhydrous MgSO$_4$, filtered, and concentrated in vacuo. The residue was purified by silica gel chromatography (DCM/Methanol=8/1) to afford Example 107 (22 mg, 0.065 mmol, 78% yield) as an ivory solid.

$^1$H NMR (400 MHz, DMSO-d$_6$) δ 8.49 (s, 1H), 7.35-7.25 (m, 3H), 7.21 (t, J=9.0 Hz, 1H), 7.14 (d, J=7.2 Hz, 1H), 5.71 (s, 2H), 2.94 (s, 3H), 2.91-2.84 (m, 1H), 2.16 (s, 3H), 0.60-0.51 (m, 4H); LCMS (electrospray) m/z 339.10 (M+H)+.

Synthetic Method O

Example 112. N'-acetyl-2-amino-6-(3-fluoro-2-methylphenyl)imidazo[1,2-a]pyridine-3-carbohydrazide

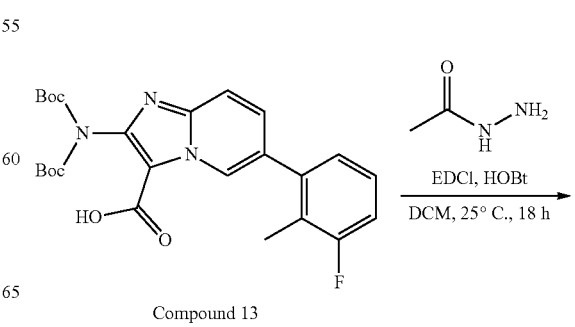

Compound 13

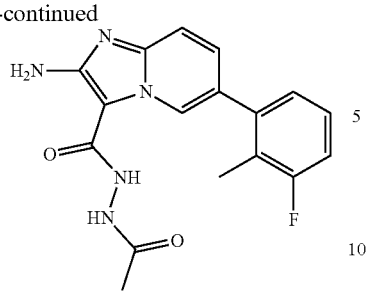

Example 112

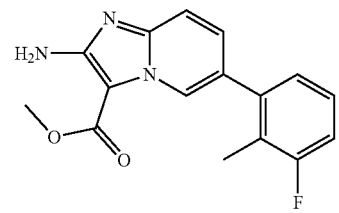

Example 135

To a solution of Compound 13 (84 mg, 0.155 mmol, 1 eq) in DCM (0.8 mL) were added acetohydrazide (13.7 mg, 0.186 mmol, 1.2 eq), EDCI (46 mg, 0.232 mmol, 1.5 eq), HOBt (31.4 mg, 0.232 mmol, 1.5 eq) and the mixture was stirred at 25° C. for 16 hr. The reaction mixture was extracted with DCM (3 mL) and the combined organic phase was washed with aqueous 1N HCl solution (3 mL), dried over anhydrous MgSO$_4$, filtered, and concentrated in vacuo. The crude product was purified by silica gel chromatography (Dichloromethane/Methanol=8/2) to afford Example 112 (4.6 mg, 0.013 mmol, 8.6% yield) as a white solid.

$^1$H NMR (400 MHz, DMSO-d$_6$) δ 9.82 (s, 1H), 9.10 (s, 1H), 9.06 (t, J=1.4 Hz, 1H), 7.39 (d, J=1.1 Hz, 2H), 7.33-7.16 (m, 3H), 6.18 (s, 2H), 2.16 (d, J=2.2 Hz, 3H), 1.90 (s, 3H); LCMS (electrospray) m/z 342.10 (M+H)+.

Synthetic Method P

Example 135. methyl 2-amino-6-(3-fluoro-2-methylphenyl)imidazo[1,2-a]pyridine-3-carboxylate

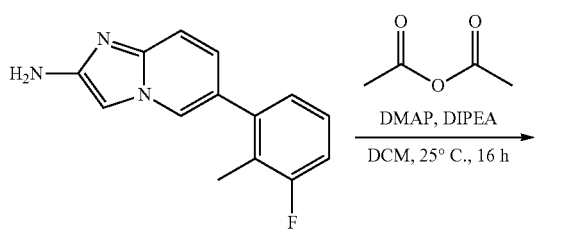

Compound 11

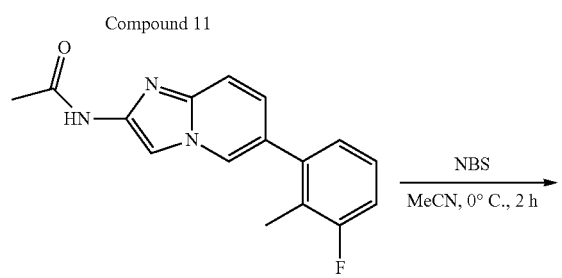

Compound 15

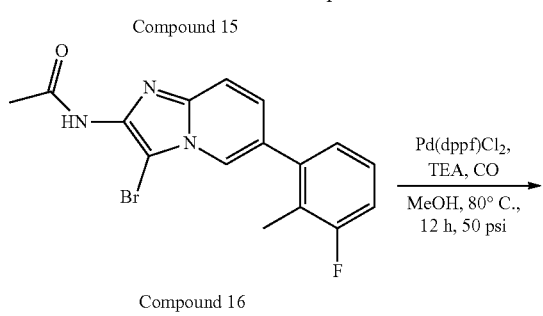

Compound 16

Step 1) N-(6-(3-fluoro-2-methylphenyl)imidazo[1,2-a]pyridin-2-yl)acetamide

To a solution of Compound 11 (58 mg, 0.24 mmol, 1 eq) in DCM (3 mL) were added acetic anhydride (49 mg, 0.48 mmol, 2.0 eq), DMAP (29 mg, 0.12 mmol, 0.5 eq), DIPEA (62 mg, 0.48 mmol, 2.0 eq). The mixture was stirred at 25° C. for 16 hr. The mixture was partitioned between DCM and saturated aqueous sodium bicarbonate solution. The organic layer was washed with saturated aqueous sodium chloride solution, separated, dried over anhydrous Na$_2$SO$_4$, filtered, and concentrated in vacuo. The residue was purified by silica gel chromatography (hexane/ethyl acetate=1/1) to afford Compound 15 (38 mg, 0.13 mmol, 56% yield) as an ivory solid Step 2) N-(3-bromo-6-(3-fluoro-2-methylphenyl)imidazo[1,2-a]pyridin-2-yl)acetamide To a solution of Compound 15 (30 mg, 0.105 mmol, 1 eq) in MeCN (1 mL) were added N-bromosuccinimide (18.6 mg, 0.105 mmol, 1.0 eq) and the mixture was stirred at 0° C. for 2 hr. The reaction mixture was extracted with DCM (3 mL) and the combined organic phase was washed with H$_2$O, dried over anhydrous MgSO$_4$, filtered, and concentrated in vacuo. The Compound 16 (32 mg, 0.09 mmol, 86% yield) was obtained as an ivory solid.

Step 3) methyl 2-amino-6-(3-fluoro-2-methylphenyl)imidazo[1,2-a]pyridine-3-carboxylate To a solution of Compound 16 (300 mg, 828.28 μmol, 1 eq) in MeOH (10 mL) was added TEA (252 mg, 2.48 mmol, 346 μL, 3 eq) and Pd(dppf)Cl$_2$ (61 mg, 82.83 μmol, 0.1 eq) and the reaction mixture was stirred at 80° C. for 12 hrs under CO atmosphere (50 psi). The reaction mixture was filtered and concentrated to give a residue. The residue was purified by column chromatography (silica gel, petroleum ether:ethyl acetate=1:1 to 0:1) and Prep-HPLC (column: Waters Xbridge 150*25 mm*5 um; mobile phase: [water (10 mM NH$_4$HCO$_3$)-ACN]; B %: 30%-63%, 9 min), followed by lyophilization. Example 135 (5.2 mg, 17.37 μmol, 2.10% yield, 100% purity) was obtained as white solid.

$^1$H NMR (400 MHz, DMSO-d$_6$) δ 8.93 (br s, 1H), 7.48-7.43 (m, 1H), 7.42-7.38 (m, 1H), 7.37-7.30 (m, 1H), 7.27-7.21 (m, 1H), 7.17 (d, J=7.7 Hz, 1H), 6.40 (s, 2H), 3.82 (s, 3H), 2.17 (d, J=2.3 Hz, 3H); LCMS (electrospray) m/z 300.10 (M+H)+

Synthetic Method Q

Example 148. (2-amino-6-((3-fluoro-2-methylphenyl)amino)imidazo[1,2-a]pyridin-3-yl)((1S,2S)-2-fluorocyclopropyl)methanone

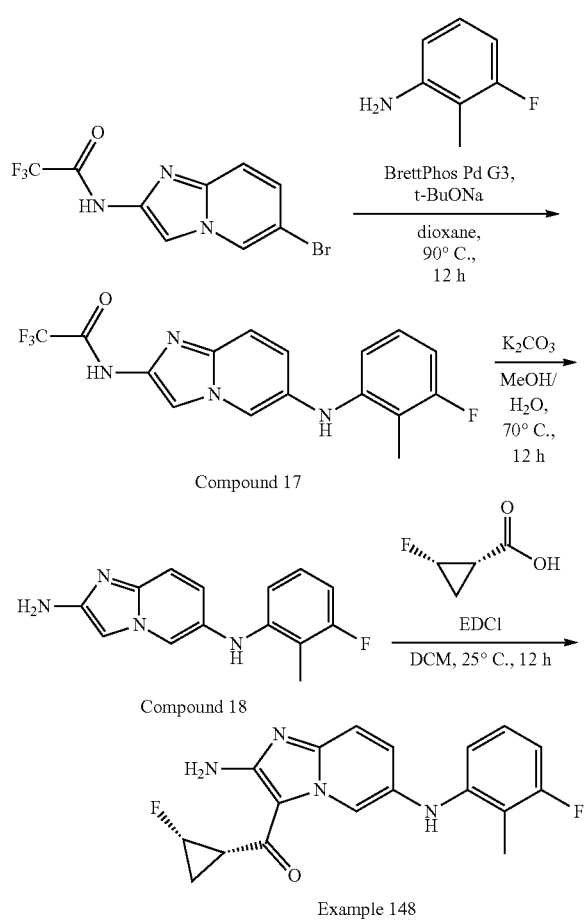

Step 1) 2,2,2-trifluoro-N-(6-((3-fluoro-2-methylphenyl)amino)imidazo[1,2-a]pyridin-2-yl)acetamide To a solution of N-(6-bromoimidazo[1,2-a]pyridin-2-yl)-2,2,2-trifluoroacetamide (500 mg, 1.62 mmol, 1 eq) and 3-fluoro-2-methylaniline (243.74 mg, 1.95 mmol, 221.58 μL, 1.2 eq) in 1,4-dioxane (10 mL) was added BrettPhos Pd G3 (147.13 mg, 162.31 μmol, 0.1 eq), and t-BuONa (2 M, 1.62 mL, 2 eq). The mixture was stirred at 90° C. for 12 h under $N_2$. The reaction mixture was partitioned between ethyl acetate (100 mL*3) and $H_2O$ (100 mL*3). The organic phase was separated, washed with NaCl (100 mL), dried over $Na_2SO_4$, filtered and concentrated under reduced pressure to give a residue. The residue was purified by column chromatography ($SiO_2$, petroleum ether/ethyl acetate=3/1 to 0/1). Compound 17 (100 mg, 283.86 μmol, 17.49% yield) was obtained as brown gum.

Step 2) $N_6$-(3-fluoro-2-methylphenyl)imidazo[1,2-a]pyridine-2,6-diamine

To a solution of Compound 17 (100 mg, 283.86 μmol, 1 eq) in MeOH (5 mL) and $H_2O$ (1 mL) was added $K_2CO_3$ (117.69 mg, 851.58 μmol, 3 eq). The mixture was stirred at 70° C. for 12 hr. The reaction mixture was partitioned between ethyl acetate (50 mL*3) and $H_2O$ (50 mL*3). The organic phase was separated, washed with NaCl (50 mL), dried over $Na_2SO_4$, filtered and concentrated under reduced pressure to give a residue. The residue was purified by column chromatography ($SiO_2$, petroleum ether/ethyl acetate=3/1 to 0/1). Compound 18 (20 mg, 78.04 μmol, 27.49% yield) was obtained as brown solid.

Step 3) (2-amino-6-((3-fluoro-2-methylphenyl)amino)imidazo[1,2-a]pyridin-3-yl)((1S,2S)-2-fluorocyclopropyl)methanone To a solution of Compound 18 (20 mg, 78.04 μmol, 1 eq) and (1S,2S)-2-fluorocyclopropane-1-carboxylic acid (8.12 mg, 78.04 μmol, 1 eq) in DCM (3 mL) was added EDCI (14.96 mg, 78.04 μmol, 1 eq) and HOBt (10.55 mg, 78.04 μmol, 1 eq). The mixture was stirred at 25° C. for 12 hr. The solvent was evaporated under reduced pressure. The residue was purified by column chromatography ($SiO_2$, petroleum ether/ethyl acetate=I/O to 1/1), The crude product was purified by reversed-phase HPLC (0.1% FA condition). Example 148 (0.5 mg, 1.46 μmol, 1.87% yield) was obtained as brown solid.

$^1$H NMR (400 MHz, DMSO-$d_6$) δ 9.46-9.28 (m, 1H), 7.57 (s, 1H) 7.37-7.33 (m, 1H) 7.33-7.29 (m, 1H), 7.09-7.02 (m, 1H), 6.74-6.70 (m, 1H), 6.68-6.65 (m, 1H), 6.42 (br s, 1H), 5.25-5.01 (m, 1H), 2.12 (d, J=1.59 Hz, 3H), 1.88-1.75 (m, 1H), 1.14-1.02 (m, 2H); LCMS (electrospray) m/z 343.10 (M+H)+.

Synthetic Method R

Example 151. (3S,4R)-4-methyltetrahydrofuran-3-yl 2-amino-6-(5-chloro-6-fluoro-7-(methylthio)-1H-indazol-4-yl)imidazo[1,2-a]pyridine-3-carboxylate

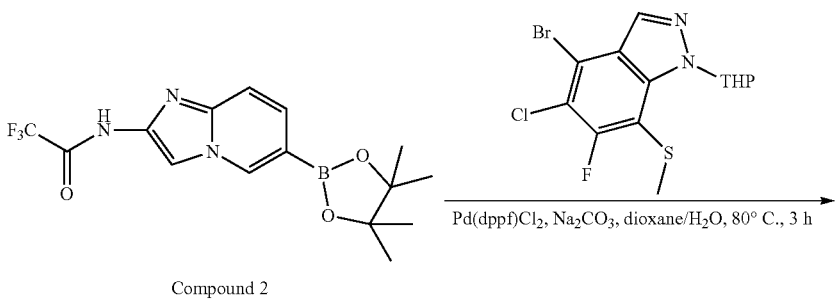

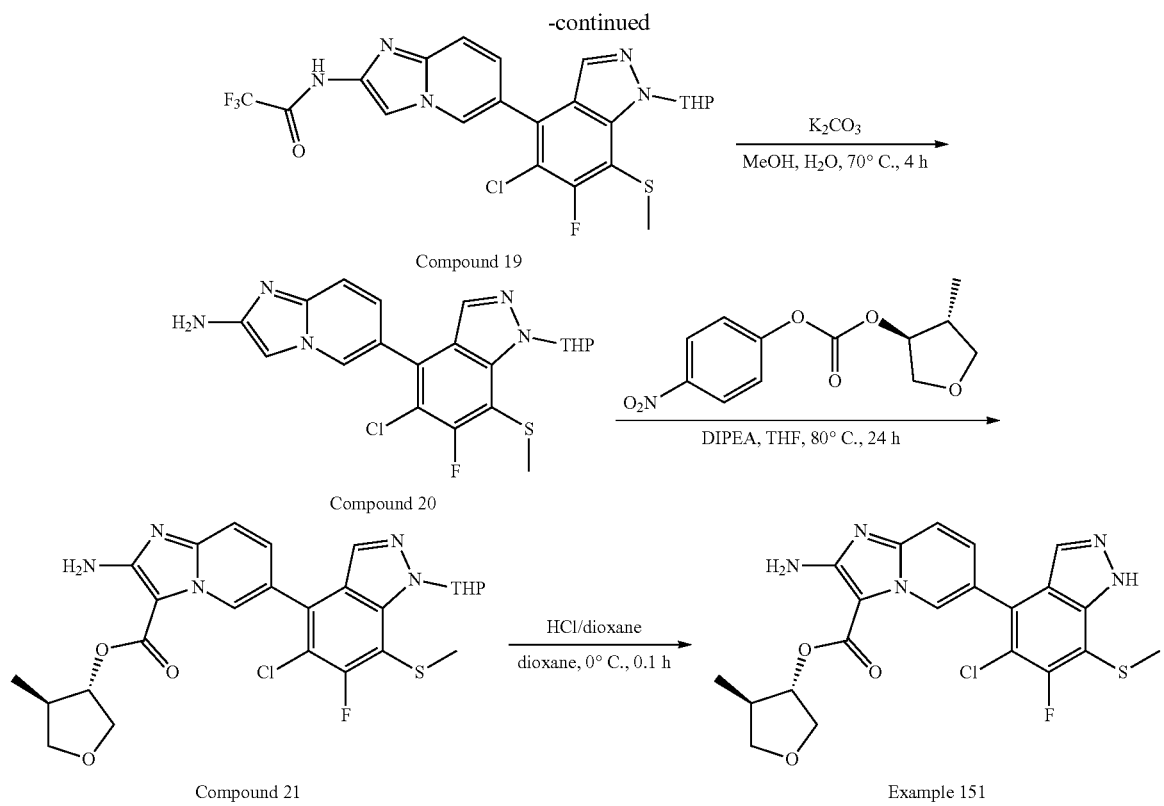

Step 1) N-(6-(5-chloro-6-fluoro-7-(methylthio)-1-(tetrahydro-2H-pyran-2-yl)-1H-indazol-4-yl)imidazo[1,2-a]pyridin-2-yl)-2,2,2-trifluoroacetamide To a mixture of Compound 2 (938 mg, 2.64 mmol, 2 eq) and 4-bromo-5-chloro-6-fluoro-7-(methylthio)-1-(tetrahydro-2H-pyran-2-yl)-1H-indazole (500 mg, 1.32 mmol, 1 eq) in dioxane (25 mL) and H$_2$O (5 mL) was added Pd(dppf)Cl$_2$ (97 mg, 132.00 μmol, 0.1 eq) and Na$_2$CO$_3$ (420 mg, 3.96 mmol, 3 eq) in one portion at 20° C. under N$_2$. The mixture was heated to 80° C. and stirred for 3 hours. The reaction mixture was filtered, and then diluted with H$_2$O (20 mL) and extracted with ethyl acetate (30 mL*3). The combined organic layers were dried over Na$_2$SO$_4$, filtered and concentrated under reduced pressure to give a residue. The residue was purified by column chromatography (SiO$_2$, petroleum ether/ethyl acetate=20/1 to 1/1). Compound 19 (400 mg, 757.69 μmol, 57.40% yield) was obtained as a red oil.

Step 2) 6-(5-chloro-6-fluoro-7-(methylthio)-1-(tetrahydro-2H-pyran-2-yl)-1H-indazol-4-yl)imidazo[1,2-a]pyridin-2-amine To a mixture of Compound 19 (350 mg, 662.98 μmol, 1 eq) in MeOH (20 mL) and H$_2$O (5 mL) was added K$_2$CO$_3$ (458 mg, 3.31 mmol, 5 eq) in one portion at 20° C. under N$_2$. The mixture was heated to 70° C. for 16 hr. The reaction mixture was diluted with water 20 mL and extracted with ethyl acetate (30 mL*3), The combined organic layers were dried over Na$_2$SO$_4$, filtered and concentrated under reduced pressure to give a residue. The crude product was purified by reversed-phase HPLC (0.1% FA condition). Compound 20 (118 mg, 273.20 μmol, 41.21% yield) was obtained as a brown solid.

Step 3) (3S,4R)-4-methyltetrahydrofuran-3-yl 2-amino-6-(5-chloro-6-fluoro-7-(methylthio)-1-(tetrahydro-2H-pyran-2-yl)-1H-indazol-4-yl)imidazo[1,2-a]pyridine-3-carboxylate To a mixture of Compound 20 (80 mg, 185.22 μmol, 1 eq) and (3S,4R)-4-methyltetrahydrofuran-3-yl (4-nitrophenyl) carbonate (248 mg, 926.10 μmol, 5 eq) in THF (10 mL) was added DIPEA (144 mg, 1.11 mmol, 193.57 μL, 6 eq) in one portion at 20° C. under N$_2$. The mixture was then heated to 80° C. and stirred for 24 hours. The reaction mixture was cooled to 20° C., and then quenched by water (20 mL), then the mixture was extracted by ethyl acetate (30 mL*3). The combined organic layers were washed with NaCl solution (30 mL*1), dried over Na$_2$SO$_4$, filtered and concentrated under reduced pressure to give a residue. The residue was purified by column chromatography (SiO$_2$, petroleum ether/ethyl acetate=5/1 to 0/1). Compound 21 (54 mg, crude) was obtained as a yellow oil.

Step 4) (3S,4R)-4-methyltetrahydrofuran-3-yl 2-amino-6-(5-chloro-6-fluoro-7-(methylthio)-1H-indazol-4-yl)imidazo[1,2-a]pyridine-3-carboxylate To a mixture of Compound 21 (54 mg, 96.42 μmol, 1 eq) in dioxane (2 mL) was added HCl/dioxane (4 M, 0.5 mL, 20.74 eq) in dropwise at 0° C. under N$_2$. The mixture was stirred at 0° C. for 0.1 hr. The reaction mixture was quenched by addition Et$_3$N/MeOH (0.5 mL/0.5 mL) at 0° C., and then concentrated under reduced pressure to give a residue. The crude product was purified by reversed-phase HPLC (0.1% FA condition). Example 151 (5.1 mg, 10.72 μmol, 11.11% yield) was obtained as a brown solid.

¹H NMR (400 MHz, DMSO-d₆) δ 13.82 (s, 1H) 9.15 (s, 1H) 8.08 (s, 1H) 7.64 (d, J=9.11, 1H) 7.53 (d, J=9.05 Hz, 1H) 6.29-6.56 (m, 2H) 5.01-5.10 (m, 1H) 3.80-4.03 (m, 4H) 2.56-2.64 (m, 4H) 1.05 (d, J=7.09 Hz, 3H); LCMS (electrospray) m/z 476.00 (M+H)+.

Synthetic Method S

Example 153. (2-amino-5-(6-fluoro-5-methyl-1H-indazol-4-yl)pyrazolo[1,5-a]pyridin-3-yl)(cyclopropyl)methanone

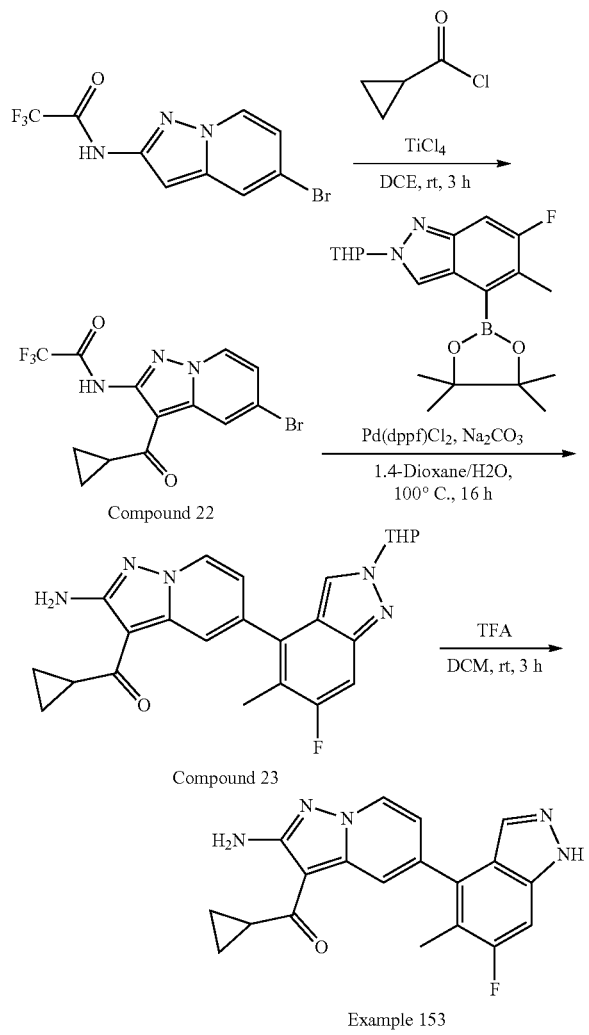

Step 1) N-(5-bromo-3-(cyclopropanecarbonyl)pyrazolo[1,5-a]pyridin-2-yl)-2,2,2-trifluoroacetamide To a solution of N-(5-bromopyrazolo[1,5-a]pyridin-2-yl)-2,2,2-trifluoroacetamide (200 mg, 0.65 mmol, 1.0 eq) in DCM (13 mL) were added cyclopropanecarbonyl chloride (81 mg, 0.78 mmol, 1.2 eq), TiCl₄ (493 mg, 2.601 mmol, 4.0 eq) at the room temperature and then heated at 80° C. for 16 hr. The mixture was cooled down to the room temperature, quenched with saturated NaHCO₃ and extracted with DCM (3×100 mL). The organic layer was washed with saturated aqueous sodium chloride solution, separated, dried over anhydrous Na₂SO₄, filtered, and concentrated in vacuo. The residue was purified by silica gel chromatography (hexane/ethyl acetate=3/1) to afford Compound 22 (169 mg, 0.449 mmol, 69% yield) as a brown solid.

¹H NMR (400 MHz, DMSO-d₆) δ 12.14 (s, 1H), 8.84 (dd, J=7.1, 2.2 Hz, 1H), 8.38 (d, J=2.2 Hz, 1H), 7.40 (dd, J=7.7, 2.2 Hz, 1H), 2.56-2.48 (m, 1H), 1.09-1.00 (m, 2H), 1.00-0.93 (m, 2H).

Step 2) (2-amino-5-(6-fluoro-5-methyl-2-(tetrahydro-2H-pyran-2-yl)-2H-indazol-4-yl)pyrazolo[1,5-a]pyridin-3-yl)(cyclopropyl)methanone To a solution of Compound 22 (80 mg, 0.21 mmol, 1.0 eq) in dioxane (2 mL) and H₂O (1 mL) were added 6-fluoro-5-methyl-2-(tetrahydro-2H-pyran-2-yl)-4-(4,4,5,5-tetramethyl-1,3,2-dioxaborolan-2-yl)-2H-indazole (115 mg, 0.32 mmol, 1.5 eq), Na₂CO₃ (45 mg, 0.43 mmol, 2.0 eq), Pd(dppf)Cl₂ (16 mg, 0.02 mmol, 0.1 eq) at the room temperature and then heated at 100° C. for 16 hr. The mixture was cooled down to the room temperature, filtered through a celite pad to remove solids, and partitioned between ethyl acetate and saturated aqueous sodium bicarbonate solution. The organic layer was washed with aqueous saturated sodium chloride solution, separated, dried over anhydrous Na₂SO₄, filtered, and concentrated in vacuo. The residue was purified by silica gel chromatography (hexane/ethyl acetate=1/1) to afford Compound 23 (44 mg, 0.101 mmol, 48% yield) as an ivory solid.

¹H NMR (400 MHz, DMSO-d₆) δ 8.67 (d, J=7.7 Hz, 1H), 7.94 (d, J=1.1 Hz, 1H), 7.85 (s, 1H), 7.70 (d, J=10.4 Hz, 1H), 7.01 (dd, J=6.7, 2.1 Hz, 1H), 6.66 (s, 2H), 5.84 (dd, J=9.9, 2.7 Hz, 1H), 3.94-3.84 (m, 1H), 3.84-3.69 (m, 1H), 2.49-2.45 (m, 1H), 2.45-2.30 (m, 1H), 2.24 (d, J=2.7 Hz, 3H), 2.13-1.89 (m, 2H), 1.84-1.66 (m, 1H), 1.66-1.50 (m, 2H), 1.05-0.91 (m, 2H), 0.91-0.80 (m, 2H).

Step 3) (2-amino-5-(6-fluoro-5-methyl-1H-indazol-4-yl)pyrazolo[1,5-a]pyridin-3-yl)(cyclopropyl)methanone To a solution of Compound 23 (40 mg, 0.09 mmol, 1.0 eq) in DCM (1 mL) was added TFA (316 mg, 2.77 mmol, 30.0 eq). The mixture was stirred at 25° C. for 3 hr. The reaction mixture was adjusted to pH 7 with saturated aqueous NaHCO₃ solution. The mixture was diluted with water (20 mL) and extracted with ethyl acetate. The combined organic layers were washed with brine, dried over Na₂SO₄, filtered and concentrated under reduced pressure to give a residue. The residue was purified by silica gel chromatography (hexane/ethyl acetate=1/3) to afford Example 153 (21.2 mg, 0.061 mmol, 66% yield) as an ivory solid.

¹H NMR (400 MHz, DMSO-d₆) δ 13.23 (s, 1H), 8.66 (d, J=6.6 Hz, 1H), 7.95 (s, 1H), 7.81 (s, 1H), 7.42 (d, J=9.9 Hz, 1H), 7.02 (dd, J=7.1, 1.6 Hz, 1H), 6.66 (s, 2H), 2.49-2.43 (m, 1H), 2.24 (d, J=2.7 Hz, 3H), 1.03-0.92 (m, 2H), 0.92-0.82 (m, 2H); LCMS (electrospray) m/z 350.10 (M+H)+.

Table 1 below shows the compounds of Examples along with general synthetic methods used to make the compound and characterization data.

TABLE 1

| Ex # | Structure/Name | 1H NMR/MS (M + 1) | Synthetic Method |
|---|---|---|---|
| 1 | 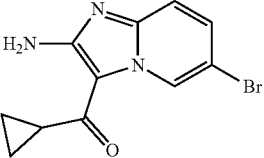<br>(2-amino-6-bromoimidazo[1,2-a]pyridin-3-yl)(cyclopropyl)methanone | $^1$H NMR (400 MHz, DMSO-d$_6$) δ 9.70 (d, J = 1.2 Hz, 1H), 7.60 (dd, J = 2.1, 9.3 Hz, 1H), 7.32 (d, J = 9.3 Hz, 1H), 6.62 (s, 2H), 2.46-2.37 (m, 1H), 1.02-0.90 (m, 4H); LCMS (electrospray) m/z 282.10 (M + 2H)+. | A |
| 2 | 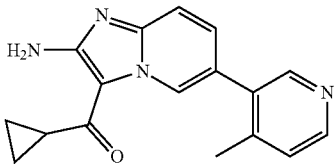<br>(2-amino-6-(4-methylpyridin-3-yl)imidazo[1,2-a]pyridin-3-yl)(cyclopropyl)methanone | $^1$H NMR (400 MHz, DMSO-d$_6$) δ 9.49 (s, 1H), 8.43 (d, J = 5.6 Hz, 1H), 8.39 (s, 1H), 7.50 (d, J = 1.6 Hz, 1H), 7.39 (d, J = 8.8 Hz, 1H), 7.34 (d, J = 5.6 Hz, 1H), 6.53 (NH, 2H), 2.45-2.42 (m, 1H), 2.25 (s, 3H), 0.94-0.88 (m, 4H); LCMS (electrospray) m/z 293.10 (M + H)+. | B |
| 3 | 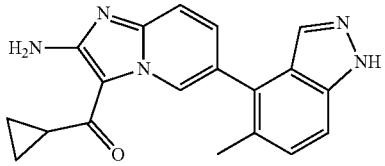<br>(2-amino-6-(5-methyl-1H-indazol-4-yl)imidazo[1,2-a]pyridin-3-yl)(cyclopropyl)methanone | $^1$H NMR (400 MHz, DMSO-d$_6$) δ 13.07 (NH, 1H), 9.56 (s, 1H), 7.68 (s, 1H), 7.50 (d, J = 1.6 Hz, 1H), 7.44-7.41 (m, 2H), 7.28 (d, J = 8.4 Hz, 1H), 6.53 (NH, 2H), 2.46-2.45 (m, 1H), 0.92-0.86 (m, 4H); LCMS (electrospray) m/z 332.10 (M + H)+. | B |
| 4 | 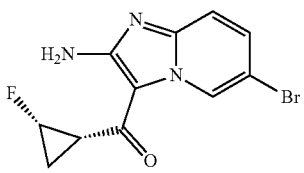<br>(2-amino-6-bromoimidazo[1,2-a]pyridin-3-yl)((1S,2S)-2-fluorocyclopropyl)methanone | $^1$H NMR (400 MHz, DMSO-d$_6$) δ 9.69 (s, 1H), 7.63 (d, J = 9.2 Hz, 1H), 7.34 (d, J = 10 Hz, 1H), 6.71 (s, 2H), 5.25-5.06 (m, 1H), 2.62-2.51 (m, 1H), 1.91-1.80 (m, 1H), 1.18-1.09 (m, 1H); LCMS (electrospray) m/z 299.00 (M + H)+. | A |
| 5 | 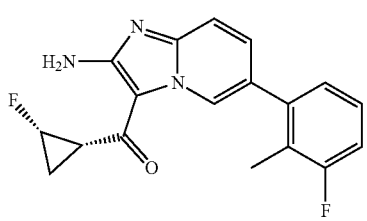<br>(2-amino-6-(3-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.52 (s, 1H), 7.54 (dd, J = 1.6, 8.8 Hz, 1H), 7.43 (d, J = 8.8 Hz, 1H), 7.30 (q, J = 7.6 Hz, 1H), 7.23 (t, J = 8.8 Hz, 1H), 7.16 (d, J = 7.6 Hz, 1H), 6.67 (s, 2H), 5.27-5.06 (m, 1H), 2.60-2.51 (m, 1H), 2.17 (s, 3H), 1.89-1.78 (m, 1H), 1.14-1.07 (m, 1H); LCMS (electrospray) m/z 328.10 (M + H)+. | B |

TABLE 1-continued

Compounds of Examples

| Ex # | Structure/Name | 1H NMR/MS (M + 1) | Synthetic Method |
|---|---|---|---|
| 6 | 1-(2-amino-6-(3-fluoro-2-methylphenyl)imidazo[1,2-a]pyridin-3-yl)ethan-1-one | $^1$H NMR (400 MHz, DMSO-d$_6$) δ 9.49 (brs, 1H), 7.51 (dd, J = 1.2, 8.8 Hz, 1H), 7.41 (d, J = 8.0 Hz, 1H), 7.34 (q, J = 7.6 Hz, 1H), 7.23 (t, J = 8.4 Hz, 1H), 7.16 (d, J = 7.2 Hz, 1H), 6.47 (s, 2H), 2.44 (s, 3H), 2.16 (s, 3H); LCMS (electrospray) m/z 284.10 (M + H)+. | B |
| 7 | (2-amino-6-(4-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.48 (s, 1H), 7.52 (dd, J = 1.6, 8.8 Hz, 1H), 7.41 (d, J = 9.6 Hz, 1H), 7.33 (dd, J = 6.4, 8.4 Hz, 1H), 7.21 (dd, J = 3.2, 10.4 Hz, 1H), 7.12 (dt, J = 2.8, 8.8 Hz, 1H), 6.65 (s, 2H), 5.27-5.06 (m, 1H), 2.62-2.53 (m, 1H), 2.27 (s, 3H), 1.89-1.78 (m, 1H), 1.13-1.05 (m, 1H); LCMS (electrospray) m/z 328.10 (M + H)+. | B |
| 8 | (2-amino-6-(thiophen-2-yl)imidazo[1,2-a]pyridin-3-yl)((1S,2S)-2-fluorocyclopropyl)methanone | $^1$H NMR (400 MHz, DMSO-d$_6$) δ 9.88 (s, 1H), 7.84 (dd, J = 1.6, 8.8 Hz, 1H), 7.58 (dd, J = 0.8 4.8 Hz, 1H), 7.50 (dd, J = 1.2, 3.2 Hz, 1H), 7.42 (d, J = 8.8 Hz, 1H), 7.16 (dd, J = 3.6, 5.2 Hz, 1H), 6.69 (s, 2H), 5.29-5.06 (m, 1H), 2.63-2.53 (m, 1H), 1.94-1.82 (m, 1H), 1.19-1.07 (m, 1H); LCMS (electrospray) m/z 302.05 (M + H)+. | B |
| 9 | (2-amino-6-(2-(trifluoromethyl)phenyl)imidazo[1,2-a]pyridin-3-yl)((1S,2S)-2-fluorocyclopropyl)methanone | $^1$H NMR (400 MHz, DMSO-d$_6$) δ 11.89 (br s, 1H), 11.13 (s, 1H), 8.59 (d, J = 7.2 Hz, 1H), 8.21 (s, 1H), 7.62-7.59 (m, 1H), 7.57-7.52 (m, 1H), 6.91 (d, J = 2.0 Hz, 1H), 6.89 (s, 1H), 6.69-6.64 (m, 1H), 5.10-4.80 (m, 1H), 2.55 (s, 3H), 2.24-2.06 (m, 1H), 1.82-1.54 (m, 1H), 1.27-1.12 (m, 1H); LCMS (electrospray) m/z 350.1 (M + H)+. | B |
| 10 | (2-amino-6-(3-fluoro-2-(trifluoromethyl)phenyl)imidazo[1,2-a]pyridin-3-yl)((1S,2S)-2-fluorocyclopropyl)methanone | $^1$H NMR (400 MHz, DMSO-d$_6$) δ 9.53 (s, 1H), 7.84-7.77 (m, 1H), 7.60 (dd, J = 8.8, 11.6 Hz, 1H), 7.50-7.41 (m, 2H), 7.37 (d, J = 7.6 Hz, 1H), 6.70 (s, 2H), 5.28-5.05 (m, 1H), 2.62-2.52 (m, 1H), 1.88-1.77 (m, 1H), 1.14-1.04 (m, 1H); LCMS (electrospray) m/z 382.10 (M + H)+. | B |

TABLE 1-continued

Compounds of Examples

| Ex # | Structure/Name | 1H NMR/MS (M + 1) | Synthetic Method |
|---|---|---|---|
| 11 | (2-amino-6-(2,3-dimethylphenyl)imidazo[1,2-a]pyridin-3-yl)((1S,2S)-2-fluorocyclopropyl)methanone | $^1$H NMR (400 MHz, DMSO-$d_6$) δ 9.46 (s, 1H), 7.47 (dd, J = 1.6, 8.8 Hz, 1H), 7.41 (d, J = 8.8 Hz, 1H), 7.23 (d, J = 6.4 Hz, 1H), 7.17 (t, J = 7.2 Hz, 1H), 7.11 (d, J = 6.4 Hz, 1H), 6.63 (s, 2H), 5.28-5.05 (m, 1H), 2.63-2.52 (m, 1H), 2.31 (s, 3H), 2.13 (s, 3H), 1.89-1.77 (m, 1H), 1.14-1.04 (m, 1H); LCMS (electrospray) m/z 324.10 (M + H)+. | B |
| 12 | (2-amino-6-(3-fluoro-2-methylphenyl)imidazo[1,2-a]pyridin-3-yl)(pyridin-2-yl)methanone | $^1$H NMR (400 MHz, DMSO-$d_6$) δ 9.77 (br s, 1H), 8.77-8.76 (m, 1H), 8.14-8.07 (m, 2H), 7.77 (br s, 2H), 7.70-7.66 (m, 1H), 7.62 (dd, J = 1.6, 8.8 Hz, 1H), 7.45-7.43 (m, 1H), 7.38-7.33 (m, 1H), 7.27-7.19 (m, 2H), 2.20 (d, J = 2.0 Hz, 3H); LCMS (electrospray) m/z 347.1 (M + H)+. | B |
| 13 | (2-amino-6-(3-fluoro-2-methylphenyl)imidazo[1,2-a]pyridin-3-yl)(phenyl)methanone | $^1$H NMR (400 MHz, DMSO-$d_6$) δ 9.06 (br s, 1H), 7.61-7.54 (m, 6H), 7.47-7.44 (m, 1H), 7.35-7.30 (m, 1H), 7.25-7.20 (m, 1H), 7.13 (d, J = 6.8 Hz, 1H), 5.77 (br s, 2H), 2.15 (d, J = 2.0 Hz, 3H); LCMS (electrospray) m/z 346.1 (M + H)+. | B |
| 14 | (2-amino-6-(3-fluoro-2-methylphenyl)imidazo[1,2-a]pyridin-3-yl)(cyclopropyl)methanone | $^1$H NMR (400 MHz, DMSO-$d_6$) δ 9.47 (br s, 1H), 7.46 (dd, J = 1.8, 9.0 Hz, 1H), 7.38-7.35 (m, 1H), 7.31-7.25 (m, 1H), 7.20-7.16 (m, 1H), 7.10 (d, J = 7.2 Hz, 1H), 6.53 (br s, 2H), 2.43-2.36 (m, 1H),, 2.11 (d, J = 2.0 Hz, 3H), 0.94-0.85 (m, 4H); LCMS (electrospray) m/z 310.1 (M + H)+. | B |
| 15 | (2-amino-6-(5-fluoro-2-methylphenyl)imidazo[1,2-a]pyridin-3-yl)((1S,2S)-2-fluorocyclopropyl)methanone | $^1$H NMR (400 MHz, DMSO-$d_6$) δ 9.48 (s, 1H), 7.51 (dd, J12 = 1.8 Hz, J13 = 9.0 Hz, 1H), 7.34-7.32 (m, 2H), 7.15-7.11 (m, 2H), 6.63 (s, 2H), 5.24-5.04 (m, 1H), 2.56-2.52 (m, 1H), 2.20 (s, 3 H), 1.86-1.75 (m, 1H), 1.11-1.02 (m, 1H); LCMS (electrospray) m/z 328.10 (M + H)+. | B |

TABLE 1-continued

Compounds of Examples

| Ex # | Structure/Name | 1H NMR/MS (M + 1) | Synthetic Method |
|---|---|---|---|
| 16 | 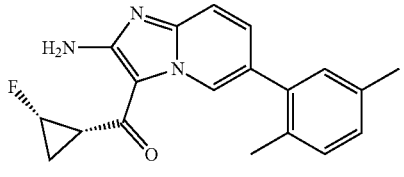<br>(2-amino-6-(2,5-dimethylphenyl)imidazo[1,2-a]pyridin-3-yl)((1S,2S)-2-fluorocyclopropyl)methanone | $^1$H NMR (400 MHz, DMSO-$d_6$) δ 9.50 (s, 1H), 7.52 (dd, J12 = 1.8 Hz, J13 = 9.0 Hz, 1H), 7.40 (d, J = 10.0 Hz, 1H), 7.21 (d, J = 7.6 Hz, 1H), 7.14-7.09 (m, 2H), 6.64 (s, 2H), 5.26-5.07 (m, 1H), 2.61-2.53 (m, 1H), 2.31 (s, 3H), 2.21 (s, 3H), 1.89-1.78 (m, 1H), 1.14-1.05 (m, 1H)); LCMS (electrospray) m/z 324.10 (M + H)+. | B |
| 17 | 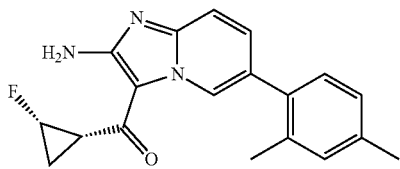<br>(2-amino-6-(2,4-dimethylphenyl)imidazo[1,2-a]pyridin-3-yl)((1S,2S)-2-fluorocyclopropyl)methanone | $^1$H NMR (400 MHz, DMSO-$d_6$) δ 9.44 (s, 1H), 7.46 (dd, J12 = 1.8 Hz, J13 = 9.0 Hz, 1H), 7.36 (d, J = 10.0 Hz, 1H), 7.13 (d, J = 7.6 Hz, 2H), 7.07-7.05 (m, 1H), 6.59 (s, 2H), 5.23-5.02 (m, 1H), 2.55-2.50 (m, 1H), 2.29 (s, 3H), 2.19 (s, 3H), 1.85-1.75 (m, 1H), 1.10-1.09 (m, 1H)); LCMS (electrospray) m/z 324.10 (M + H)+. | B |
| 18 | 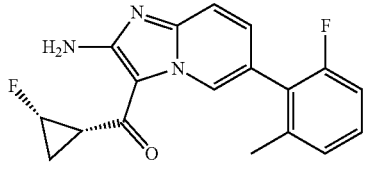<br>(2-amino-6-(2-fluoro-6-methylphenyl)imidazo[1,2-a]pyridin-3-yl)((1S,2S)-2-fluorocyclopropyl)methanone | $^1$H NMR (400 MHz, DMSO-$d_6$) δ 9.47 (s, 1H), 7.46 (d, J = 0.8 Hz, 2H), 7.41-7.34 (m, 1H), 7.23-7.12 (m, 2H), 6.68 (s, 2H), 5.28-5.05 (m, 1H), 2.62-2.52 (m, 1H), 2.18 (s, 3H), 1.88-1.77 (m, 1H), 1.14-1.04 (m, 1H); LCMS (electrospray) m/z 328.10 (M + H)+. | B |
| 19 | 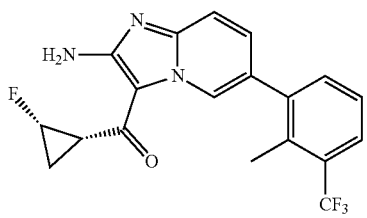<br>(2-amino-6-(2-methyl-3-(trifluoromethyl)phenyl)imidazo[1,2-a]pyridin-3-yl)((1S,2S)-2-fluorocyclopropyl)methanone | $^1$H NMR (400 MHz, DMSO-$d_6$) δ 9.46 (s, 1H), 7.74 (d, J = 7.6 Hz, 1H), 7.57 (d, J = 7.2 Hz, 1H), 7.51 (dd, J = 2.4, 9.6 Hz, 1H), 7.46 (t, J = 7.6 Hz, 1H), 7.40 (d, J = 9.6 Hz, 1H), 6.65 (s, 2H), 5.25-5.02 (m, 1H), 2.60-2.49 (m, 1H), 2.29 (s, 3H), 1.86-1.73 (m, 1H), 1.12-1.01 (m, 1H); LCMS (electrospray) m/z 378.10 (M + H)+. | B |
| 20 | 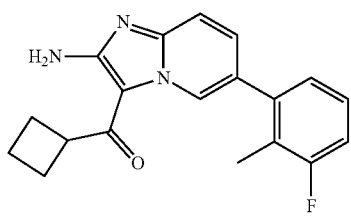<br>(2-amino-6-(3-fluoro-2-methylphenyl)imidazo[1,2-a]pyridin-3-yl)cyclobutyl)methanone | $^1$H NMR (400 MHz, DMSO-$d_6$) δ 9.57 (br s, 1H), 7.50 (dd, J = 9.0, 1.8 Hz, 1H), 7.40-7.38 (m, 1H), 7.37-7.31 (m, 1H), 7.26-7.21 (m, 1H), 7.17 (d, J = 7.2 Hz, 1H), 6.40 (br s, 2H), 3.86-3.78 (m, 1H), 2.28-2.22 (m, 4H), 2.17 (d, J = 2.0 Hz, 3H), 2.02-1.91 (m, 1H), 1.83-1.74 (m, 1H); LCMS (electrospray) m/z 324.1 (M + H)+. | B |

TABLE 1-continued

Compounds of Examples

| Ex # | Structure/Name | 1H NMR/MS (M + 1) | Synthetic Method |
|---|---|---|---|
| 21 | (2-amino-6-(3-fluoro-2-methylphenyl)imidazo[1,2-a]pyridin-3-yl)(1-methyl-1H-pyrazol-4-yl)methanone | $^1$H NMR (400 MHz, DMSO-d$_6$) δ 9.20 (s, 1H), 8.22 (s, 1H), 7.82 (s, 1H), 7.50 (dd, J = 9.0, 1.8 Hz, 1H), 7.43-7.41 (m, 1H), 7.36-7.30 (m, 1H), 7.25-7.20 (m, 1H), 7.16 (d, J = 7.2 Hz, 1H), 6.08 (s, 2H), 3.89 (s, 3H), 2.17 (d, J = 2.0 Hz, 3H); LCMS (electrospray) m/z 350.1 (M + H)+. | B |
| 22 | 1-(2-amino-6-(3-fluoro-2-methylphenyl)imidazo[1,2-a]pyridin-3-yl)-2,2-dimethylpropan-1-one | $^1$H NMR (400 MHz, DMSO-d$_6$) δ 9.61 (br s, 1H), 7.51-7.49 (m, 1H), 7.41-7.38 (m, 1H), 7.32 (q, J = 7.2 Hz, 1H), 7.25-7.20 (m, 1H), 7.15 (d, J = 7.2 Hz, 1H), 6.21 (br s, 2H), 2.16 (s, 3H), 1.30 (s, 9H); LCMS (electrospray) m/z 326.15 (M + H)+. | B |
| 23 | 1-(2-amino-6-(3-fluoro-2-methylphenyl)imidazo[1,2-a]pyridin-3-yl)pentan-1-one | $^1$H NMR (400 MHz, DMSO-d$_6$) δ 9.55 (br s, 1H), 7.51 (dd, J = 9.0, 1.8 Hz, 1H), 7.42-7.39 (m, 1H), 7.36-7.31 (m, 1H), 7.26-7.21 (m, 1H), 7.16 (d, J = 7.2 Hz, 1H), 6.44 (br s, 2H), 2.77 (t, J = 7.0 Hz, 3H), 2.17 (d, J = 2.8 Hz, 3H), 1.65-1.57 (m, 2H), 1.41-1.30 (m, 1H), 0.906 (t, J = 7.4 Hz, 3H); LCMS (electrospray) m/z 326.15 (M + H)+. | B |
| 24 | (2-((2-(dimethylamino)ethyl)amino)-6-(3-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.77 (s, 1H), 8.22-8.09 (m, 2H), 7.44-7.40 (m, 1H), 7.35-7.28 (m, 1H), 7.24-7.12 (m, 1H), 5.37-5.16 (m, 1H), 4.54 (s, 2H), 4.09 (d, J = 4.9 Hz, 2H), 3.17 (d, J = 3.8 Hz, 6H), 2.83-2.66 (m, 4H), 2.33-2.08 (m, 3H), 1.96 (dtd, J = 23.5, 6.8, 3.2 Hz, 1H), 1.33-1.23 (m, 1H); LCMS (electrospray) m/z 399.2 (M + H)+. | C |

TABLE 1-continued

Compounds of Examples

| Ex # | Structure/Name | 1H NMR/MS (M + 1) | Synthetic Method |
|---|---|---|---|
| 25 | 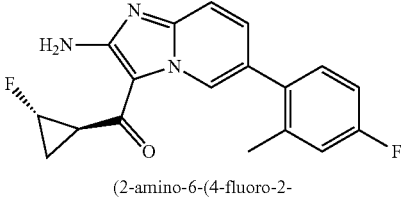<br>(2-amino-6-(4-fluoro-2-methylphenyl)imidazo[1,2-a]pyridin-3-yl)((1R,2S)-2-fluorocyclopropyl)methanone | $^1$H NMR (400 MHz, DMSO-d$_6$) δ 9.41 (s, 1H), 7.52 (dd, J = 2.0, 8.8 Hz, 1H), 7.41 (d, J = 8.4 Hz, 1H), 7.31 (dd, J = 6.4, 8.0 Hz, 1H), 7.21 (dd, J = 2.8, 10.4 Hz, 1H), 7.12 (dt, J = 2.8, 8.0 Hz, 1H), 6.66 (s, 2H), 5.10-4.88 (m, 1H), 3.11-3.00 (m, 1H), 2.28 (s, 3H), 1.67-1.53 (m, 1H), 1.40-1.29 (m, 1H); LCMS (electrospray) m/z 328.10 (M + H)+. | B |
| 26 | 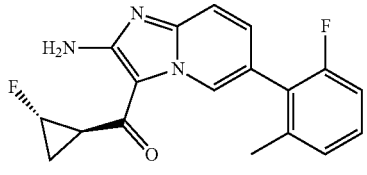<br>(2-amino-6-(2-fluoro-2-methylphenyl)imidazo[1,2-a]pyridin-3-yl)((1R,2S)-2-fluorocyclopropyl)methanone | $^1$H NMR (400 MHz, DMSO-d$_6$) δ 9.41 (s, 1H), 7.46 (s, 2H), 7.40-7.33 (m, 1H), 7.24-7.12 (m, 2H), 6.69 (s, 2H), 5.10-4.89 (m, 1H), 3.11-2.99 (m, 1H), 2.17 (s, 3H), .1.66-1.54 (m, 1H), 1.39-1.29 (m, 1H); LCMS (electrospray) m/z 328.10 (M + H)+. | B |
| 27 | 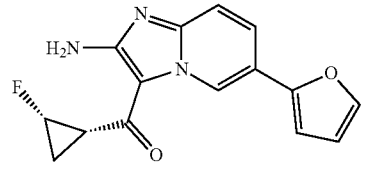<br>(2-amino-6-(furan-2-yl)imidazo[1,2-a]pyridin-3-yl)((1S,2S)-2-fluorocyclopropyl)methanone | $^1$H NMR (400 MHz, DMSO-d$_6$) δ 9.90 (s, 1H), 7.85 (dd, J = 2.0, 8.8 Hz, 1H), 7.77 (d, J = 1.2 Hz, 1H), 7.42 (d, J = 8.0 Hz, 1H), 6.96 (d, J = 3.6 Hz, 1H), 6.67 (s, 2H), 6.62 (dd, J = 1.6, 3.2 Hz, 1H), 5.29-5.05 (m, 1H), 2.63-2.53 (m, 1H), 1.95-1.81 (m, 1H), 1.18-1.07 (m, 1H); LCMS (electrospray) m/z 286.10 (M + H)+. | B |
| 28 | 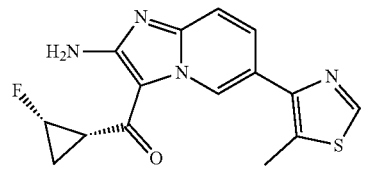<br>(2-amino-6-(5-methylthiazol-4-yl)imidazo[1,2-a]pyridin-3-yl)((1S,2S)-2-fluorocyclopropyl)methanone | $^1$H NMR (400 MHz, DMSO-d$_6$) δ 10.01-9.88 (m, 1H), 8.99 (br d, J = 0.9 Hz, 1H), 7.91-7.84 (m, 1H), 7.44 (br d, J = 9.0 Hz, 1H), 6.68 (br s, 2H), 5.29-5.07 (m, 1H), 2.68-2.58 (m, 5H), 1.93-1.84 (m, 1H), 1.20-1.08 (m, 1H); LCMS (electrospray) m/z 317.20 (M + H)+. | D |
| 29 | 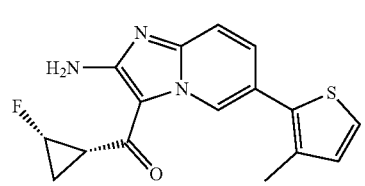<br>(2-amino-6-(3-methylthiophen-2-yl)imidazo[1,2-a]pyridin-3-yl)((1S,2S)-2-fluorocyclopropyl)methanone | $^1$H NMR (400 MHz, DMSO-d$_6$) δ 9.75-9.65 (m, 1H), 7.60 (dd, J = 1.9, 9.1 Hz, 1H), 7.51 (d, J = 5.1 Hz, 1H), 7.43 (dd, J = 0.7, 9.0 Hz, 1H), 7.04 (d, J = 5.1 Hz, 1H), 6.75-6.64 (m, 2H), 5.31-5.05 (m, 1H), 2.62-2.55 (m, 1H), 2.30 (s, 3H), 1.95-1.79 (m, 1H), 1.01 (s, 1H); LCMS (electrospray) m/z 316.20 (M + H)+. | D |

TABLE 1-continued

Compounds of Examples

| Ex # | Structure/Name | 1H NMR/MS (M + 1) | Synthetic Method |
|---|---|---|---|
| 30 | 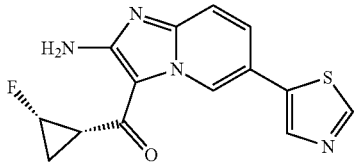<br>(2-amino-6-(thiazol-5-yl)imidazo[1,2-a]pyridin-3-yl)((1S,2S)-2-fluorocyclopropyl)methanone | $^1$H NMR (400 MHz, DMSO-d$_6$) δ 9.76 (s, 1H), 9.06 (s, 1H), 8.26 (s, 1H), 7.86 (dd, J12 = 1.8 Hz, J13 = 9.0 Hz, 1H), 7.42 (d, J = 9.6 Hz, 1H), 6.72 (s, 2H), 5.09-4.92 (m, 1H), 3.07-2.99 (m, 1H), 1.63-1.53 (m, 1H), 1.37-1.32 (m, 1H); LCMS (electrospray) m/z 303.00 (M + H)+. | D |
| 31 | 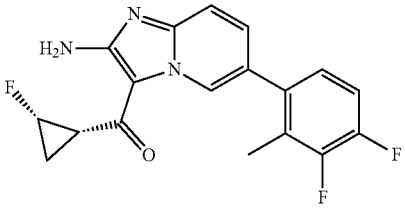<br>(2-amino-6-(3,4-difluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.50 (s, 1H), 7.52 (dd, J = 1.6, 8.8 Hz, 1H), 7.43 (d, J = 8.4 Hz, 1H), 7.37 (q, J = 8.4 Hz, 1H), 7.19 (m, 1H), 6.68 (s, 2H), 5.29-5.05 (m, 1H), 2.64-2.53 (m, 1H), 2.21 (d, J = 3.2 Hz, 3H), 1.91-1.77 (m, 1H), 1.16-1.04 (m, 1H); LCMS (electrospray) m/z 346.10 (M + H)+. | B |
| 32 | 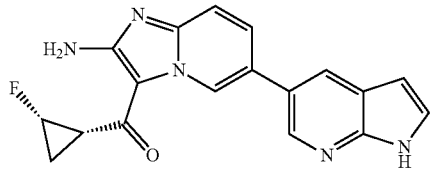<br>(2-amino-6-(1H-pyrrolo[2,3-b]pyridin-5-yl)imidazo[1,2-a]pyridin-3-yl)((1S,2S)-2-fluorocyclopropyl)methanone | $^1$H NMR (400 MHz, DMSO-d$_6$) δ 11.77 (s, 1H), 9.84 (s, 1H), 8.48 (d, J = 2.0 Hz, 1H), 8.21 (d, J = 1.6 Hz, 1H), 7.89 (dd, J = 1.6, 8.8 Hz, 1H), 7.54 (t, J = 3.2 Hz, 1H), 7.47 (d, J = 9.2 Hz, 1H), 6.65 (s, 2H), 6.54 (q, J = 1.6 Hz, 1H), 5.32-5.07 (m, 1H), 2.69-2.56 (m, 1H), 1.95-1.82 (m, 1H), 1.16-1.07 (m, 1H); LCMS (electrospray) m/z 336.10 (M + H)+. | L |
| 33 | 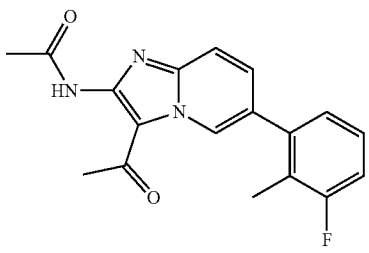<br>N-(3-acetyl-6-(3-fluoro-2-methylphenyl)imidazo[1,2-a]pyridin-2-yl)acetamide | $^1$H NMR (400 MHz, DMSO-d$_6$) δ 10.50 (s, 1H), 9.50 (s, 1H), 7.81 (d, J = 9.2 Hz, 1H), 7.68 (dd, J = 2.4, 9.6 Hz, 1H), 7.37 (m, 1H), 7.27 (t, J = 8.0 Hz, 1H), 7.20 (d, J = 7.6 Hz, 1H), 2.44 (s, 3H), 2.17 (d, J = 2.4 Hz, 3H), 2.15 (s, 3H); LCMS (electrospray) m/z 326.10 (M + H)+. | E |
| 34 | 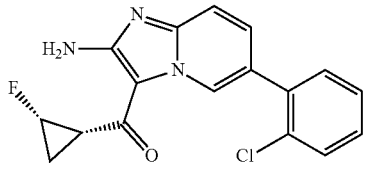<br>(2-amino-6-(2-chlorophenyl)imidazo[1,2-a]pyridin-3-yl)((1S,2S)-2-fluorocyclopropyl)methanone | $^1$H NMR (400 MHz, DMSO-d$_6$) δ 9.59 (s, 1H), 7.61-7.54 (m, 2H), 7.50-7.46 (m, 1H), 7.45-7.39 (m, 3H), 6.66 (s, 2H), 5.24-5.04 (m, 1H), 2.58-2.51 (m, 1H), 1.85-1.75 (m, 1H), 1.11-1.02 (m, 1H); LCMS (electrospray) m/z 330.10 (M + H)+. | B |

TABLE 1-continued

Compounds of Examples

| Ex # | Structure/Name | 1H NMR/MS (M + 1) | Synthetic Method |
|---|---|---|---|
| 35 | 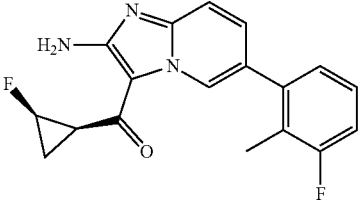<br>(2-amino-6-(3-fluoro-2-methylphenyl)imidazo[1,2-a]pyridin-3-yl)((1S,2S)-2-fluorocyclopropyl)methanone | $^1$H NMR (400 MHz, DMSO-$d_6$) δ 9.48 (s, 1H), 7.50 (dd, J = 9.1, 1.9 Hz, 1H), 7.39 (d, J = 9.9 Hz, 1H), 7.32-7.27 (m, 1H), 7.22-7.12 (m, 2H), 6.64 (s, 2H), 5.23-5.03 (m, 1H), 2.58-2.51 (m, 1H), 2.13 (d, J = 2.7 Hz, 3H), 1.85-1.75 (m, 1H), 1.10-1.02 (m, 1H); LCMS (electrospray) m/z 328.10 (M + H)+. | B |
| 36 | 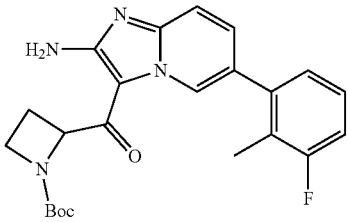<br>tert-butyl 2-(2-amino-6-(3-fluoro-2-methylphenyl)imidazo[1,2-a]pyridine-3-carbonyl)azetidine-1-carboxylate | $^1$H NMR (400 MHz, DMSO-$d_6$) δ 9.57 (br s, 1H), 7.56 (dd, J = 8.8, 1.6 Hz, 1H), 7.43 (d, J = 8.8 Hz, 1H), 7.37-7.32 (m, 1H), 7.24 (t, J = 9.0 Hz, 1H), 7.17 (d, J = 8.0 Hz, 1H), 6.59-6.53 (m, 2H), 5.36-5.33 (m, 1H), 3.84-3.73 (m, 2H), 2.77-2.61 (m, 1H), 2.17 (d, J = 2.4 Hz, 3H), 2.03-1.94 (m, 1H), 1.38 (s, 4.5H), 1.22 (s, 4.5H); LCMS (electrospray) m/z 425.2 (M + H)+. | B |
| 37 | 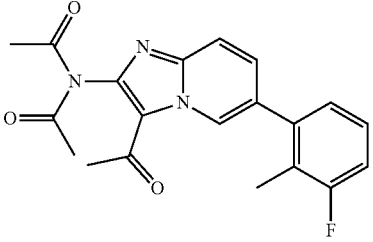<br>N-acetyl-N-(3-acetyl-6-(3-fluoro-2-methylphenyl)imidazo[1,2-a]pyridin-2-yl)acetamide | $^1$H NMR (400 MHz, DMSO-$d_6$) δ 9.57 (d, J = 1.1 Hz, 1H), 7.99-7.91 (m, 1H), 7.80 (dd, J = 9.1, 1.9 Hz, 1H), 7.44-7.35 (m, 1H), 7.34-7.26 (m, 1H), 7.23 (d, J = 7.7 Hz, 1H), 2.37 (s, 3H), 2.35 (s, 6H), 2.20 (d, J = 2.7 Hz, 3H); LCMS (electrospray) m/z 368.10 (M + H)+. | E |
| 38 | 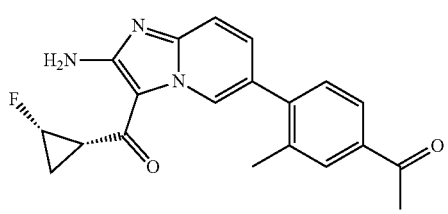<br>1-(4-(2-amino-3-((1S,2S)-2-fluorocyclopropane-1-carbonyl)imidazo[1,2-a]pyridin-6-yl)-3-methylphenyl)ethan-1-one | $^1$H NMR (400 MHz, DMSO-$d_6$) δ 9.91 (s, 1H), 8.01-7.84 (m, 2H), 7.66-7.55 (m, 2H), 7.47 (d, J = 9.9 Hz, 1H), 6.72 (s, 2H), 5.33-5.05 (m, 1H), 2.58 (d, J = 8.2 Hz, 3H), 2.53 (s, 3H), 1.96-1.80 (m, 1H), 1.16-1.05 (m, 1H); LCMS (electrospray) m/z 352.10 (M + H)+. | B |

TABLE 1-continued

Compounds of Examples

| Ex # | Structure/Name | 1H NMR/MS (M + 1) | Synthetic Method |
|---|---|---|---|
| 39 | (2-amino-6-(4-morpholinophenyl)imidazo[1,2-a]pyridin-3-yl)((1S,2S)-2-fluorocyclopropyl)methanone | $^1$H NMR (400 MHz, DMSO-$d_6$) δ 9.79 (s, 1H), 7.79 (dd, J = 9.1, 1.9 Hz, 1H), 7.53 (d, J = 8.2 Hz, 2H), 7.41 (d, J = 8.8 Hz, 1H), 7.06 (d, J = 8.8 Hz, 2H), 6.61 (s, 2H), 5.31-5.04 (m, 1H), 3.76 (t, J = 4.9 Hz, 4H), 3.17 (t, J = 4.7 Hz, 4H), 2.65-2.53 (m, 1H), 1.95-1.80 (m, 1H), 1.15-1.05 (m, 1H); LCMS (electrospray) m/z 381.10 (M + H)+. | B |
| 40 | (2-amino-6-(4-methyl-1H-pyrrolo[2,3-b]pyridin-5-yl)imidazo[1,2-a]pyridin-3-yl)((1S,2S)-2-fluorocyclopropyl)methanone | $^1$H NMR (400 MHz, DMSO-$d_6$) δ 11.70 (s, 1H), 9.53 (s, 1H), 8.11 (s, 1H), 7.59 (dd, J = 8.8, 1.6 Hz, 1H), 7.50 (t, J = 3.0 Hz, 1H), 7.44 (d, J = 8.8 Hz, 1H), 6.65 (s, 2H), 6.58 (q, J = 1.8 Hz, 1H), 5.30-5.05 (m, 1H), 2.65-2.53 (m, 1H), 2.47 (s, 3H), 1.91-1.77 (m, 1H), 1.16-1.04 (m, 1H); LCMS (electrospray) m/z 350.10 (M + H)+. | L |
| 41 | (2-amino-6-(4-chloro-1H-pyrrolo[2,3-b]pyridin-5-yl)imidazo[1,2-a]pyridin-3-yl)((1S,2S)-2-fluorocyclopropyl)methanone | $^1$H NMR (400 MHz, DMSO-$d_6$) δ 12.18 (s, 1H), 9.66 (s, 1H), 8.29 (s, 1H), 7.73-7.60 (m, 2H), 7.47 (d, J = 9.3 Hz, 1H), 6.70 (s, 2H), 6.58 (q, J = 1.8 Hz, 1H), 5.32-5.02 (m, 1H), 2.65-2.54 (m, 1H), 1.92-1.74 (m, 1H), 1.18-1.03 (m, 1H); LCMS (electrospray) m/z 370.10 (M + H)+. | L |
| 42 | (2-amino-6-(3-fluoro-2-methylphenyl)imidazo[1,2-a]pyridin-3-yl)((1S,2R)-2-fluorocyclopropyl)methanone | $^1$H NMR (400 MHz, DMSO-$d_6$) δ 9.42 (s, 1H), 7.51 (dd, J = 9.1, 1.9 Hz, 1H), 7.40-7.38 (m, 1H), 7.31-7.26 (m, 1H), 7.19 (t, J = 9.1 Hz, 1H), 7.11 (d, J = 7.7 Hz, 1H), 6.65 (s, 2H), 5.04-4.87 (m, 1H), 3.06-2.97 (m, 1H), 2.12 (d, J = 2.7 Hz, 3H), 1.60-1.53 (m, 1H), 1.33-1.28 (m, 1H); LCMS (electrospray) m/z 328.10 (M + H)+. | B |

TABLE 1-continued

Compounds of Examples

| Ex # | Structure/Name | 1H NMR/MS (M + 1) | Synthetic Method |
|---|---|---|---|
| 43 | 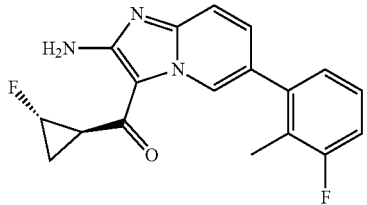<br>(2-amino-6-(3-fluoro-2-methylphenyl)imidazo[1,2-a]pyridin-3-yl)((1R,2S)-2-fluorocyclopropyl)methanone | $^1$H NMR (400 MHz, DMSO-$d_6$) δ 9.42 (s, 1H), 7.51 (dd, J = 9.1, 1.9 Hz, 1H), 7.40-7.38 (m, 1H), 7.31-7.26 (m, 1H), 7.19 (t, J = 9.1 Hz, 1H), 7.11 (d, J = 7.7 Hz, 1H), 6.65 (s, 2H), 5.04-4.87 (m, 1H), 3.06-2.97 (m, 1H), 2.12 (d, J = 2.7 Hz, 3H), 1.60-1.53 (m, 1H), 1.33-1.28 (m, 1H); LCMS (electrospray) m/z 328.10 (M + H)+. | B |
| 44 | 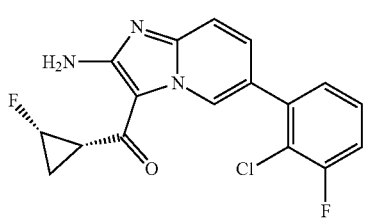<br>(2-amino-6-(2-chloro-3-fluorophenyl)imidazo[1,2-a]pyridin-3-yl)((1S,2S)-2-fluorocyclopropyl)methanone | $^1$H NMR (400 MHz, DMSO-$d_6$) δ 9.62 (s, 1H), 7.58 (dd, J = 9.1, 1.9 Hz, 1H), 7.48-7.41 (m, 4H), 7.37-7.34 (m, 1H), 6.69 (s, 2H), 5.24-5.04 (m, 1H), 2.57-2.51 (m, 2H), 1.85-1.77 (m, 1H), 1.10-1.04 (m, 1H); LCMS (electrospray) m/z 348.05 (M + H)+. | B |
| 45 | 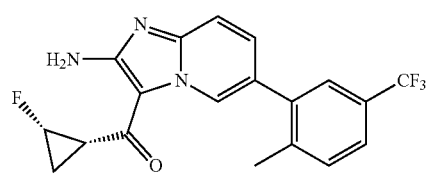<br>(2-amino-6-(2-methyl-5-(trifluoromethyl)phenyl)imidazo[1,2-a]pyridin-3-yl)((1S,2S)-2-fluorocyclopropyl)methanone | $^1$H NMR (400 MHz, DMSO-$d_6$) δ 9.50 (s, 1H), 7.66-7.64 (m, 1H), 7.59 (s, 1H), 7.56-7.53 (m, 2H), 7.40 (d, J = 8.0 Hz, 1H), 6.65 (s, 2H), 5.23-5.03 (m, 1H), 2.56-2.51 (m, 1H), 2.30 (d, J = 6.6 Hz, 3H), 1.86-1.75 (m, 1H), 1.11-1.02 (m, 1H); LCMS (electrospray) m/z 378.10 (M + H)+. | B |
| 46 | 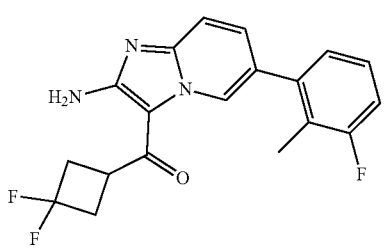<br>(2-amino-6-(3-fluoro-2-methylphenyl)imidazo[1,2-a]pyridin-3-yl)(3,3-difluorocyclobutyl)methanone | $^1$H NMR (400 MHz, DMSO-$d_6$) δ 9.60 (br s, 1H), 7.56 (dd, J = 9.0, 1.8 Hz, 1H), 7.43 (d, J = 8.8 Hz, 1H), 7.37-7.32 (m, 1H), 7.27-7.22 (m, 1H), 7.17 (d, J = 7.6 Hz, 1H), 6.57 (br s, 2H), 3.76-3.72 (m, 1H), 3.01-2.80 (m, 4H), 2.17 (d, J = 2.0 Hz, 3H); LCMS (electrospray) m/z 360.1 (M + H)+. | B |
| 47 | 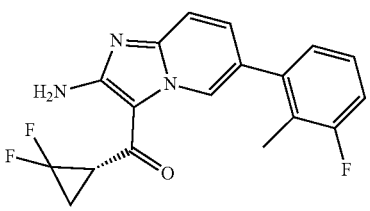<br>(S)-(2-amino-6-(3-fluoro-2-methylphenyl)imidazo[1,2-a]pyridin-3-yl)(2,2-difluorocyclopropyl)methanone | $^1$H NMR (400 MHz, DMSO-$d_6$) δ 9.50 (br s, 1H), 7.59 (dd, J = 1.6, 8.8 Hz, 1H), 7.47-7.44 (m, 1H), 7.36-7.31 (m, 1H), 7.26-7.21 (m, 1H), 7.17 (d, J = 7.2 Hz, 1H), 6.62 (br s, 2H), 3.75-3.67 (m, 1H), 2.17-2.10 (m, 4H), 1.94-1.85 (m, 1H); LCMS (electrospray) m/z 346.10 (M + H)+. | B |

TABLE 1-continued

Compounds of Examples

| Ex # | Structure/Name | 1H NMR/MS (M + 1) | Synthetic Method |
|---|---|---|---|
| 48 | 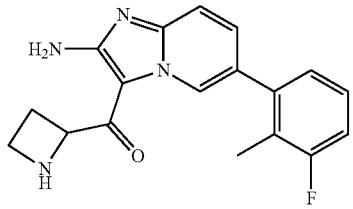<br>(2-amino-6-(3-fluoro-2-methylphenyl)imidazo[1,2-a]pyridin-3-yl)(azetidin-2-yl)methanone | $^1$H NMR (400 MHz, DMSO-d$_6$) δ 9.58 (br s, 1H), 7.54 (dd, J = 1.8, 9.0 Hz, 1H), 7.42-7.39 (m, 1H), 7.37-7.31 (m, 1H), 7.26-7.22 (m, 1H), 7.17 (d, J = 8.0 Hz, 1H), 6.95 (br s, 2H), 4.67-4.64 (m, 1H), 3.76 (br s, 1H), 3.43-3.33 (m, 2H), 2.77-2.66 (m, 1H), 2.17 (d, J = 2.4 Hz, 3H); LCMS (electrospray) m/z 325.10 (M + H)+. | B |
| 49 | 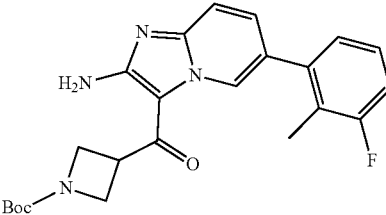<br>tert-butyl 3-(2-amino-6-(3-fluoro-2-methylphenyl)imidazo[1,2-a]pyridine-3-carbonyl)azetidine-1-carboxylate | $^1$H NMR (400 MHz, DMSO-d$_6$) δ 9.60 (br s, 1H), 7.55 (dd, J = 9.2, 2.0 Hz, 1H), 7.42 (d, J = 8.8 Hz, 1H), 7.37-7.31 (m, 1H), 7.24 (t, J = 9.2 Hz, 1H), 7.17 (d, J = 8.0 Hz, 1H), 6.49 (s, 2H), 4.11-3.99 (m, 5H), 2.17 (d, J = 2.0 Hz, 3H), 1.37 (s, 9H); LCMS (electrospray) m/z 425.2 (M + H)+. | B |
| 50 | 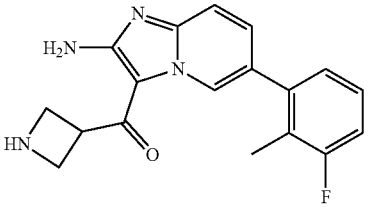<br>(2-amino-6-(3-fluoro-2-methylphenyl)imidazo[1,2-a]pyridin-3-yl)(azetidin-2-yl)methanone | $^1$H NMR (400 MHz, DMSO-d$_6$) δ 9.58 (br s, 1H), 7.52 (dd, J = 9.2, 2.0 Hz, 1H), 7.40 (d, J = 8.4 Hz, 1H), 7.37-7.31 (m, 1H), 7.24 (t, J = 8.8 Hz, 1H), 7.17 (d, J = 7.6 Hz, 1H), 6.38 (s, 2H), 4.20-4.13 (m, 1H), 3.73-3.67 (m, 4H), 2.17 (d, J = 2.4 Hz, 3H); LCMS (electrospray) m/z 325.10 (M + H)+. | B |
| 51 | 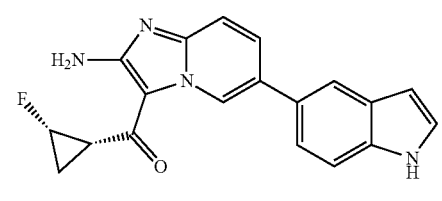<br>(2-amino-6-(1H-indol-5-yl)imidazo[1,2-a]pyridin-3-yl)((1S,2S)-2-fluorocyclopropyl)methanone | $^1$H NMR (400 MHz, DMSO-d$_6$) δ 11.21 (s, 1H), 9.86 (s, 1H), 7.86 (dd, J = 9.1, 1.9 Hz, 1H), 7.81 (d, J = 1.6 Hz, 1H), 7.51 (d, J = 8.8 Hz, 1H), 7.48-7.39 (m, 2H), 7.37 (dd, J = 8.5, 1.9 Hz, 1H), 6.62 (s, 2H), 6.52 (t, J = 1.9 Hz, 1H), 5.36-5.01 (m, 1H), 2.60 (t, J = 7.1 Hz, 1H), 1.96-1.78 (m, 1H), 1.16-1.02 (m, 1H); LCMS (electrospray) m/z 335.10 (M + H)+. | L |
| 52 | 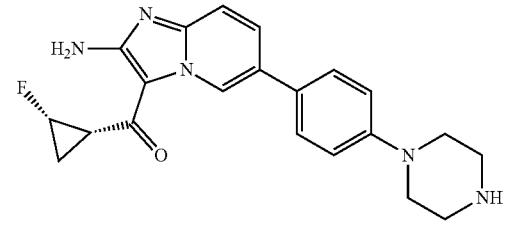<br>(2-amino-6-(4-(piperazin-1-yl)phenyl)imidazo[1,2-a]pyridin-3-yl)((1S,2S)-2-fluorocyclopropyl)methanone | $^1$H NMR (400 MHz, DMSO-d$_6$) δ 9.78 (s, 1H), 7.79 (dd, J = 9.1, 1.9 Hz, 1H), 7.51 (d, J = 8.8 Hz, 2H), 7.41 (d, J = 8.8 Hz, 1H), 7.05 (d, J = 8.8 Hz, 2H), 6.61 (s, 2H), 5.17 (d, J = 67.1 Hz, 1H), 3.25-3.08 (m, 4H), 3.04-2.83 (m, 4H), 2.66-2.54 (m, 1H), 1.95-1.79 (m, 1H), 1.18-1.02 (m, 1H); LCMS (electrospray) m/z 380.20 (M + H)+. | B |

TABLE 1-continued

Compounds of Examples

| Ex # | Structure/Name | 1H NMR/MS (M + 1) | Synthetic Method |
|---|---|---|---|
| 53 | (2-amino-6-(4-(4-methylpiperazin-1-yl)phenyl)imidazo[1,2-a]pyridin-3-yl)((1S,2S)-2-fluorocyclopropyl)methanone | $^1$H NMR (400 MHz, DMSO-$d_6$) δ 9.78 (s, 1H), 7.79 (dd, J = 9.3, 2.2 Hz, 1H), 7.50 (d, J = 8.8 Hz, 2H), 7.40 (d, J = 8.8 Hz, 1H), 7.05 (d, J = 8.8 Hz, 2H), 6.63 (dd, J = 9.9, 3.3 Hz, 2H), 5.31-5.05 (m, 1H), 3.27-3.10 (m, 4H), 2.59 (m, 1H), 2.48-2.35 (m, 4H), 2.30-2.17 (m, 3H), 1.96-1.79 (m, 1H), 1.18-1.05 (m, 1H); LCMS (electrospray) m/z 394.20 (M + H)+. | B |
| 54 | (6-(3-fluoro-2-methylphenyl)-2-(methylamino)imidazo[1,2-a]pyridin-3-yl)((1S,2S)-2-fluorocyclopropyl)methanone | $^1$H NMR (400 MHz, DMSO-$d_6$) δ 9.56 (s, 1H), 7.59-7.53 (m, 3H), 7.35 (dd, J = 13.7, 8.2 Hz, 1H), 7.27-7.18 (m, 3H), 5.28-5.08 (m, 1H), 4.80 (s, 1H), 3.07 (d, J = 4.4 Hz, 3H), 2.31 (d, J = 18.7 Hz, 1H), 2.18 (d, J = 2.2 Hz, 3H), 1.91-1.76 (m, 1H), 1.48 (s, 1H), 1.17-1.08 (m, 1H); LCMS (electrospray) m/z 342.10 (M + H)+. | F |
| 55 | (2-(dimethylamino)-6-(3-fluoro-2-methylphenyl)imidazo[1,2-a]pyridin-3-yl)((1R,2S)-2-fluorocyclopropyl)methanone | $^1$H NMR (400 MHz, DMSO-$d_6$) δ 9.49 (t, J = 1.4 Hz, 1H), 7.70-7.63 (m, 2H), 7.35 (dd, J = 13.7, 8.2 Hz, 1H), 7.26 (t, J = 8.5 Hz, 1H), 7.16 (d, J = 7.7 Hz, 1H), 5.02 (dd, J = 67.3, 1.9 Hz, 1H), 3.07 (d, J = 12.6 Hz, 6H), 2.16 (d, J = 2.2 Hz, 3H), 1.73-1.63 (m, 1H), 1.50 (td, J = 12.9, 6.4 Hz, 1H); LCMS (electrospray) m/z 356.10 (M + H)+. | G |
| 56 | (2-amino-6-(3-(4-methylpiperazin-1-yl)phenyl)imidazo[1,2-a]pyridin-3-yl)((1S,2S)-2-fluorocyclopropyl)methanone | $^1$H NMR (400 MHz, DMSO-$d_6$) δ 9.80 (s, 1H), 7.83 (dd, J = 9.1, 1.9 Hz, 1H), 7.42 (d, J = 9.3 Hz, 1H), 7.32 (t, J = 8.0 Hz, 1H), 7.13 (s, 1H), 7.08-6.92 (m, 2H), 6.65 (s, 2H), 5.35-5.01 (m, 1H), 3.28-3.13 (m, 4H), 2.66-2.53 (m, 1H), 2.49-2.42 (m, 4H), 2.23 (s, 3H), 1.96-1.79 (m, 1H), 1.16-1.04 (m, 1H); LCMS (electrospray) m/z 394.20 (M + H)+. | B |

TABLE 1-continued

Compounds of Examples

| Ex # | Structure/Name | 1H NMR/MS (M + 1) | Synthetic Method |
|---|---|---|---|
| 57 | (2-amino-6-(1H-indol-4-yl)imidazo[1,2-a]pyridin-3-yl)((1S,2S)-2-fluorocyclopropyl)methanone | $^1$H NMR (400 MHz, DMSO-d$_6$) δ 11.36 (s, 1H), 9.96 (s, 1H), 7.84 (dd, J = 9.1, 1.9 Hz, 1H), 7.58-7.41 (m, 3H), 7.27-7.11 (m, 2H), 6.75-6.53 (m, 3H), 5.35-4.99 (m, 1H), 2.66-2.55 (m, 1H), 1.94-1.80 (m, 1H), 1.15-1.03 (m, 1H); LCMS (electrospray) m/z 335.10 (M + H)+. | L |
| 58 | (2-amino-6-(1H-indol-6-yl)imidazo[1,2-a]pyridin-3-yl)((1S,2S)-2-fluorocyclopropyl)methanone | $^1$H NMR (400 MHz, DMSO-d$_6$) δ 11.21 (s, 1H), 9.90 (s, 1H), 7.87 (dd, J = 9.3, 1.6 Hz, 1H), 7.66 (d, J = 8.2 Hz, 2H), 7.53-7.36 (m, 2H), 7.29 (d, J = 8.2 Hz, 1H), 6.64 (s, 2H), 6.47 (s, 1H), 5.33-5.04 (m, 1H), 2.77-2.55 (m, 1H), 2.00-1.79 (m, 1H), 1.18-1.02 (m, 1H); LCMS (electrospray) m/z 335.10 (M + H)+. | L |
| 59 | (2-amino-6-(1H-indol-7-yl)imidazo[1,2-a]pyridin-3-yl)((1S,2S)-2-fluorocyclopropyl)methanone | $^1$H NMR (400 MHz, DMSO-d$_6$) δ 11.15 (s, 1H), 9.80 (s, 1H), 7.72 (dd, J = 9.1, 1.9 Hz, 1H), 7.60 (t, J = 4.4 Hz, 1H), 7.49 (d, J = 9.3 Hz, 1H), 7.36 (t, J = 2.7 Hz, 1H), 7.21-7.03 (m, 2H), 6.65 (s, 2H), 6.55 (s, 1H), 5.34-5.02 (m, 1H), 2.65-2.54 (m, 1H), 1.93-1.77 (m, 1H), 1.16-1.02 (m, 1H); LCMS (electrospray) m/z 335.10 (M + H)+. | L |
| 60 | (2-amino-6-(6-fluoro-5-methyl-1H-indazol-4-yl)imidazo[1,2-a]pyridin-3-yl)((1S,2S)-2-fluorocyclopropyl)methanone | $^1$H NMR (400 MHz, DMSO-d$_6$) δ 13.21 (s, 1H), 9.62 (s, 1H), 7.78 (s, 1H), 7.60 (dd, J = 8.8, 1.6 Hz, 1H), 7.51 (d, J = 8.8 Hz, 1H), 7.40 (d, J = 9.9 Hz, 1H), 6.72 (s, 2H), 5.34-5.00 (m, 1H), 2.64-2.54 (m, 1H), 2.29-2.13 (m, 3H), 1.91-1.74 (m, 1H), 1.18-1.00 (m, 1H); LCMS (electrospray) m/z 368.10 (M + H)+. | L |

TABLE 1-continued

Compounds of Examples

| Ex # | Structure/Name | 1H NMR/MS (M + 1) | Synthetic Method |
|---|---|---|---|
| 61 | 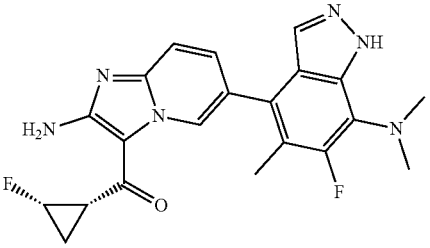<br>(2-amino-6-(7-(dimethylamino)-6-fluoro-5-methyl-1H-indazol-4-yl)imidazo[1,2-a]pyridin-3-yl)((1S,2S)-2-fluorocyclopropyl)methanone | $^1$H NMR (400 MHz, DMSO-d$_6$) δ 13.23 (s, 1H), 9.57 (s, 1H), 7.73 (s, 1H), 7.55 (dd, J = 8.8, 1.6 Hz, 1H), 7.48 (d, J = 8.8 Hz, 1H), 6.70 (s, 2H), 5.30-5.03 (m, 1H), 2.95 (d, J = 2.2 Hz, 6H), 2.64-2.53 (m, 1H), 2.17 (s, 3H), 1.90-1.75 (m, 1H), 1.17-1.01 (m, 1H); LCMS (electrospray) m/z 411.15 (M + H)+. | L |
| 62 | 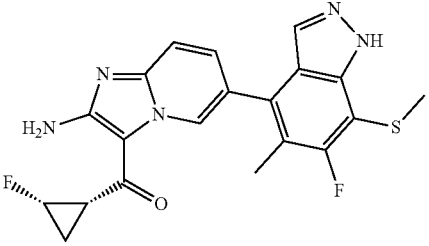<br>(2-amino-6-(6-fluoro-5-methyl-7-(methylthio)-1H-indazol-4-yl)imidazo[1,2-a]pyridin-3-yl)((1S,2S)-2-fluorocyclopropyl)methanone | $^1$H NMR (400 MHz, DMSO-d$_6$) δ 13.50 (s, 1H), 9.61 (s, 1H), 7.85 (s, 1H), 7.59 (dd, J = 8.8, 1.6 Hz, 1H), 7.51 (d, J = 9.3 Hz, 1H), 6.73 (s, 2H), 5.36-4.99 (m, 1H), 2.64-2.54 (m, 1H), 2.52 (s, 3H), 2.22 (d, J = 2.7 Hz, 3H), 1.91-1.73 (m, 1H), 1.17-0.99 (m, 1H); LCMS (electrospray) m/z 414.10 (M + H)+. | L |
| 63 | 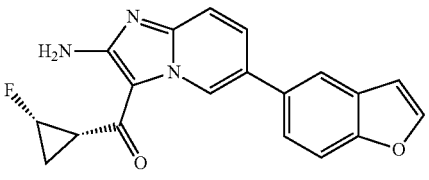<br>(2-amino-6-(benzofuran-5-yl)imidazo[1,2-a]pyridin-3-yl)((1S,2S)-2-fluorocyclopropyl)methanone | $^1$H NMR (400 MHz, DMSO-d$_6$) δ 9.88 (s, 1H), 8.06 (d, J = 2.2 Hz, 1H), 7.93 (s, 1H), 7.87 (dd, J = 9.1, 1.9 Hz, 1H), 7.72 (d, J = 8.8 Hz, 1H), 7.58 (dd, J = 8.5, 1.9 Hz, 1H), 7.46 (d, J = 8.8 Hz, 1H), 7.04 (d, J = 2.5 Hz, 1H), 6.67 (s, 2H), 5.27-5.10 (m, 1H), 2.61-2.61 (m, 1H), 1.91-1.84 (m, 1H), 1.15-1.08 (m, 1H); LCMS (electrospray) m/z 336.10 (M + H)+. | L |
| 64 | <br>(2-amino-6-(5-chloro-6-fluoro-1H-indazol-4-yl)imidazo[1,2-a]pyridin-3-yl)((1S,2S)-2-fluorocyclopropyl)methanone | $^1$H NMR (400 MHz, DMSO-d$_6$) δ 13.51 (s, 1H), 9.74 (s, 1H), 7.93 (s, 1H), 7.68 (dd, J = 9.1, 1.9 Hz, 2H), 7.53 (d, J = 8.8 Hz, 1H), 6.76 (s, 2H), 5.16 (d, J = 67.1 Hz, 1H), 2.59 (t, J = 6.6 Hz, 1H), 1.89-1.63 (m, 1H), 1.18-0.94 (m, 1H); LCMS (electrospray) m/z 388.05 (M + H)+. | L |

TABLE 1-continued

Compounds of Examples

| Ex # | Structure/Name | 1H NMR/MS (M + 1) | Synthetic Method |
|---|---|---|---|
| 65 | 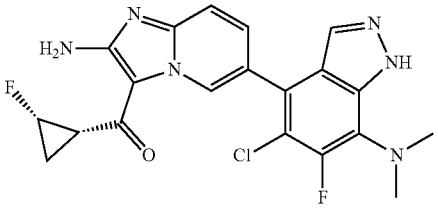<br>(2-amino-6-(5-chloro-7-(dimethylamino)-6-fluoro-1H-indazol-4-yl)imidazo[1,2-a]pyridin-3-yl)((1S,2S)-2-fluorocyclopropyl)methanone | $^1$H NMR (400 MHz, DMSO-$d_6$) δ 13.53 (s, 1H), 9.68 (s, 1H), 7.88 (s, 1H), 7.64 (d, J = 8.8 Hz, 1H), 7.51 (d, J = 8.8 Hz, 1H), 6.73 (s, 2H), 5.37-4.97 (m, 1H), 3.00 (s, 6H), 2.63-2.53 (m, 1H), 1.91-1.66 (m, 1H), 1.16-0.97 (m, 1H); LCMS (electrospray) m/z 431.10 (M + H)+. | L |
| 66 | 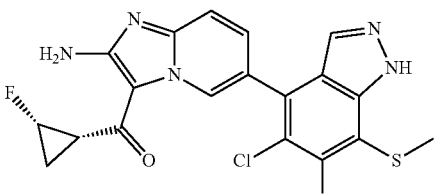<br>(2-amino-6-(5-chloro-6-fluoro-7-(methylthio)-1H-indazol-4-yl)imidazo[1,2-a]pyridin-3-yl)((1S,2S)-2-fluorocyclopropyl)methanone | $^1$H NMR (400 MHz, DMSO-$d_6$) δ 13.82 (s, 1H), 9.73 (s, 1H), 8.01 (s, 1H), 7.68 (dd, J = 9.1, 1.9 Hz, 1H), 7.53 (d, J = 9.3 Hz, 1H), 6.77 (s, 2H), 5.38-4.97 (m, 1H), 2.65-2.53 (m, 4H), 1.92-1.71 (m, 1H), 1.18-0.99 (m, 1H); LCMS (electrospray) m/z 434.10 (M + H)+. | L |
| 67 | <br>(2-amino-6-(1H-indol-5-yl)imidazo[1,2-a]pyridin-3-yl)(pyridin-2-yl)methanone | $^1$H NMR (400 MHz, DMSO-$d_6$) δ 11.23 (s, 1H), 10.15 (s, 1H), 8.78 (d, J = 3.3 Hz, 1H), 8.21-8.04 (m, 2H), 7.93 (d, J = 9.3 Hz, 1H), 7.82 (s, 1H), 7.69 (s, 3H), 7.53 (d, J = 8.2 Hz, 1H), 7.48-7.24 (m, 3H), 6.53 (s, 1H); LCMS (electrospray) m/z 354.10 (M + H)+. | L |
| 68 | 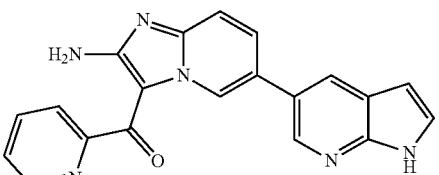<br>(2-amino-6-(1H-pyrrolo[2,3-b]pyridin-5-yl)imidazo[1,2-a]pyridin-3-yl)(pyridin-2-yl)methanone | $^1$H NMR (400 MHz, DMSO-$d_6$) δ 11.80 (s, 1H), 10.11 (s, 1H), 8.78 (d, J = 3.3 Hz, 1H), 8.50 (s, 1H), 8.22 (s, 1H), 8.13 (s, 2H), 7.96 (d, J = 8.8 Hz, 1H), 7.87-7.62 (m, 3H), 7.62-7.34 (m, 2H), 6.55 (s, 1H); LCMS (electrospray) m/z 355.10 (M + H)+. | L |
| 69 | <br>(2-amino-6-(4-fluoro-1H-pyrrolo[2,3-b]pyridin-5-yl)imidazo[1,2-a]pyridin-3-yl)((1S,2S)-2-fluorocyclopropyl)methanone | $^1$H NMR (400 MHz, DMSO-$d_6$) δ 12.14 (s, 1H), 9.79 (s, 1H), 8.38 (d, J = 9.9 Hz, 1H), 7.76 (d, J = 9.3 Hz, 1H), 7.59 (d, J = 2.2 Hz, 1H), 7.49 (d, J = 9.9 Hz, 1H), 6.70 (s, 2H), 6.62 (d, J = 1.6 Hz, 1H), 5.39-4.99 (m, 1H), 2.66-2.54 (m, 1H), 1.96-1.75 (m, 1H), 1.19-1.01 (m, 1H); LCMS (electrospray) m/z 354.10 (M + H)+. | L |

TABLE 1-continued

Compounds of Examples

| Ex # | Structure/Name | 1H NMR/MS (M + 1) | Synthetic Method |
|---|---|---|---|
| 70 | 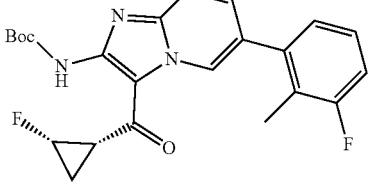<br>tert-butyl (6-(3-fluoro-2-methylphenyl)-3-((1S,2S)-2-fluorocyclopropane-1-carbonyl)imidazo[1,2-a]pyridin-2-yl)carbamate | $^1$H NMR (400 MHz, DMSO-d$_6$) δ 9.85 (s, 1H), 9.47 (d, J = 1.2 Hz, 1H), 7.80 (d, J = 9.2 Hz, 1H), 7.68 (dd, J = 9.6, 2.0 Hz, 1H), 7.38-7.33 (m, 1H), 7.27 (t, J = 8.8 Hz, 1H), 7.20 (d, J = 7.6 Hz, 1H), 5.06-4.83 (m, 1H), 2.91-2.83 (m, 1H), 2.17 (d, J = 2.0 Hz, 3H), 1.91-1.80 (m, 1H), 1.46 (s, 9H), 1.28-1.21 (m, 1H); LCMS (electrospray) m/z 428.20 (M + H)+. | H |
| 71 | 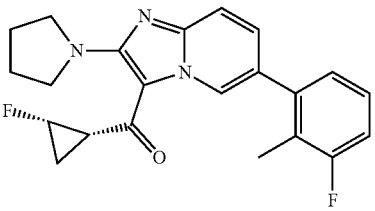<br>(6-(3-fluoro-2-methylphenyl)-2-(pyrrolidin-1-yl)imidazo[1,2-a]pyridin-3-yl)((1S,2S)-2-fluorocyclopropyl)methanone | $^1$H NMR (400 MHz, DMSO-d$_6$) δ 9.64-9.51 (m, 1H), 8.44 (br s, 1H), 7.64-7.55 (m, 2H), 7.42-7.30 (m, 1H), 7.29-7.22 (m, 1H), 7.17 (d, J = 7.2 Hz, 1H), 5.37-4.94 (m, 1H), 4.05-3.73 (m, 2H), 2.19 (br s, 1H), 2.16 (d, J = 2.3 Hz, 3H), 2.08 (s, 2H), 2.04-1.96 (m, 2H), 1.92 (br dd, J = 3.4, 6.3 Hz, 1H), 1.87-1.79 (m, 2H), 1.30-1.11 (m, 1H); LCMS (electrospray) m/z 382.00 (M + H)+. | I |
| 72 | 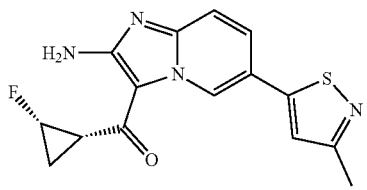<br>(2-amino-6-(3-methylisothiazol-5-yl)imidazo[1,2-a]pyridin-3-yl)((1S,2S)-2-fluorocyclopropyl)methanone | $^1$H NMR (400 MHz, DMSO-d$_6$) δ 9.93 (br s, 1H), 7.81 (dd, J = 1.9, 9.1 Hz, 1H), 7.60 (s, 1H), 7.47 (dd, J = 0.8, 9.2 Hz, 1H), 6.81 (s, 2H), 5.32-5.05 (m, 1H), 2.64-2.55 (m, 1H), 2.46 (s, 3H), 1.95-1.83 (m, 1H), 1.19-1.08 (m, 1H); LCMS (electrospray) m/z 317.20 (M + H)+. | D |
| 73 | 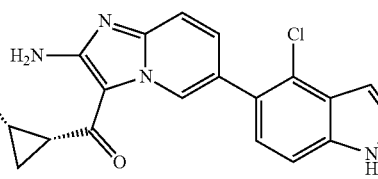<br>(2-amino-6-(4-chloro-1H-indol-5-yl)imidazo[1,2-a]pyridin-3-yl)((1S,2S)-2-fluorocyclopropyl)methanone | $^1$H NMR (400 MHz, DMSO-d$_6$) δ 11.56 (s, 1H), 9.63 (s, 1H), 7.65-7.42 (m, 4H), 7.19 (d, J = 8.0 Hz, 1H), 6.65 (s, 2H), 6.55 (s, 1H), 5.31-5.05 (m, 1H), 2.61-2.54 (m, 1H), 1.88-1.80 (m, 1H), 1.14-1.07 (m, 1H); LCMS (electrospray) m/z 369.10 (M + H)+. | L |
| 74 | 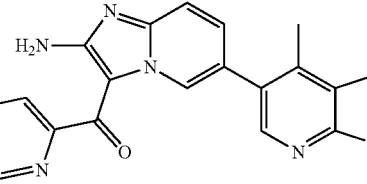<br>(2-amino-6-(4-methyl-1H-pyrrolo[2,3-b]pyridin-5-yl)imidazo[1,2-a]pyridin-3-yl)(pyridin-2-yl)methanone | $^1$H NMR (400 MHz, DMSO-d$_6$) δ 11.69 (d, J = 18.7 Hz, 1H), 10.08-9.49 (m, 1H), 8.86-8.69 (m, 1H), 8.24-7.99 (m, 3H), 7.80-7.57 (m, 4H), 7.55-7.47 (m, 1H), 7.47-7.36 (m, 1H), 6.69-6.51 (m, 1H), 2.50 (d, J = 1.6 Hz, 3H); LCMS (electrospray) m/z 369.10 (M + H)+. | L |

TABLE 1-continued

Compounds of Examples

| Ex # | Structure/Name | 1H NMR/MS (M + 1) | Synthetic Method |
|---|---|---|---|
| 75 | (2-amino-6-(4-chloro-1H-pyrrolo[2,3-b]pyridin-5-yl)imidazo[1,2-a]pyridin-3-yl)(pyridin-2-yl)methanone | $^1$H NMR (400 MHz, DMSO-d$_6$) δ 12.20 (s, 1H), 10.10-9.73 (s, 1H), 8.85-8.69 (m, 1H), 8.31 (s, 1H), 8.22-8.01 (m, 2H), 7.96-7.60 (m, 5H), 7.56-7.37 (m, 1H), 6.59 (t, J = 1.6 Hz, 1H); LCMS (electrospray) m/z 389.10 (M + H)+. | L |
| 76 | (2-amino-6-(3-fluoro-2-methylphenyl)imidazo[1,2-a]pyridin-3-yl)(pyrimidin-2-yl)methanone | $^1$H NMR (400 MHz, DMSO-d$_6$) δ 9.64 (br s, 1H), 9.05-9.02 (m, 2H), 7.73-7.69 (m, 1H), 7.63 (d, J = 8.8 Hz, 1H), 7.47 (d, J = 8.8 Hz, 1H), 7.34 (q, J = 7.27 Hz, 1H), 7.24 (t, J = 8.8 Hz, 1H), 7.20-7.15 (m, 1H), 6.56 (s, 2H), 2.17 (s, 3H); LCMS (electrospray) m/z 348.10 (M + H)+. | B |
| 77 | (2-amino-6-(3-fluoro-2-methylphenyl)imidazo[1,2-a]pyridin-3-yl)(pyrimidin-4-yl)methanone | $^1$H NMR (400 MHz, DMSO-d$_6$) δ 9.77 (br s, 1H), 9.44 (s, 1H), 9.16-9.10 (m, 1H), 8.05-8.00 (m, 1H), 7.70-7.64 (m, 1H), 7.62 (s, 2H), 7.49-7.44 (m, 1H), 7.40-7.31 (m, 1H), 7.25 (t, J = 8.8 Hz, 1H), 7.21-7.16 (m, 1H), 2.19 (s, 3H); LCMS (electrospray) m/z 348.10 (M + H)+. | L |
| 78 | (2-amino-6-(1H-pyrrolo[2,3-b]pyridin-5-yl)imidazo[1,2-a]pyridin-3-yl)(pyrimidin-4-yl)methanone | $^1$H NMR (400 MHz, DMSO-d$_6$) δ 11.89 (s, 1H), 10.17 (br s, 1H), 9.45 (s, 1H), 9.15 (d, J = 4.8 Hz, 1H), 8.49 (s, 1H), 8.22 (s, 1H), 8.07-7.99 (m, 2H), 7.60-7.48 (m, 4H), 6.55-6.54 (m, 1H); LCMS (electrospray) m/z 356.10 (M + H)+. | L |
| 79 | (2-amino-6-(1H-pyrrolo[2,3-b]pyridin-5-yl)imidazo[1,2-a]pyridin-3-yl)(pyrimidin-2-yl)methanone | $^1$H NMR (400 MHz, DMSO-d$_6$) δ 11.80 (s, 1H), 9.92 (br s, 1H), 9.10-9.02 (m, 2H), 8.45 (s, 1H), 8.19 (s, 1H), 7.97 (d, J = 8.8 Hz, 1H), 7.75-7.69 (m, 1H), 7.57-7.47 (m, 2H), 6.66-6.41 (m, 3H); LCMS (electrospray) m/z 356.10 (M + H)+. | L |

TABLE 1-continued

Compounds of Examples

| Ex # | Structure/Name | 1H NMR/MS (M + 1) | Synthetic Method |
|---|---|---|---|
| 80 | 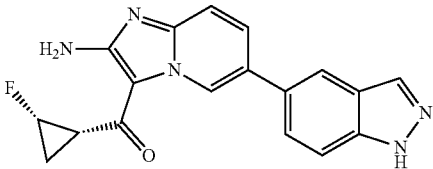<br>(2-amino-6-(1H-indazol-5-yl)imidazo[1,2-a]pyridin-3-yl)((1S,2S)-2-fluorocyclopropyl)methanone | $^1$H NMR (400 MHz, DMSO-d$_6$) δ 13.18 (s, 1H), 10.20-9.66 (s, 1H), 8.16 (s, 1H), 8.04 (s, 1H), 7.88 (d, J = 9.3 Hz, 1H), 7.66 (d, J = 3.8 Hz, 2H), 7.46 (d, J = 9.3 Hz, 1H), 6.66 (s, 2H), 5.40-4.99 (m, 1H), 2.89-2.56 (m, 2H), 1.97-1.77 (m, 1H), 1.20-0.97 (m, 1H); LCMS (electrospray) m/z 336.10 (M + H)+. | L |
| 81 | 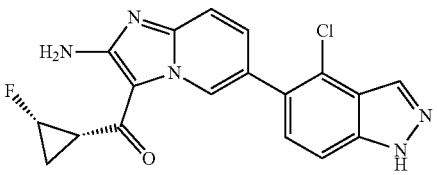<br>(2-amino-6-(4-chloro-1H-indazol-5-yl)imidazo[1,2-a]pyridin-3-yl)((1S,2S)-2-fluorocyclopropyl)methanone | $^1$H NMR (400 MHz, DMSO-d$_6$) δ 13.54 (s, 1H), 9.66 (s, 1H), 8.20 (s, 1H), 7.75-7.56 (m, 2H), 7.47 (q, J = 4.6 Hz, 2H), 6.70 (s, 2H), 5.42-4.94 (m, 1H), 2.65-2.53 (m, 1H), 1.92-1.68 (m, 1H), 1.16-0.98 (m, 1H); LCMS (electrospray) m/z 370.05 (M + H)+. | L |
| 82 | 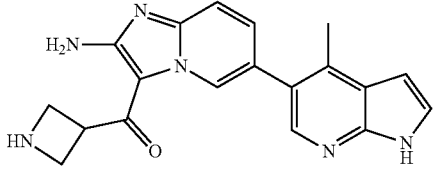<br>(2-amino-6-(4-methyl-1H-pyrrolo[2,3-b]pyridin-5-yl)imidazo[1,2-a]pyridin-3-yl)(azetidin-3-yl)methanone | $^1$H NMR (400 MHz, DMSO-d$_6$) δ 11.71 (s, 1H), 9.62 (s, 1H), 8.11 (s, 1H), 7.57 (d, J = 8.2 Hz, 1H), 7.50 (s, 1H), 7.41 (d, J = 9.3 Hz, 1H), 6.58 (s, 1H), 6.38 (s, 2H), 4.18 (t, J = 7.4 Hz, 1H), 3.74 (d, J = 6.6 Hz, 4H), 2.47 (s, 3H); LCMS (electrospray) m/z 347.10 (M + H)+. | L |
| 83 | 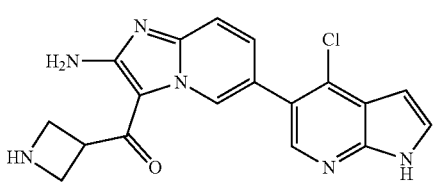<br>CF$_3$COOH   CF$_3$COOH<br>CF$_3$COOH   CF$_3$COOH<br>(2-amino-6-(4-chloro-1H-pyrrolo[2,3-b]pyridin-5-yl)imidazo[1,2-a]pyridin-3-yl)(azetidin-3-yl)methanone. 4 TFA salt | $^1$H NMR (400 MHz, DMSO-d$_6$) δ 12.17 (s, 1H), 9.74 (s, 1H), 8.72 (s, 2H), 8.25 (s, 1H), 7.69-7.67 (m, 2H), 7.47 (d, J = 9.3 Hz, 1H), 6.55 (s, 2H), 4.32-4.30 (m, 1H), 4.26-4.21 (m, 2H), 4.13-4.09 (m, 2H); LCMS (electrospray) m/z 367.10 (M + H)+. | L |
| 84 | 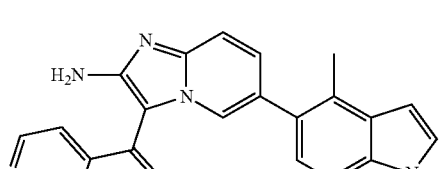<br>(2-amino-6-(4-methyl-1H-pyrrolo[2,3-b]pyridin-5-yl)imidazo[1,2-a]pyridin-3-yl)(pyrimidin-4-yl)methanone | $^1$H NMR (400 MHz, DMSO-d$_6$) δ 11.70 (s, 1H), 9.72 (s, 1H), 9.41 (s, 1H), 9.09 (d, J = 5.5 Hz, 1H), 8.09 (s, 1H), 7.98 (s, 1H), 7.68 (d, J = 8.8 Hz, 1H), 7.55 (s, 2H), 7.45 (t, J = 8.5 Hz, 2H), 6.56 (s, 1H); LCMS (electrospray) m/z 370.10 (M + H)+. | L |

TABLE 1-continued

Compounds of Examples

| Ex # | Structure/Name | 1H NMR/MS (M + 1) | Synthetic Method |
|---|---|---|---|
| 85 | (2-amino-6-(4-methyl-1H-pyrrolo[2,3-b]pyridin-5-yl)imidazo[1,2-a]pyridin-3-yl)(pyrimidin-2-yl)methanone | $^1$H NMR (400 MHz, DMSO-d$_6$) δ 11.72 (s, 1H), 9.67 (br s, 1H), 9.03 (d, J = 4.8 Hz, 2H), 8.10 (s, 1H), 7.72-7.67 (m, 2H), 7.51-7.47 (m, 2H), 6.62-6.37 (m, 3H); LCMS (electrospray) m/z 370.10 (M + H)+. | L |
| 86 | (2-amino-6-(1H-pyrrolo[2,3-b]pyridin-5-yl)imidazo[1,2-a]pyridin-3-yl)(azetidin-3-yl)methanone. 4 TFA salt | $^1$H NMR (400 MHz, DMSO-d$_6$) δ 11.82 (s, 1H), 9.95 (br s, 1H), 8.81 (s, 2H), 8.51-8.48 (m, 1H), 8.23-8.20 (m, 1H), 7.97-7.93 (m, 1H), 7.61-7.48 (m, 2H), 6.61-6.52 (m, 3H), 4.41-3.98 (m, 5H); LCMS (electrospray) m/z 333.10 (M + H)+. | L |
| 87 | (6-(3-fluoro-2-methylphenyl)-2-((2-(methylamino)ethyl)amino)imidazo[1,2-a]pyridin-3-yl)((1S,2S)-2-fluorocyclopropyl)methanone | $^1$H NMR (400 MHz, DMSO-d$_6$) δ 9.50-(br s, 1H), 7.57-7.51 (m, 2H), 7.36-7.31 (m, 1H), 7.26-7.17 (m, 2H), 5.27-5.07 (m, 1H), 3.58 (q, 6.0 Hz, 2H), 2.76 (t, J = 6.0 Hz, 2H), 2.63-2.52 (m, 1H), 2.33 (s, 3H), 2.17 (d, J = 1.6 Hz, 3H), 1.89-1.79 (m, 1H), 1.24-1.10 (m, 1H); LCMS (electrospray) m/z 385.15 (M + H)+. | J |
| 88 | N-(6-(3-fluoro-2-methylphenyl)-3-((1S,2S)-2-fluorocyclopropane-1-carbonyl)imidazo[1,2-a]pyridin-2-yl)acetamide | $^1$H NMR (400 MHz, DMSO-d$_6$) δ 10.56 (s, 1H), 9.51 (d, J = 1.1 Hz, 1H), 7.83 (d, J = 8.8 Hz, 1H), 7.70 (dd, J = 9.3, 1.6 Hz, 1H), 7.43-7.32 (m, 1H), 7.28 (t, J = 9.1 Hz, 1H), 7.21 (d, J = 7.7 Hz, 1H), 5.12-4.82 (m, 1H), 2.87-2.73 (m, 1H), 2.18 (d, J = 2.2 Hz, 3H), 2.16 (s, 3H), 1.92-1.75 (m, 1H), 1.30-1.13 (m, 1H); LCMS (electrospray) m/z 370.10 (M + H)+. | K |

TABLE 1-continued

Compounds of Examples

| Ex # | Structure/Name | 1H NMR/MS (M + 1) | Synthetic Method |
|---|---|---|---|
| 89 | 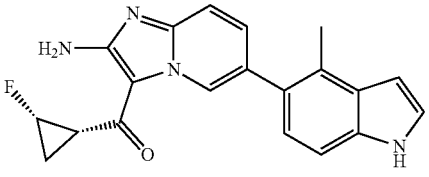<br>(2-amino-6-(4-methyl-1H-indol-5-yl)imidazo[1,2-a]pyridin-3-yl)((1S,2S)-2-fluorocyclopropyl)methanone | $^1$H NMR (400 MHz, DMSO-$d_6$) δ 11.15 (s, 1H), 9.47 (s, 1H), 7.50 (dd, J = 9.1, 1.9 Hz, 1H), 7.41-7.32 (m, 1H), 7.28 (d, J = 8.2 Hz, 2H), 7.28 (d, J = 8.2 Hz, 1H), 6.98 (d, J = 8.2 Hz, 1H), 6.53 (d, J = 33.0 Hz, 3H), 5.30-4.98 (m, 1H), 2.60-2.49 (m, 1H), 2.38 (s, 3H), 1.90-1.68 (m, 1H), 1.11-0.96 (m, 1H); LCMS (electrospray) m/z 349.10 (M + H)+. | L |
| 90 | 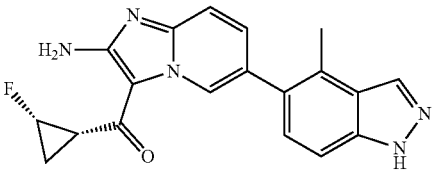<br>(2-amino-6-(4-methyl-1H-indazol-5-yl)imidazo[1,2-a]pyridin-3-yl)((1S,2S)-2-fluorocyclopropyl)methanone | $^1$H NMR (400 MHz, DMSO-$d_6$) δ 13.13 (s, 1H), 9.54 (br s, 1H), 8.21 (s, 1H), 7.56 (dd, J = 9.0, 1.8 Hz, 1H), 7.44 (t, J = 8.8 Hz, 2H), 7.28 (d, J = 8.8 Hz, 1H), 6.65 (s, 2H), 5.27-5.07 (m, 1H), 2.60-2.54 (m, 1H), 1.87-1.78 (m, 1H), 1.17-1.05 (m, 1H); LCMS (electrospray) m/z 350.10 (M + H)+. | L |
| 91 | 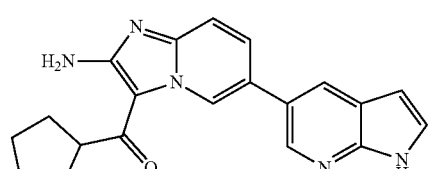<br>(2-amino-6-(1H-pyrrolo[2,3-b]pyridin-5-yl)imidazo[1,2-a]pyridin-3-yl)(pyrrolidin-3-yl)methanone | $^1$H NMR (400 MHz, DMSO-$d_6$) δ 11.75 (s, 1H), 9.88 (br s, 1H), 8.43 (d, J = 2.4 Hz, 1H), 8.15 (d, J = 2.4 Hz, 1H), 7.87 (dd, J = 9.0, 2.2 Hz, 1H), 7.51 (t, J = 3.2 Hz, 1H), 7.44 (d, J = 9.6 Hz, 1H), 6.61 (s, 2H), 6.50-6.49 (m, 1H), 3.85-3.77 (m, 1H), 3.40-3.32 (m, 1H), 3.25-3.20 (m, 1H), 3.12-3.05 (m, 2H), 2.60-2.54 (m, 1H), 2.25-1.96 (m, 2H); LCMS (electrospray) m/z 347.10 (M + H)+. | L |
| 92 | 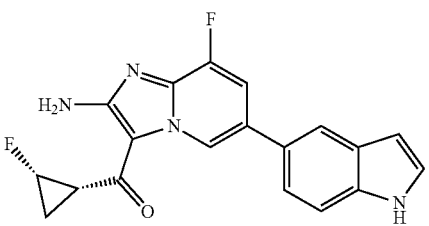<br>(2-amino-8-fluoro-6-(1H-indol-5-yl)imidazo[1,2-a]pyridin-3-yl)((1S,2S)-2-fluorocyclopropyl)methanone | $^1$H NMR (400 MHz, DMSO-$d_6$) δ 11.24 (s, 1H), 9.70 (s, 1H), 7.95-7.78 (m, 2H), 7.51 (q, J = 4.2 Hz, 1H), 7.46-7.30 (m, 2H), 6.80 (s, 2H), 6.52 (d, J = 2.2 Hz, 1H), 5.34-5.05 (m, 1H), 2.70-2.56 (m, 1H), 1.96-1.81 (m, 1H), 1.27-1.04 (m, 1H); LCMS (electrospray) m/z 353.10 (M + H)+. | M |
| 93 | 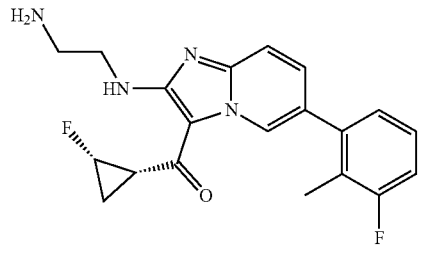<br>(2-((2-aminoethyl)amino)-6-(3-fluoro-2-methylphenyl)imidazo[1,2-a]pyridin-3-yl)((1S,2S)-2-fluorocyclopropyl)methanone | $^1$H NMR (400 MHz, DMSO-$d_6$) δ 9.52 (br s, 1H), 7.58-7.50 (m, 2H), 7.34 (q, J = 7.2 Hz, 1H), 7.24 (t, J = 8.8 Hz, 1H), 7.18 (d, J = 7.6 Hz, 1H), 5.30-5.08 (m, 1H), 3.50 (q, 6.6 Hz, 2H), 2.81 (t, J = 6.6 Hz, 2H), 2.65-2.52 (m, 1H), 2.17 (d, J = 2.0 Hz, 3H), 1.90-1.79 (m, 1H), 1.17-1.08 (m, 1H); LCMS (electrospray) m/z 371.10 (M + H)+. | J |

TABLE 1-continued

Compounds of Examples

| Ex # | Structure/Name | 1H NMR/MS (M + 1) | Synthetic Method |
|---|---|---|---|
| 94 | 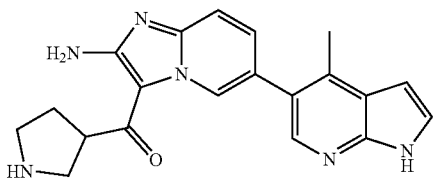<br>(2-amino-6-(4-methyl-1H-pyrrolo[2,3-b]pyridin-5-yl)imidazo[1,2-a]pyridin-3-yl)(pyrrolidin-3-yl)methanone | ¹H NMR (400 MHz, DMSO-d₆) δ 11.70 (s, 1H), 9.60 (br s, 1H), 8.09 (s, 1H), 7.56 (dd, J = 9.0, 1.8 Hz, 1H), 7.51-7.47 (m, 1H), 7.44-7.38 (m, 1H), 6.57 (d, J = 2.8 Hz, 1H), 6.51 (s, 2H), 3.60-3.53 (m, 1H), 3.10-3.05 (m, 1H), 2.89-2.74 (m, 3H), 2.46 (s, 3H), 2.03-1.88 (m, 2H); LCMS (electrospray) m/z 361.10 (M + H)+. | L |
| 95 | 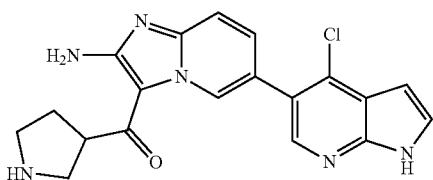<br>(2-amino-6-(4-chloro-1H-pyrrolo[2,3-b]pyridin-5-yl)imidazo[1,2-a]pyridin-3-yl)(pyrrolidin-3-yl)methanone | ¹H NMR (400 MHz, DMSO-d₆) δ 12.18 (s, 1H), 9.72 (br s, 1H), 8.27 (s, 1H), 7.67 (d, J = 3.2 Hz, 1H), 7.63 (dd, J = 9.0, 2.2 Hz, 1H), 7.47-7.41 (m, 1H), 6.67-6.51 (m, 3H), 3.60-3.53 (m, 1H), 3.10-3.05 (m, 1H), 2.90-2.74 (m, 3H), 2.01-1.88 (m, 2H); LCMS (electrospray) m/z 381.10 (M + H)+. | L |
| 96 | 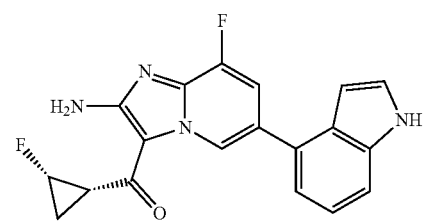<br>(2-amino-8-fluoro-6-(1H-indol-4-yl)imidazo[1,2-a]pyridin-3-yl)((1S,2S)-2-fluorocyclopropyl)methanone | ¹H NMR (400 MHz, DMSO-d₆) δ 11.40 (s, 1H), 9.82 (s, 1H), 7.79 (dd, J = 11.5, 1.6 Hz, 1H), 7.57-7.40 (m, 2H), 7.29-7.12 (m, 2H), 6.84 (s, 2H), 6.64 (s, 1H), 5.34-5.02 (m, 1H), 2.74-2.55 (m, 1H), 1.96-1.80 (m, 1H), 1.22-1.06 (m, 1H); LCMS (electrospray) m/z 353.10 (M + H)+. | M |
| 97 | 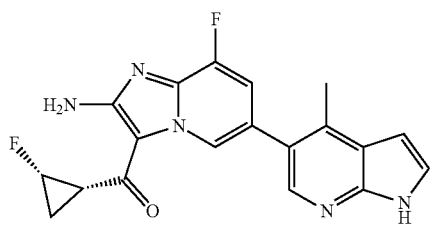<br>(2-amino-8-fluoro-6-(4-methyl-1H-pyrrolo[2,3-b]pyridin-5-yl)imidazo[1,2-a]pyridin-3-yl)((1S,2S)-2-fluorocyclopropyl)methanone | ¹H NMR (400 MHz, DMSO-d₆) δ 11.73 (s, 1H), 9.35 (s, 1H), 8.11 (s, 1H), 7.64 (dd, J = 11.3, 1.4 Hz, 1H), 7.50 (t, J = 3.0 Hz, 1H), 6.84 (s, 2H), 6.58 (s, 1H), 5.37-5.03 (m, 1H), 2.74-2.56 (m, 1H), 2.48 (d, J = 4.9 Hz, 3H), 1.96-1.75 (m, 1H), 1.23-1.02 (m, 1H); LCMS (electrospray) m/z 368.10 (M + H)+. | M |
| 98 | 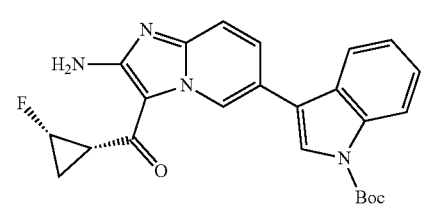<br>tert-butyl 3-(2-amino-3-((1S,2S)-2-fluorocyclopropane-1-carbonyl)imidazo[1,2-a]pyridin-6-yl)-1H-indole-1-carboxylate | ¹H NMR (400 MHz, DMSO-d₆) δ 9.99 (s, 1H), 8.19 (d, J = 7.7 Hz, 1H), 8.04 (s, 1H), 7.95-7.83 (m, 2H), 7.54-7.36 (m, 3H), 6.68 (s, 2H), 5.33-5.04 (m, 1H), 2.65-2.55 (m, 1H), 1.97-1.79 (m, 1H), 1.66 (s, 9H), 1.16-1.05 (m, 1H); LCMS (electrospray) m/z 435.15 (M + H)+. | L |

TABLE 1-continued

Compounds of Examples

| Ex # | Structure/Name | 1H NMR/MS (M + 1) | Synthetic Method |
|---|---|---|---|
| 99 | 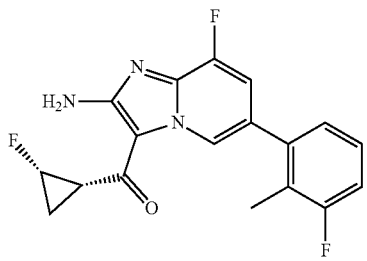<br>(2-amino-8-fluoro-6-(3-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.35 (s, 1H), 7.62-7.59 (m, 1H), 7.36-7.19 (m, 3H), 6.87 (s, 1H), 5.29-5.10 (m, 1H), 2.61-2.52 (m, 1H), 2.19 (s, 3H), 1.89-1.84 (m, 1H), 1.17-1.13 (m, 1H); LCMS (electrospray) m/z 346.10 (M + H)+. | M |
| 100 | <br>(2-amino-6-(5-methyl-1H-indol-4-yl)imidazo[1,2-a]pyridin-3-yl)((1S,2S)-2-fluorocyclopropyl)methanone | $^1$H NMR (400 MHz, DMSO-d$_6$) δ 11.14 (s, 1H), 9.55 (s, 1H), 7.53 (dd, J = 8.8, 1.6 Hz, 1H), 7.46 (d, J = 8.8 Hz, 1H), 7.35 (d, J = 8.2 Hz, 1H), 7.30 (t, J = 2.7 Hz, 1H), 7.06 (d, J = 8.2 Hz, 1H), 6.63 (s, 2H), 6.07 (s, 1H), 5.33-5.00 (m, 1H), 2.65-2.51 (m, 1H), 2.26 (s, 3H), 1.90-1.73 (m, 1H), 1.14-0.98 (m, 1H); LCMS (electrospray) m/z 349.10 (M + H)+. | L |
| 101 | 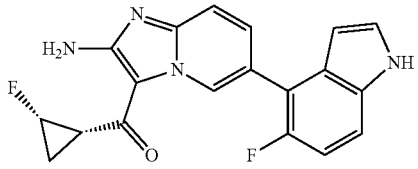<br>(2-amino-6-(5-fluoro-1H-indol-4-yl)imidazo[1,2-a]pyridin-3-yl)((1S,2S)-2-fluorocyclopropyl)methanone | $^1$H NMR (400 MHz, DMSO-d$_6$) δ 11.41 (s, 1H), 9.83 (s, 1H), 7.72 (dt, J = 8.8, 1.6 Hz, 1H), 7.57-7.40 (m, 3H), 7.08 (dd, J = 11.0, 8.8 Hz, 1H), 6.68 (s, 2H), 6.44 (t, J = 2.2 Hz, 1H), 5.32-5.03 (m, 1H), 2.65-2.53 (m, 1H), 1.94-1.74 (m, 1H), 1.15-1.02 (m, 1H); LCMS (electrospray) m/z 353.10 (M + H)+. | L |
| 102 | 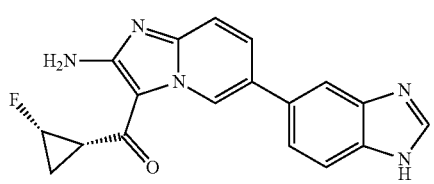<br>(2-amino-6-(1H-benzo[d]imidazol-5-yl)imidazo[1,2-a]pyridin-3-yl)((1S,2S)-2-fluorocyclopropyl)methanone | $^1$H NMR (400 MHz, DMSO-d$_6$) δ 12.54 (s, 1H), 9.88 (br s, 1H), 8.28 (s, 1H), 7.93-7.62 (m, 3H), 7.52-7.42 (m, 2H), 6.65 (s, 2H), 5.29-5.07 (m, 1H), 2.64-2.56 (m, 1H), 1.93-1.82 (m, 1H), 1.17-1.07 (m, 1H); LCMS (electrospray) m/z 336.10 (M + H)+. | L |
| 103 | 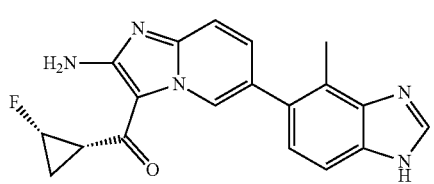<br>(2-amino-6-(4-methyl-1H-benzo[d]imidazol-5-yl)imidazo[1,2-a]pyridin-3-yl)((1S,2S)-2-fluorocyclopropyl)methanone | $^1$H NMR (400 MHz, DMSO-d$_6$) δ 12.65 (s, 0.5H), 12.50 (s, 0.5H), 9.54 (br s, 1H), 8.29 (s, 0.5H), 8.24 (s, 0.5H), 7.59-7.40 (m, 3H), 7.14 (t, J = 9.0 Hz, 1H), 6.65 (s, 2H), 5.28-5.05 (m, 1H), 2.62-2.53 (m, 1H), 2.52 (s, 1.5H), 2.44 (s, 1.5H), 1.89-1.77 (m, 1H), 1.14-1.04 (m, 1H); LCMS (electrospray) m/z 350.10 (M + H)+. | L |

TABLE 1-continued

Compounds of Examples

| Ex # | Structure/Name | 1H NMR/MS (M + 1) | Synthetic Method |
|---|---|---|---|
| 104 | (2-amino-6-(1H-pyrrolo[2,3-b]pyridin-4-yl)imidazo[1,2-a]pyridin-3-yl)((1S,2S)-2-fluorocyclopropyl)methanone | $^1$H NMR (400 MHz, DMSO-$d_6$) δ 11.86 (s, 1H), 10.10 (br s, 1H), 8.27 (d, J = 4.8 Hz, 1H), 7.91 (dd, J = 9.2, 2.0 Hz, 1H), 7.59 (t, J = 3.0 Hz, 1H), 7.49 (d, J = 9.6 Hz, 1H), 7.25 (d, J = 4.8 Hz, 1H), 6.72 (s, 2H), 6.68-6.65 (m, 1H), 5.26-5.03 (m, 1H), 2.61-2.52 (m, 1H), 1.91-1.79 (m, 1H), 1.12-1.05 (m, 1H); LCMS (electrospray) m/z 336.10 (M + H)+. | L |
| 105 | (2-amino-6-(1H-indol-3-yl)imidazo[1,2-a]pyridin-3-yl)((1S,2S)-2-fluorocyclopropyl)methanone | $^1$H NMR (400 MHz, DMSO-$d_6$) δ 11.49 (s, 1H), 10.02 (s, 1H), 7.97-7.77 (m, 3H), 7.56-7.37 (m, 2H), 7.25-7.12 (m, 2H), 6.58 (s, 2H), 5.34-5.04 (m, 1H), 2.71-2.54 (m, 1H), 1.97-1.81 (m, 1H), 1.17-1.02 (m, 1H); LCMS (electrospray) m/z 335.10 (M + H)+. | L |
| 106 | (2-amino-6-(1,4-dimethyl-1H-pyrrolo[2,3-b]pyridin-5-yl)imidazo[1,2-a]pyridin-3-yl)((1S,2S)-2-fluorocyclopropyl)methanone | $^1$H NMR (400 MHz, DMSO-$d_6$) δ 9.54 (br s, 1H), 8.15 (s, 1H), 7.61-7.52 (m, 2H), 7.44 (d, J = 8.8 Hz, 1H), 6.67 (br s, 2H), 6.60 (d, J = 3.2 Hz, 1H), 5.28-5.06 (m, 1H), 3.84 (s, 3H), 2.63-2.53 (m, 1H), 2.46 (s, 3H), 1.89-1.77 (m, 1H), 1.14-1.04 (m, 1H); LCMS (electrospray) m/z 364.10 (M + H)+. | L |
| 107 | 2-amino-N-cyclopropyl-6-(3-fluoro-2-methylphenyl)-N-methylimidazo[1,2-a]pyridine-3-carboxamide | $^1$H NMR (400 MHz, DMSO-$d_6$) δ 8.49 (s, 1H), 7.35-7.25 (m, 3H), 7.21 (t, J = 9.0 Hz, 1H), 7.14 (d, J = 7.2 Hz, 1H), 5.71 (s, 2H), 2.94 (s, 3H), 2.91-2.84 (m, 1H), 2.16 (s, 3H), 0.60-0.51 (m, 4H); LCMS (electrospray) m/z 339.10 (M + H)+. | N |
| 108 | 2-amino-6-(3-fluoro-2-methylphenyl)-N-((1R,2S)-2-fluorocyclopropyl)imidazo[1,2-a]pyridine-3-carboxamide | $^1$H NMR (400 MHz, DMSO-$d_6$) δ 9.16 (t, J = 1.4 Hz, 1H), 7.40-7.29 (m, 4H), 7.25-7.20 (m, 1H), 7.17 (d, J = 7.6 Hz, 1H), 6.03 (s, 2H), 4.84-4.64 (m, 1H), 2.82-2.75 (m, 1H), 2.17 (d, J = 1.4 Hz, 3H), 1.19-1.04 (m, 4H); LCMS (electrospray) m/z 343.10 (M + H)+. | N |

TABLE 1-continued

Compounds of Examples

| Ex # | Structure/Name | 1H NMR/MS (M + 1) | Synthetic Method |
|---|---|---|---|
| 109 | 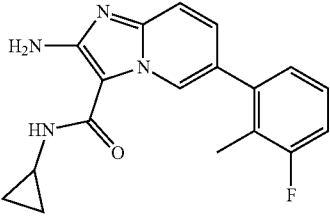<br>2-amino-N-cyclopropyl-6-(3-fluoro-2-methylphenyl)imidazo[1,2-a]pyridine-3-carboxamide | $^1$H NMR (400 MHz, DMSO-d$_6$) δ 9.20 (t, J = 1.4 Hz, 1H), 7.38-7.30 (m, 3H), 7.28-7.20 (m, 2H), 7.17 (d, J = 7.6 Hz, 1H), 5.98 (s, 2H), 2.80-2.74 (m, 1H), 2.17 (d, J = 2.0 Hz, 3H), 0.69-0.55 (m, 4H); LCMS (electrospray) m/z 325.10 (M + H)+. | N |
| 110 | 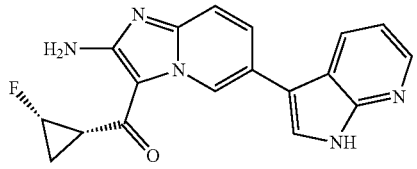<br>(2-amino-6-(1H-pyrrolo[2,3-b]pyridin-3-yl)imidazo[1,2-a]pyridin-3-yl)((1S,2S)-2-fluorocyclopropyl)methanone | $^1$H NMR (400 MHz, DMSO-d$_6$) δ 12.04 (s, 1H), 10.02 (s, 1H), 8.31 (t, J = 2.5 Hz, 1H), 8.23 (d, J = 7.1 Hz, 1H), 8.00 (d, J = 2.2 Hz, 1H), 7.91 (dd, J = 9.1, 1.9 Hz, 1H), 7.49-7.43 (m, 1H), 7.24 (q, J = 4.2 Hz, 1H), 6.61 (s, 2H), 5.27-5.08 (m, 1H), 2.59-2.59 (m, 1H), 1.93-1.87 (m, 1H), 1.14-1.08 (m, 1H); LCMS (electrospray) m/z 336.10 (M + H)+. | L |
| 111 | 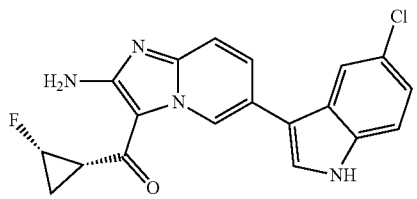<br>(2-amino-6-(5-chloro-1H-indol-3-yl)imidazo[1,2-a]pyridin-3-yl)((1S,2S)-2-fluorocyclopropyl)methanone | $^1$H NMR (400 MHz, DMSO-d$_6$) δ 11.66 (s, 1H), 9.88 (s, 1H), 7.86 (d, J = 2.2 Hz, 1H), 7.82 (dd, J = 9.1, 1.9 Hz, 1H), 7.77 (d, J = 1.6 Hz, 1H), 7.46 (d, J = 8.8 Hz, 1H), 7.41 (d, J = 9.3 Hz, 1H), 7.17 (dd, J = 8.4, 2.1 Hz, 1H), 6.58 (s, 2H), 5.23-5.08 (m, 1H), 2.56-2.56 (m, 1H), 1.89-1.84 (m, 1H), 1.12-1.05 (m, 1H); LCMS (electrospray) m/z 369.10 (M + H)+. | L |
| 112 | 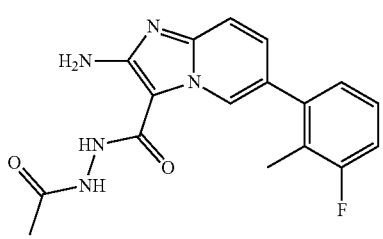<br>N'-acetyl-2-amino-6-(3-fluoro-2-methylphenyl)imidazo[1,2-a]pyridine-3-carbohydrazide | $^1$H NMR (400 MHz, DMSO-d$_6$) δ 9.82 (s, 1H), 9.10 (s, 1H), 9.06 (t, J = 1.4 Hz, 1H), 7.39 (d, J = 1.1 Hz, 2H), 7.33-7.16 (m, 3H), 6.18 (s, 2H), 2.16 (d, J = 2.2 Hz, 3H), 1.90 (s, 3H); LCMS (electrospray) m/z 342.10 (M + H)+. | O |
| 113 | 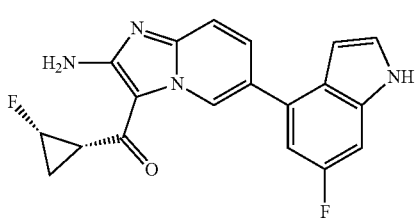<br>(2-amino-6-(6-fluoro-1H-indol-4-yl)imidazo[1,2-a]pyridin-3-yl)((1S,2S)-2-fluorocyclopropyl)methanone | $^1$H NMR (400 MHz, DMSO-d$_6$) δ 11.42 (s, 1H), 9.96 (s, 1H), 7.86 (dd, J = 9.1, 1.9 Hz, 1H), 7.49 (d, J = 8.8 Hz, 1H), 7.45 (dd, J = 6.0, 3.8 Hz, 1H), 7.21 (dd, J = 9.6, 1.4 Hz, 1H), 7.04 (dd, J = 10.4, 2.2 Hz, 1H), 6.80 (s, 2H), 6.58 (s, 1H), 5.22-5.05 (m, 1H), 2.58-2.55 (m, 1H), 1.87-1.81 (m, 1H), 1.10-1.06 (m, 1H); LCMS (electrospray) m/z 353.10 (M + H)+. | L |

TABLE 1-continued

Compounds of Examples

| Ex # | Structure/Name | 1H NMR/MS (M + 1) | Synthetic Method |
|---|---|---|---|
| 114 | 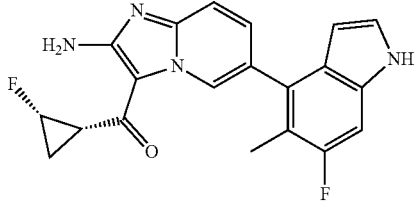<br>(2-amino-6-(6-fluoro-5-methyl-1H-indol-4-yl)imidazo[1,2-a]pyridin-3-yl)((1S,2S)-2-fluorocyclopropyl)methanone | ¹H NMR (400 MHz, DMSO-d₆) δ 11.25 (s, 1H), 9.60 (s, 1H), 7.63 (dd, J = 8.8, 1.6 Hz, 1H), 7.55 (d, J = 9.3 Hz, 1H), 7.32 (t, J = 2.7 Hz, 1H), 7.25 (d, J = 10.4 Hz, 1H), 6.96 (s, 2H), 6.09 (t, J = 2.2 Hz, 1H), 5.27-5.07 (m, 1H), 2.62-2.55 (m, 1H), 2.16 (d, J = 2.7 Hz, 3H), 1.87-1.79 (m, 1H), 1.16-1.09 (m, 1H); LCMS (electrospray) m/z 367.10 (M + H)+. | L |
| 115 | <br>(2-amino-6-(quinolin-4-yl)imidazo[1,2-a]pyridin-3-yl)((1S,2S)-2-fluorocyclopropyl)methanone | ¹H NMR (400 MHz, DMSO-d₆) δ 9.72 (s, 1H), 8.94 (d, J = 4.4 Hz, 1H), 8.10 (d, J = 8.2 Hz, 1H), 7.92 (d, J = 8.8 Hz, 1H), 7.82-7.78 (m, 1H), 7.68 (d, J = 8.8 Hz, 1H), 7.61 (t, J = 7.7 Hz, 1H), 7.55-7.50 (m, 2H), 6.75 (s, 2H), 5.21-5.05 (m, 1H), 2.58-2.52 (m, 1H), 1.82-1.76 (m, 1H), 1.11-1.02 (m, 1H); LCMS (electrospray) m/z 347.10 (M + H)+. | L |
| 116 | 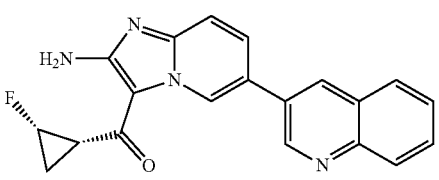<br>(2-amino-6-(quinolin-3-yl)imidazo[1,2-a]pyridin-3-yl)((1S,2S)-2-fluorocyclopropyl)methanone | ¹H NMR (400 MHz, DMSO-d₆) δ 9.86-10.14 (1H), 9.19 (d, J = 2.2 Hz, 1H), 8.64 (d, J = 2.2 Hz, 1H), 8.08-8.00 (m, 3H), 7.78-7.74 (m, 1H), 7.64 (t, J = 7.1 Hz, 1H), 7.52 (d, J = 9.3 Hz, 1H), 6.74 (s, 2H), 5.25-5.09 (m, 1H), 2.54-2.63 (m, 1H), 1.88-1.82 (m, 1H), 1.15-1.08 (m, 1H); LCMS (electrospray) m/z 347.10 (M + H)+. | L |
| 117 | 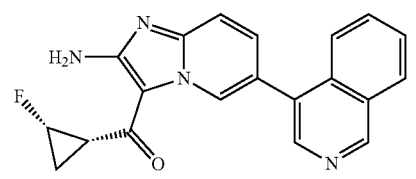<br>(2-amino-6-(isoquinolin-4-yl)imidazo[1,2-a]pyridin-3-yl)((1S,2S)-2-fluorocyclopropyl)methanone | ¹H NMR (400 MHz, DMSO-d₆) δ 9.67 (s, 1H), 9.37 (s, 1H), 8.49 (s, 1H), 8.23 (d, J = 7.7 Hz, 1H), 7.85 (d, J = 8.2 Hz, 1H), 7.82-7.78 (m, 1H), 7.73 (td, J = 7.4, 1.1 Hz, 1H), 7.66 (dd, J = 9.1, 1.9 Hz, 1H), 7.50 (d, J = 8.8 Hz, 1H), 6.71 (s, 2H), 5.22-5.04 (m, 1H), 2.58-2.54 (m, 1H), 1.83-1.75 (m, 1H), 1.09-1.03 (m, 1H); LCMS (electrospray) m/z 347.10 (M + H)+. | L |
| 118 | 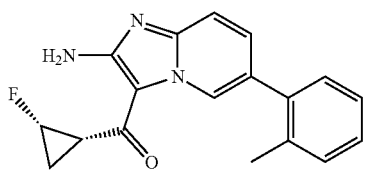<br>(2-amino-6-(o-tolyl)imidazo[1,2-a]pyridin-3-yl)((1S,2S)-2-fluorocyclopropyl)methanone | ¹H NMR (400 MHz, DMSO-d₆) δ 9.46 (s, 1H), 7.51 (d, J = 9.1 Hz, 1H), 7.38 (d, J = 9.9 Hz, 1H), 7.31-7.24 (m, 4H), 6.63 (s, 2H), 5.22-5.04 (m, 1H), 2.55-2.50 (m, 1H), 2.23 (s, 3H), 1.83-1.76 (m, 1H), 1.08-1.03 (m, 1H); LCMS (electrospray) m/z 311.10 (M + H)+. | L |

TABLE 1-continued

Compounds of Examples

| Ex # | Structure/Name | 1H NMR/MS (M + 1) | Synthetic Method |
|---|---|---|---|
| 119 | 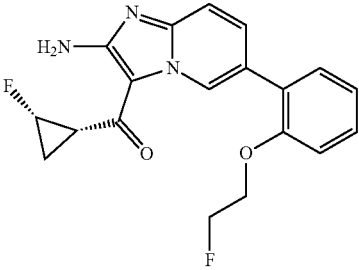<br>(2-amino-6-(2-(2-fluoroethoxy)phenyl)imidazo[1,2-a]pyridin-3-yl)((1S,2S)-2-fluorocyclopropyl)methanone | $^1$H NMR (400 MHz, DMSO-d$_6$) δ 9.70 (s, 1H), 7.70 (d, J = 9.3 Hz, 1H), 7.44-7.36 (m, 3H), 7.17 (d, J = 7.7 Hz, 1H), 7.09 (dd, J = 7.7, 6.6 Hz, 1H), 6.67 (s, 2H), 5.08-4.91 (m, 1H), 4.77 (t, J = 3.8 Hz, 1H), 4.65 (t, J = 3.8 Hz, 1H), 4.33 (t, J = 3.8 Hz, 1H), 4.26 (t, J = 3.8 Hz, 1H), 3.10-3.02 (m, 1H), 1.66-1.55 (m, 1H), 1.39-1.31 (m, 1H); LCMS (electrospray) m/z 358.10 (M + H)+. | L |
| 120 | 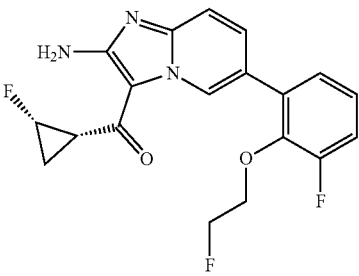<br>(2-amino-6-(3-fluoro-2-(2-fluoroethoxy)phenyl)imidazo[1,2-a]pyridin-3-yl)((1S,2S)-2-fluorocyclopropyl)methanone | $^1$H NMR (400 MHz, DMSO-d$_6$) δ 9.71 (s, 1H), 7.70 (d, J = 9.1 Hz, 1H), 7.42 (d, J = 9.3 Hz, 1H), 7.38-7.32 (m, 1H), 7.29-7.24 (m, 2H), 6.72 (s, 2H), 5.09-4.92 (m, 1H), 4.55 (t, J = 3.8 Hz, 1H), 4.43 (t, J = 3.8 Hz, 1H), 4.15 (t, J = 3.6 Hz, 1H), 4.08 (t, J = 3.6 Hz, 1H), 3.08-3.03 (m, 1H), 1.64-1.59 (m, 1H), 1.38-1.33 (m, 1H); LCMS (electrospray) m/z 376.10 (M + H)+. | L |
| 121 | 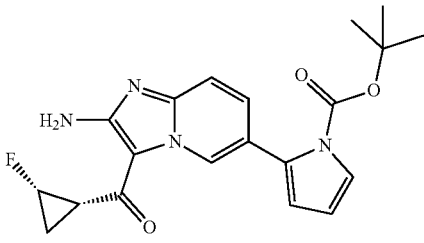<br>tert-butyl 2-(2-amino-3-((1S,2S)-2-fluorocyclopropane-1-carbonyl)imidazo[1,2-a]pyridin-6-yl)-1H-pyrrole-1-carboxylate | $^1$H NMR (400 MHz, DMSO-d$_6$) δ 9.47 (s, 1H), 7.48 (dd, J = 9.1, 1.9 Hz, 1H), 7.38 (q, J = 1.6 Hz, 1H), 7.31 (d, J = 8.8 Hz, 1H), 6.62 (s, 2H), 6.32 (q, J = 1.8 Hz, 1H), 6.28 (t, J = 3.6 Hz, 1H), 5.21-5.03 (m, 1H), 2.55-2.53 (m, 2H), 1.83-1.77 (m, 1H), 1.28 (s, 9H), 1.08-1.03 (m, 1H); LCMS (electrospray) m/z 385.10 (M + H)+. | L |
| 122 | 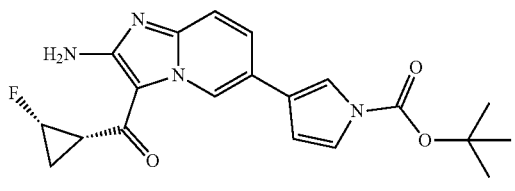<br>tert-butyl 3-(2-amino-3-((1S,2S)-2-fluorocyclopropane-1-carbonyl)imidazo[1,2-a]pyridin-6-yl)-1H-pyrrole-1-carboxylate | $^1$H NMR (400 MHz, DMSO-d$_6$) δ 9.70 (s, 1H), 7.82 (d, J = 9.1 Hz, 1H), 7.66 (s, 1H), 7.35-7.32 (m, 2H), 6.61-6.60 (m, 3H), 5.22-5.05 (m, 1H), 2.57-2.57 (m, 1H), 1.87-1.80 (m, 1H), 1.59 (s, 9H), 1.13-1.05 (m, 1H); LCMS (electrospray) m/z 385.10 (M + H)+. | L |

TABLE 1-continued

Compounds of Examples

| Ex # | Structure/Name | 1H NMR/MS (M + 1) | Synthetic Method |
|---|---|---|---|
| 123 | 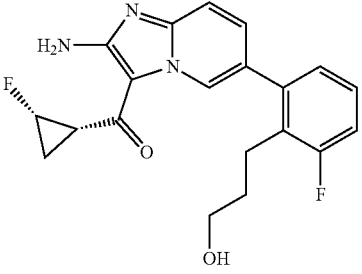<br>(2-amino-6-(3-fluoro-2-(2-hydroxypropyl)phenyl)imidazo[1,2-a]pyridin-3-yl)((1S,2S)-2-fluorocyclopropyl)methanone | $^1$H NMR (400 MHz, DMSO-d$_6$) δ 9.46 (s, 1H), 7.46 (d, J = 8.8 Hz, 1H), 7.39 (d, J = 8.2 Hz, 1H), 7.32-7.27 (m, 1H), 7.20 (t, J = 8.5 Hz, 1H), 7.09 (d, J = 6.6 Hz, 1H), 6.65 (s, 2H), 5.22-5.05 (m, 1H), 4.33 (t, J = 5.2 Hz, 1H), 3.23 (q, J = 6.0 Hz, 2H), 2.55-2.50 (m, 3H), 1.82-1.76 (m, 1H), 1.55-1.50 (m, 2H), 1.07-1.03 (m, 1H); LCMS (electrospray) m/z 372.10 (M + H)+. | L |
| 124 | 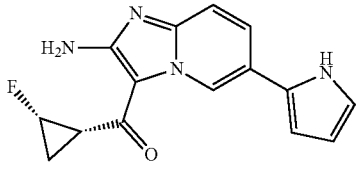<br>(2-amino-6-(1H-pyrrol-2-yl)imidazo[1,2-a]pyridin-3-yl)((1S,2S)-2-fluorocyclopropyl)methanone | $^1$H NMR (400 MHz, DMSO-d$_6$) δ 11.45 (s, 1H), 9.76 (s, 1H), 7.76 (dd, J = 9.1, 1.9 Hz, 1H), 7.37 (d, J = 9.3 Hz, 1H), 6.85-6.85 (m, 1H), 6.59 (s, 2H), 6.43 (s, 1H), 6.13-6.12 (m, 1H), 5.26-5.09 (m, 1H), 2.53-2.62 (m, 1H), 1.90-1.90 (m, 1H), 1.10-1.10 (m, 1H); LCMS (electrospray) m/z 285.10 (M + H)+. | L |
| 125 | 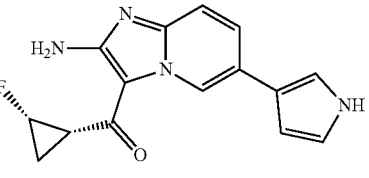<br>(2-amino-6-(1H-pyrrol-2-yl)imidazo[1,2-a]pyridin-3-yl)((1S,2S)-2-fluorocyclopropyl)methanone | $^1$H NMR (400 MHz, DMSO-d$_6$) δ 11.09 (s, 1H), 9.70 (s, 1H), 7.83 (d, J = 9.3 Hz, 1H), 7.39 (d, J = 8.8 Hz, 1H), 7.27 (s, 1H), 6.86 (s, 1H), 6.71 (s, 2H), 6.39 (s, 1H), 5.26-5.08 (m, 1H), 2.60-2.56 (m, 1H), 1.91-1.85 (m, 1H), 1.14-1.10 (m, 1H); LCMS (electrospray) m/z 285.10 (M + H)+. | L |
| 126 | 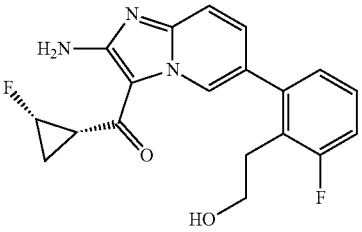<br>(2-amino-6-(3-fluoro-2-(2-hydroxyethyl)phenyl)imidazo[1,2-a]pyridin-3-yl)((1S,2S)-2-fluorocyclopropyl)methanone | $^1$H NMR (400 MHz, DMSO-d$_6$) δ 9.49 (s, 1H), 7.55 (dd, J = 9.1, 1.9 Hz, 1H), 7.43 (d, J = 9.9 Hz, 1H), 7.37-7.32 (m, 1H), 7.25 (t, J = 9.1 Hz, 1H), 7.13 (d, J = 6.6 Hz, 1H), 6.69 (s, 2H), 5.25-5.08 (m, 1H), 4.71 (t, J = 5.5 Hz, 1H), 3.50-3.40 (m, 2H), 2.74 (t, J = 7.4 Hz, 2H), 2.59-2.56 (m, 1H), 1.86-1.80 (m, 1H), 1.12-1.05 (m, 1H); LCMS (electrospray) m/z 358.10 (M + H)+. | L |

TABLE 1-continued

Compounds of Examples

| Ex # | Structure/Name | 1H NMR/MS (M + 1) | Synthetic Method |
|---|---|---|---|
| 127 | 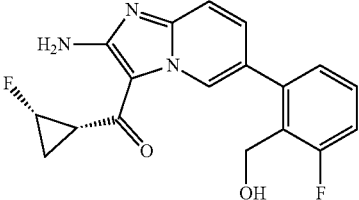<br>(2-amino-6-(3-fluoro-2-(hydroxymethyl)phenyl)imidazo[1,2-a]pyridin-3-yl)((1S,2S)-2-fluorocyclopropyl)methanone | $^1$H NMR (400 MHz, DMSO-d$_6$) δ 9.61 (s, 1H), 7.67 (dd, J = 8.8, 1.6 Hz, 1H), 7.48-7.43 (m, 2H), 7.30-7.21 (m, 2H), 6.70 (s, 2H), 5.26-5.06 (m, 2H), 4.39 (d, J = 4.4 Hz, 2H), 2.59-2.59 (m, 1H), 1.87-1.81 (m, 1H), 1.14-1.07 (m, 1H); LCMS (electrospray) m/z 344.10 (M + H)+. | L |
| 128 | 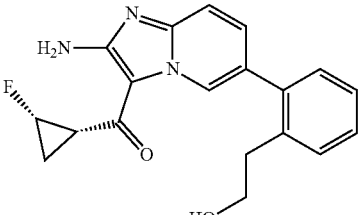<br>(2-amino-6-(2-(2-hydroxyethyl)phenyl)imidazo[1,2-a]pyridin-3-yl)((1S,2S)-2-fluorocyclopropyl)methanone | $^1$H NMR (400 MHz, DMSO-d$_6$) δ 9.44 (s, 1H), 7.48 (dd, J = 9.1, 1.9 Hz, 1H), 7.39-7.31 (m, 3H), 7.28-7.20 (m, 2H), 6.62 (s, 2H), 5.22-5.05 (m, 1H), 4.56 (t, J = 5.5 Hz, 1H), 3.44 (q, J = 6.6 Hz, 2H), 2.68 (t, J = 7.4 Hz, 2H), 2.56-2.52 (m, 1H), 1.82-1.76 (m, 1H), 1.07-1.03 (m, 1H); LCMS (electrospray) m/z 340.10 (M + H)+. | L |
| 129 | 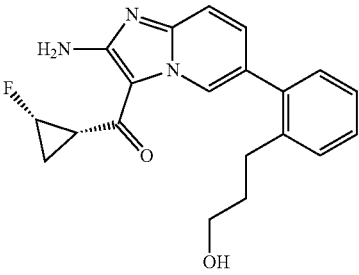<br>(2-amino-6-(2-(3-hydroxypropyl)phenyl)imidazo[1,2-a]pyridin-3-yl)((1S,2S)-2-fluorocyclopropyl)methanone | $^1$H NMR (400 MHz, DMSO-d$_6$) δ 9.44 (s, 1H), 7.45 (dd, J = 8.8, 1.6 Hz, 1H), 7.38-7.31 (m, 3H), 7.26-7.19 (m, 2H), 6.62 (s, 2H), 5.23-5.02 (m, 1H), 4.32 (t, J = 5.2 Hz, 1H), 3.27-3.22 (m, 2H), 2.58-2.50 (m, 3H), 1.83-1.75 (m, 1H), 1.57-1.50 (m, 2H), 1.10-1.03 (m, 1H); LCMS (electrospray) m/z 354.10 (M + H)+. | L |
| 130 | 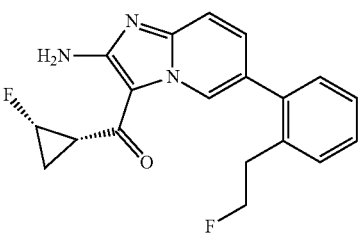<br>(2-amino-6-(2-(2-fluoroethyl)phenyl)imidazo[1,2-a]pyridin-3-yl)((1S,2S)-2-fluorocyclopropyl)methanone | $^1$H NMR (400 MHz, DMSO-d$_6$) δ 9.45 (s, 1H), 7.50-7.38 (m, 4H), 7.36-7.25 (m, 2H), 6.64 (s, 2H), 5.21-5.04 (m, 1H), 4.52 (dt, J = 47.3, 6.6 Hz, 2H), 2.93 (dt, J = 23.6, 6.3 Hz, 2H), 2.55-2.50 (m, 1H), 1.82-1.76 (m, 1H), 1.08-1.03 (m, 1H); LCMS (electrospray) m/z 342.10 (M + H)+. | L |

TABLE 1-continued

Compounds of Examples

| Ex # | Structure/Name | 1H NMR/MS (M + 1) | Synthetic Method |
|---|---|---|---|
| 131 | 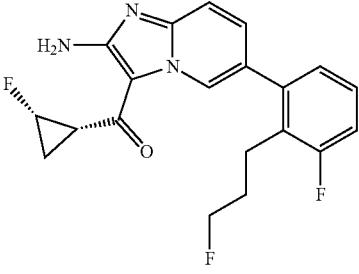<br>(2-amino-6-(3-fluoro-2-(3-fluoropropyl)phenyl)imidazo[1,2-a]pyridin-3-yl)((1S,2S)-2-fluorocyclopropyl)methanone | $^1$H NMR (400 MHz, DMSO-d$_6$) δ 9.51 (s, 1H), 7.52-7.41 (m, 2H), 7.39-7.24 (m, 2H), 7.15 (d, J = 6.6 Hz, 1H), 6.69 (s, 2H), 5.25-5.07 (m, 1H), 4.32 (dt, J = 47.3, 5.8 Hz, 2H), 2.69-2.65 (m, 2H), 2.59-2.56 (m, 1H), 1.86-1.74 (m, 3H), 1.10-1.06 (m, 1H); LCMS (electrospray) m/z 374.10 (M + H)+. | L |
| 132 | 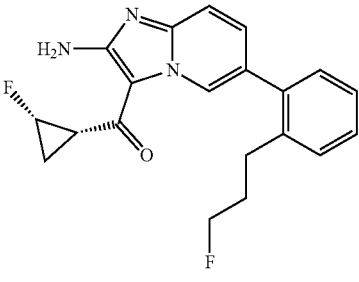<br>(2-amino-6-(2-(3-fluoropropyl)phenyl)imidazo[1,2-a]pyridin-3-yl)((1S,2S)-2-fluorocyclopropyl)methanone | $^1$H NMR (400 MHz, DMSO-d$_6$) δ 9.46 (s, 1H), 7.46 (dd, J = 9.1, 1.9 Hz, 1H), 7.39-7.35 (m, 3H), 7.29-7.22 (m, 2H), 6.63 (s, 2H), 5.21-5.04 (m, 1H), 4.35 (t, J = 5.8 Hz, 1H), 4.23 (t, J = 6.0 Hz, 1H), 2.63 (t, J = 8.0 Hz, 2H), 2.54-2.54 (m, 1H), 1.82-1.72 (m, 3H), 1.06-1.03 (m, 1H); LCMS (electrospray) m/z 356.10 (M + H)+. | L |
| 133 | 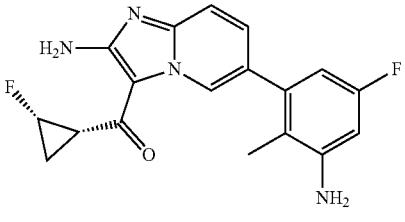<br>(2-amino-6-(3-amino-5-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.40 (s, 1H), 7.41 (dd, J = 9.1, 1.9 Hz, 1H), 7.35 (d, J = 9.9 Hz, 1H), 6.62 (s, 2H), 6.44 (dd, J = 11.5, 2.7 Hz, 1H), 6.24 (dd, J = 9.3, 2.7 Hz, 1H), 5.34 (s, 2H), 5.21-5.04 (m, 1H), 2.53-2.53 (m, 1H), 1.87 (s, 3H), 1.82-1.76 (m, 1H), 1.07-1.03 (m, 1H); LCMS (electrospray) m/z 343.10 (M + H)+. | B |
| 134 | 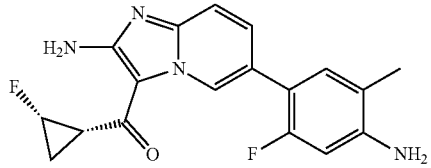<br>(2-amino-6-(4-amino-2-fluoro-5-methylphenyl)imidazo[1,2-a]pyridin-3-yl)((1S,2S)-2-fluorocyclopropyl)methanone | $^1$H NMR (400 MHz, DMSO-d$_6$) δ 9.64 (s, 1H), 7.57 (d, J = 9.3 Hz, 1H), 7.34 (d, J = 8.8 Hz, 1H), 7.07 (d, J = 9.3 Hz, 1H), 6.58 (s, 2H), 6.46 (d, J = 13.2 Hz, 1H), 5.35 (s, 2H), 5.23-5.02 (m, 1H), 2.54-2.51 (m, 1H), 2.04 (s, 3H), 1.85-1.78 (m, 1H), 1.09-1.03 (m, 1H); LCMS (electrospray) m/z 343.10 (M + H)+. | B |

TABLE 1-continued

Compounds of Examples

| Ex # | Structure/Name | 1H NMR/MS (M + 1) | Synthetic Method |
|---|---|---|---|
| 135 | methyl 2-amino-6-(3-fluoro-2-methylphenyl)imidazo[1,2-a]pyridine-3-carboxylate | $^1$H NMR (400 MHz, DMSO-$d_6$) δ 8.93 (br s, 1H), 7.48-7.43 (m, 1H), 7.42-7.38 (m, 1H), 7.37-7.30 (m, 1H), 7.27-7.21 (m, 1H), 7.17 (d, J = 7.7 Hz, 1H), 6.40 (s, 2H), 3.82 (s, 3H), 2.17 (d, J = 2.3 Hz, 3H); LCMS (electrospray) m/z 300.10 (M + H)+ | P |
| 136 | (2-amino-6-(3-fluoro-2-(2-fluoroethyl)phenyl)imidazo[1,2-a]pyridin-3-yl)((1S,2S)-2-fluorocyclopropyl)methanone | $^1$H NMR (400 MHz, DMSO-$d_6$) δ 9.46 (s, 1H), 7.47 (dd, J = 8.8, 1.6 Hz, 1H), 7.41-7.35 (m, 2H), 7.27 (dd, J = 9.6, 8.0 Hz, 1H), 7.14 (d, J = 7.7 Hz, 1H), 6.66 (s, 2H), 5.23-5.02 (m, 1H), 4.47 (dt, J = 47.1, 6.5 Hz, 2H), 2.96 (dt, J = 22.0, 6.3 Hz, 2H), 2.55-2.50 (m, 1H), 1.84-1.74 (m, 1H), 1.10-1.02 (m, 1H); LCMS (electrospray) m/z 360.10 (M + H)+. | L |
| 137 | tert-butyl (2-(2-amino-3-((1S,2S)-2-fluorocyclopropane-1-carbonyl)imidazo[1,2-a]pyridin-6-yl)benzyl)carbamate | $^1$H NMR (400 MHz, DMSO-$d_6$) δ 9.44 (s, 1H), 7.50 (d, J = 8.8 Hz, 1H), 7.41-7.36 (m, 3H), 7.33-7.29 (m, 2H), 7.24 (d, J = 7.1 Hz, 1H), 6.62 (s, 2H), 5.22-5.05 (m, 1H), 4.06 (d, J = 5.5 Hz, 2H), 2.54-2.52 (m, 1H), 1.82-1.77 (m, 1H), 1.30 (s, 9H), 1.20-1.12 (m, 2H), 1.08-1.03 (m, 1H); LCMS (electrospray) m/z 425.20 (M + H)+. | L |
| 138 | (2-amino-6-(2-(aminomethyl)phenyl)imidazo[1,2-a]pyridin-3-yl)((1S,2S)-2-fluorocyclopropyl)methanone | $^1$H NMR (400 MHz, DMSO-$d_6$) δ 9.50 (s, 1H), 7.62 (d, J = 6.6 Hz, 1H), 7.54 (dd, J = 8.8, 1.6 Hz, 1H), 7.46 (td, J = 7.6, 1.5 Hz, 1H), 7.41-7.38 (m, 2H), 7.32 (d, J = 7.7 Hz, 1H), 6.65 (s, 2H), 6.50 (s, 2H), 5.24-5.03 (m, 1H), 3.85 (s, 2H), 2.56-2.53 (m, 1H), 1.83-1.76 (m, 1H), 1.09-1.03 (m, 1H); LCMS (electrospray) m/z 326.10 (M + H)+. | L |

TABLE 1-continued

Compounds of Examples

| Ex # | Structure/Name | 1H NMR/MS (M + 1) | Synthetic Method |
|---|---|---|---|
| 139 | 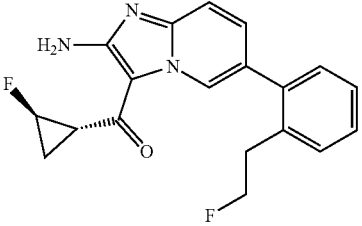<br>(2-amino-6-(2-(2-fluoroethyl)phenyl)imidazo[1,2-a]pyridin-3-yl)((1S,2R)-2-fluorocyclopropyl)methanone | ¹H NMR (400 MHz, DMSO-d₆) δ 9.49-9.34 (m, 1H), 7.52-7.48 (m, 1H), 7.47-7.43 (m, 2H), 7.42-7.40 (m, 1H), 7.39-7.33 (m, 1H), 7.33-7.25 (m, 1H), 6.73-6.60 (m, 2H) 5.10-4.87 (m, 1H), 4.63-4.44 (m, 2H), 3.09-3.01 (m, 1H), 3.00-2.90 (m, 2H), 1.66-1.53 (m, 1H), 1.34 (dq, J = 12.73, 6.27 Hz, 1H); LCMS (electrospray) m/z 342.10 (M + H)+ | L |
| 140 | 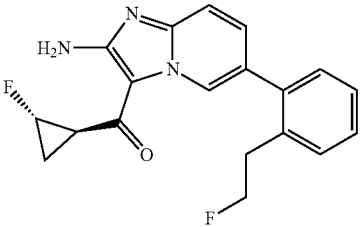<br>(2-amino-6-(2-(2-fluoroethyl)phenyl)imidazo[1,2-a]pyridin-3-yl)((1R,2S)-2-fluorocyclopropyl)methanone | ¹H NMR (400 MHz, DMSO-d₆) δ 9.51-9.33 (m, 1H), 7.53-7.47 (m, 1H), 7.47-7.44 (m, 1H), 7.44-7.42 (m, 1H), 7.41-7.38 (m, 1H), 7.34 (td, J = 7.32, 1.25 Hz, 1H), 7.29-7.25 (m, 1H), 6.75-6.57 (m, 2H), 5.10-4.88 (m, 1H), 4.62-4.46 (m, 2H), 3.10-3.01 (m, 1H), 3.01-2.90 (m, 2H), 1.66-1.53 (m, 1H), 1.34 (dq, J = 12.65, 6.25 Hz, 1H); LCMS (electrospray) m/z 342.00 (M + H)+ | L |
| 141 | 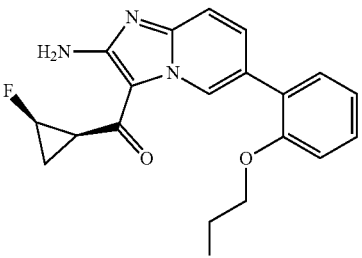<br>(2-amino-6-(3-fluoro-2-(2-fluoroethoxy)phenyl)imidazo[1,2-a]pyridin-3-yl)((1R,2R)-2-fluorocyclopropyl)methanone | ¹H NMR (400 MHz, DMSO-d₆) δ 9.86-9.69 (m, 1H), 8.48 (s, 1H) 7.70 (dd, J = 9.13, 1.88 Hz, 1H), 7.48-7.18 (m, 5H) 6.68 (br s, 2H) 5.40-4.99 (m, 1H), 4.64-4.35 (m, 2H), 4.26-4.03 (m, 2H), 1.96-1.74 (m, 1H), 1.27-0.95 (m, 2H); LCMS (electrospray) m/z 376.10 (M + H)+ | L |
| 142 | 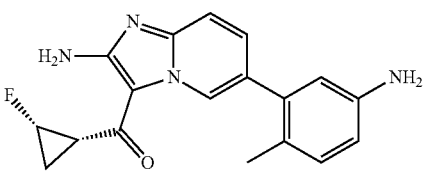<br>(2-amino-6-(5-amino-2-methylphenyl)imidazo[1,2-a]pyridin-3-yl)((1S,2S)-2-fluorocyclopropyl)methanone | ¹H NMR (400 MHz, DMSO-d₆) δ 9.45 (s, 1H), 7.45 (dd, J = 8.8, 2.2 Hz, 1H), 7.34 (d, J = 8.2 Hz, 1H), 6.92 (d, J = 8.2 Hz, 1H), 6.59 (s, 2H), 6.49 (dd, J = 8.0, 2.5 Hz, 1H), 6.46 (d, J = 2.2 Hz, 1H), 5.21-5.02 (m, 1H), 4.97 (s, 2H), 2.55-2.51 (m, 1H), 2.05 (s, 3H), 1.83-1.77 (m, 1H), 1.08-1.03 (m, 1H); LCMS (electrospray) m/z 325.10 (M + H)+. | B |

TABLE 1-continued

Compounds of Examples

| Ex # | Structure/Name | 1H NMR/MS (M + 1) | Synthetic Method |
|---|---|---|---|
| 143 | 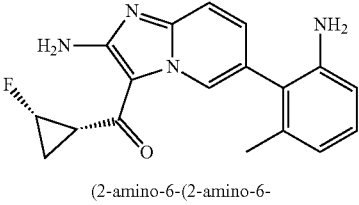<br>(2-amino-6-(2-amino-6-methylphenyl)imidazo[1,2-a]pyridin-3-yl)((1S,2S)-2-fluorocyclopropyl)methanone | $^1$H NMR (400 MHz, DMSO-$d_6$) δ 9.31 (s, 1H), 7.42 (d, J = 8.8 Hz, 1H), 7.26 (d, J = 8.8 Hz, 1H), 6.98-6.94 (m, 1H), 6.58 (d, J = 7.7 Hz, 3H), 6.49 (d, J = 7.7 Hz, 1H), 5.24-5.07 (m, 1H), 4.61 (s, 2H), 2.55-2.53 (m, 1H), 1.92 (d, J = 5.5 Hz, 3H), 1.84-1.79 (m, 1H), 1.10-1.05 (m, 1H); LCMS (electrospray) m/z 325.10 (M + H)+. | B |
| 144 | 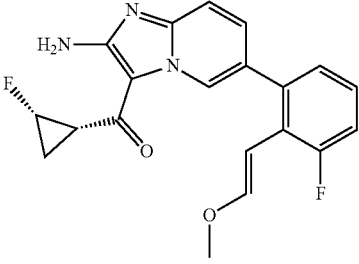<br>(2-amino-6-(3-fluoro-2-((E)-2-methoxyvinyl)phenyl)imidazo[1,2-a]pyridin-3-yl)((1S,2S)-2-fluorocyclopropyl)methanone | $^1$H NMR (400 MHz, DMSO-$d_6$) δ 9.52 (s, 1H), 7.46 (dd, J = 9.1, 1.9 Hz, 1H), 7.38 (d, J = 8.5 Hz, 1H), 7.25-7.20 (m, 2H), 7.15-7.13 (m, 1H), 7.03 (dd, J = 12.9, 1.4 Hz, 1H), 6.65 (s, 2H), 5.42 (d, J = 13.2 Hz, 1H), 5.22-5.02 (m, 1H), 3.46 (s, 3H), 2.53 (q, J = 7.7 Hz, 1H), 1.80 (d, J = 23.6 Hz, 1H), 1.07 (t, J = 6.6 Hz, 1H); LCMS (electrospray) m/z 370.10 (M + H)+. | B |
| 145 | 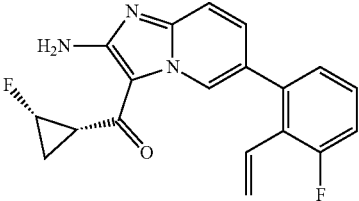<br>(2-amino-6-(3-fluoro-2-vinylphenyl)imidazo[1,2-a]pyridin-3-yl)((1S,2S)-2-fluorocyclopropyl)methanone | $^1$H NMR (400 MHz, DMSO-$d_6$) δ 9.52 (s, 1H), 7.64-7.55 (m, 1H), 7.48-7.39 (m, 3H), 7.32 (dd, J = 10.7, 8.0 Hz, 1H), 7.23 (d, J = 6.6 Hz, 1H), 6.70 (s, 2H), 6.44 (dd, J = 17.9, 11.8 Hz, 1H), 5.70 (d, J = 17.6 Hz, 1H), 5.50 (d, J = 11.5 Hz, 1H), 5.26-5.06 (m, 1H), 2.57 (t, J = 7.7 Hz, 1H), 1.88-1.80 (m, 1H), 1.10 (qd, J = 6.3, 2.6 Hz, 1H) LCMS (electrospray) m/z 340.10 (M + H)+. | B |
| 146 | 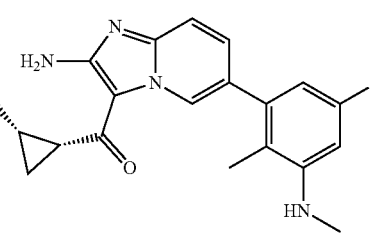<br>(2-amino-6-(5-fluoro-2-methyl-3-(methylamino)phenyl)imidazo[1,2-a]pyridin-3-yl)((1S,2S)-2-fluorocyclopropyl)methanone | $^1$H NMR (400 MHz, DMSO-$d_6$) δ 9.45 (s, 1H), 7.48-7.36 (m, 2H), 6.66 (s, 2H), 6.37-6.27 (m, 2H), 5.57 (d, J = 3.0 Hz, 1H), 5.30-5.05 (m, 1H), 2.76 (d, J = 4.4 Hz, 3H), 2.64-2.52 (m, 1H), 1.92 (d, J = 6.6 Hz, 3H), 1.90-1.76 (m, 1H), 1.13-1.04 (m, 1H); LCMS (electrospray) m/z 357.10 (M + H)+. | B |

TABLE 1-continued

Compounds of Examples

| Ex # | Structure/Name | 1H NMR/MS (M + 1) | Synthetic Method |
|---|---|---|---|
| 147 | 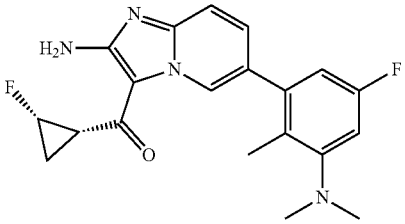<br>(2-amino-6-(3-(dimethylamino)-5-fluoro-2-methylphenyl)imidazo[1,2-a]pyridin-3-yl)((1S,2S)-2-fluorocyclopropyl)methanone | $^1$H NMR (400 MHz, DMSO-d$_6$) δ 9.51 (s, 1H), 7.55 (dd, J = 9.1, 1.9 Hz, 1H), 7.41 (d, J = 9.9 Hz, 1H), 6.92 (dd, J = 11.3, 2.5 Hz, 1H), 6.82 (dd, J = 9.1, 2.5 Hz, 1H), 6.68 (s, 2H), 5.34-5.01 (m, 1H), 2.71 (d, J = 14.8 Hz, 6H), 2.64-2.53 (m, 1H), 2.13 (d, J 7.4 Hz, 3H), 1.93-1.75 (m, 1H), 1.16-0.99 (m, 1H); LCMS (electrospray) m/z 371.15 (M + H)+. | B |
| 148 | 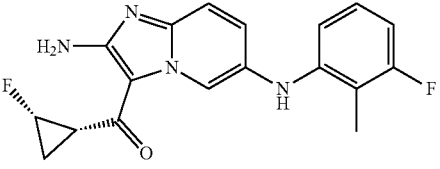<br>(2-amino-6-((3-fluoro-2-methylphenyl)amino)imidazo[1,2-a]pyridin-3-yl)((1S,2S)-2-fluorocyclopropyl)methanone | $^1$H NMR (400 MHz, DMSO-d$_6$) δ 9.46-9.28 (m, 1H), 7.57 (s, 1H) 7.37-7.33 (m, 1H) 7.33-7.29 (m, 1H), 7.09-7.02 (m, 1H), 6.74-6.70 (m, 1H), 6.68-6.65 (m, 1H), 6.42 (br s, 1H), 5.25-5.01 (m, 1H), 2.12 (d, J = 1.59 Hz, 3H), 1.88-1.75 (m, 1H), 1.14-1.02 (m, 2H); LCMS (electrospray) m/z 343.10 (M + H)+ | Q |
| 149 | 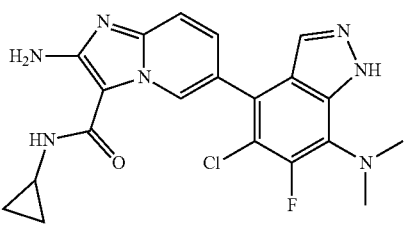<br>2-amino-6-(5-chloro-7-(dimethylamino)-6-fluoro-1H-indazol-4-yl)-N-cyclopropylimidazo[1,2-a]pyridine-3-carboxamide | $^1$H NMR (400 MHz, DMSO-d$_6$) δ 13.52 (br s, 1H) 9.38 (s, 1H) 7.90 (s, 1H) 7.43 (m, 2H) 7.27 (br d, J = 2.63 Hz, 1H) 6.03 (s, 2H) 3.00 (br s, 6H) 2.77 (m, 1H) 0.62-0.69 (m, 2H) 0.53-0.60 (m, 2H); LCMS (electrospray) m/z 428.10 (M + H)+ | L |
| 150 | 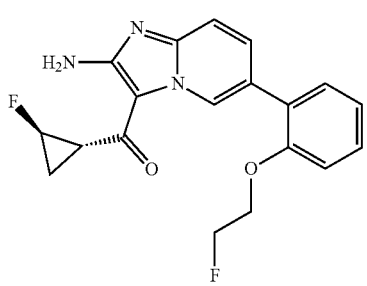<br>(2-amino-6-(3-fluoro-2-(2-fluoroethoxy)phenyl)imidazo[1,2-a]pyridin-3-yl)((1S,2R)-2-fluorocyclopropyl)methanone | $^1$H NMR (400 MHz, DMSO-d$_6$) δ 9.89-9.54 (m, 1H), 7.70 (dd, J = 9.07, 1.94 Hz, 1H), 7.51-7.15 (m, 5H), 6.70 (br s, 2H), 5.16-4.84 (m, 1H), 4.63-4.39 (m, 2H), 4.22-4.02 (m, 2H), 3.11-2.95 (m, 2H), 1.84-1.54 (m, 1H), 1.36 (dd, J = 12.69, 6.44 Hz, 1H); LCMS (electrospray) m/z 376.10 (M + H)+ | L |

TABLE 1-continued

Compounds of Examples

| Ex # | Structure/Name | 1H NMR/MS (M + 1) | Synthetic Method |
|---|---|---|---|
| 151 | (3S,4R)-4-methyltetrahydrofuran-3-yl-2-amino-6-(5-chloro-6-fluoro-7-(methylthio)-1H-indazol-4-yl)imidazo[1,2-a]pyridine-3-carboxylate | $^1$H NMR (400 MHz, DMSO-$d_6$) δ 13.82 (s, 1H) 9.15 (s, 1H) 8.08 (s, 1H) 7.64 (d, J = 9.11, 1H) 7.53 (d, J = 9.05 Hz, 1H) 6.29-6.56 (m, 2H) 5.01-5.10 (m, 1H) 3.80-4.03 (m, 4H) 2.56-2.64 (m, 4H) 1.05 (d, J = 7.09 Hz, 3H); LCMS (electrospray) m/z 476.00 (M + H)+ | R |
| 152 | (2-amino-5-(1H-indol-4-yl)pyrazolo[1,5-a]pyridin-3-yl)(cyclopropyl)methanone | $^1$H NMR (400 MHz, DMSO-$d_6$) δ 11.41 (s, 1H), 8.60 (d, J = 7.1 Hz, 1H), 8.11 (d, J = 1.1 Hz, 1H), 7.50 (q, J = 2.6 Hz, 2H), 7.29-7.21 (m, 3H), 6.64 (s, 1H), 6.58 (s, 2H), 2.54-2.52 (m, 1H), 1.00-0.97 (m, 2H), 0.94-0.91 (m, 2H) | S |
| 153 | (2-amino-5-(6-fluoro-5-methyl-1H-indazol-4-yl)pyrazolo[1,5-a]pyridin-3-yl)(cyclopropyl)methanone | $^1$H NMR (400 MHz, DMSO-$d_6$) δ 13.23 (s, 1H), 8.66 (d, J = 6.6 Hz, 1H), 7.95 (s, 1H), 7.81 (s, 1H), 7.42 (d, J = 9.9 Hz, 1H), 7.02 (dd, J = 7.1, 1.6 Hz, 1H), 6.66 (s, 2H), 2.49-2.43 (m, 1H), 2.24 (d, J = 2.7 Hz, 3H), 0.95 (t, J = 3.8 Hz, 2H), 0.92-0.82 (m, 2H) | S |
| 154 | (2-amino-5-(3-fluoro-2-methylphenyl)pyrazolo[1,5-a]pyridin-3-yl)(cyclopropyl)methanone | $^1$H NMR (400 MHz, DMSO-$d_6$) δ 8.59 (d, J = 6.6 Hz, 1H), 7.85 (s, 1H), 7.35 (q, J = 7.1 Hz, 1H), 7.31-7.15 (m, 2H), 6.97 (dd, J = 7.1, 1.6 Hz, 1H), 6.64 (s, 2H), 2.63-2.52 (m, 1H), 2.21 (d, J = 2.2 Hz, 3H), 1.03-0.94 (m, 2H), 0.93-0.82 (m, 2H) | S |

TABLE 1-continued

Compounds of Examples

| Ex # | Structure/Name | 1H NMR/MS (M + 1) | Synthetic Method |
|---|---|---|---|
| 155 | 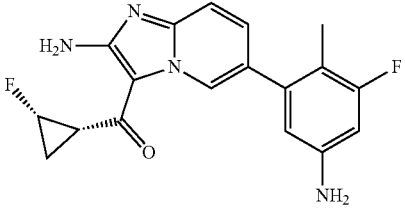<br>(2-amino-6-(5-amino-3-fluoro-2-methylphenyl)imidazo[1,2-a]pyridin-3-yl)((1S,2S)-2-fluorocyclopropyl)methanone | ¹H NMR (400 MHz, DMSO-d₆) δ 9.50 (s, 1H), 7.48 (dd, J = 9.1, 1.9 Hz, 1H), 7.39 (d, J = 8.2 Hz, 1H), 6.66 (s, 2H), 6.42-6.30 (m, 2H), 5.33 (s, 2H), 5.28-5.01 (m, 1H), 2.66-2.52 (m, 1H), 1.96 (d, J = 2.2 Hz, 3H), 1.91-1.75 (m, 1H), 1.14-1.00 (m, 1H); LCMS (electrospray) m/z 343.10 (M + H)+ | B |
| 156 | 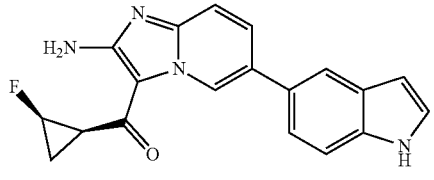<br>(2-amino-6-(1H-indol-5-yl)imidazo[1,2-a]pyridin-3-yl)((1R,2R)-2-fluorocyclopropyl)methanone | ¹H NMR (400 MHz, DMSO- d₆) δ 11.21 (s, 1H), 9.85 (s, 1H), 7.86 (dd, J = 9.1, 1.9 Hz, 1H), 7.81 (d, J = 1.6 Hz, 1H), 7.51 (d, J = 8.8 Hz, 1H), 7.44-7.40 (m, 2H), 7.37 (dd, J = 8.5, 1.9 Hz, 1H), 6.60 (s, 2H), 6.51 (t, J = 1.9 Hz, 1H), 5.28-5.08 (m, 1H), 2.67-2.57 (m, 1H), 1.92-1.83 (m, 1H), 1.14-1.09 (m, 1H); LCMS (electrospray) m/z 335.2 (M + H)+. | L |
| 157 | 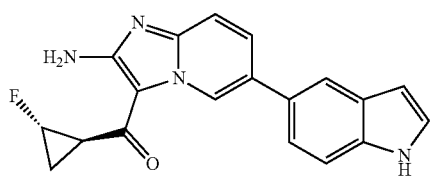<br>(2-amino-6-(1H-indol-5-yl)imidazo[1,2-a]pyridin-3-yl)((1R,2S)-2-fluorocyclopropyl)methanone | ¹H NMR (400 MHz, DMSO- d₆) δ 11.21 (s, 1H), 9.82 (s, 1H), 7.86 (dd, J = 9.1, 1.9 Hz, 1H), 7.78 (d, J = 1.6 Hz, 1H), 7.50 (d, J = 8.8 Hz, 1H), 7.44-7.40 (m, 2H), 7.37 (dd, J = 8.5, 1.9 Hz, 1H), 6.61 (s, 2H), 6.50 (t, J = 1.9 Hz, 1H), 5.12-4.94 (m, 1H), 3.12-3.05 (m, 1H), 1.65-1.57 (m, 1H), 1.40-1.36 (m, 1H); LCMS (electrospray) m/z 335.1 (M + H)+. | L |
| 158 | 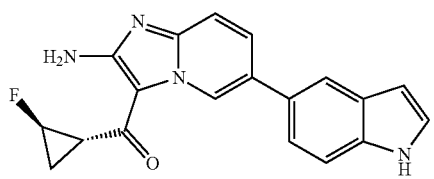<br>(2-amino-6-(1H-indol-5-yl)imidazo[1,2-a]pyridin-3-yl)((1S,2R)-2-fluorocyclopropyl)methanone | ¹H NMR (400 MHz, DMSO- d₆) δ 11.21 (s, 1H), 9.78 (s, 1H), 7.86 (dd, J = 9.1, 1.9 Hz, 1H), 7.78 (d, J = 1.6 Hz, 1H), 7.50 (d, J = 8.8 Hz, 1H), 7.44-7.39 (m, 2H), 7.34 (dd, J = 8.5, 1.9 Hz, 1H), 6.60 (s, 2H), 6.50 (s, 1h), 5.11-4.94 (m, 1H), 3.11-3.03 (m, 1H), 1.64-1.57 (m, 1H), 1.40-1.36 (m, 1H); LCMS (electrospray) m/z 335.1 (M + H)+. | L |
| 159 | 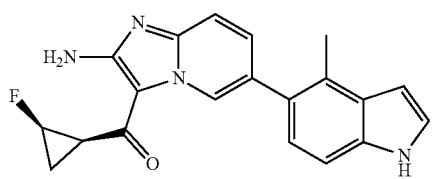<br>(2-amino-6-(4-methyl-1H-indol-5-yl)imidazo[1,2-a]pyridin-3-yl)((1R,2R)-2-fluorocyclopropyl)methanone | ¹H NMR (400 MHz, DMSO-d₆) δ 11.18 (s, 1H), 9.50 (s, 1H), 7.53 (dd, J = 9.1, 1.9 Hz, 1H), 7.41-7.38 (m, 2H), 7.31 (d, J = 8.2 Hz, 1H), 7.01 (d, J = 8.2 Hz, 1H), 6.60 (s, 2H), 6.52 (s, 1H), 5.26-5.07 (m, 1H), 2.61-2.56 (m, 1H), 2.42 (s, 3H), 1.87-1.80 (m, 1H), 1.11-1.06 (m, 1H); LCMS (electrospray) m/z 349.2 (M + H)+. | L |

TABLE 1-continued

Compounds of Examples

| Ex # | Structure/Name | 1H NMR/MS (M + 1) | Synthetic Method |
|---|---|---|---|
| 160 | 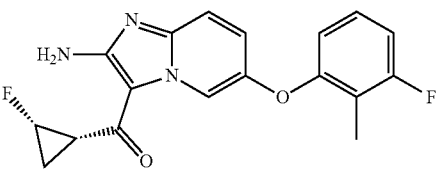<br>(2-amino-6-(3-fluoro-2-methylphenoxy)imidazo[1,2-a]pyridin-3-yl)((1S,2S)-2-fluorocyclopropyl)methanone | $^1$H NMR (400 MHz, DMSO-d$_6$) δ 9.32 (s, 1H), 7.41 (d, J = 1.6 Hz, 2H), 7.21 (dd, J = 15.0, 8.2 Hz, 1H), 7.00 (t, J = 8.8 Hz, 1H), 6.74 (d, J = 8.4 Hz, 1H), 6.57 (s, 2H), 5.23-5.03 (m, 1H), 2.58-2.56 (m, 1H), 2.19 (s, 3H), 1.85-1.77 (m, 1H), 1.12-1.06 (m, 1H); LCMS (electrospray) m/z 343.9 (M + H)+. | Q |
| 161 | 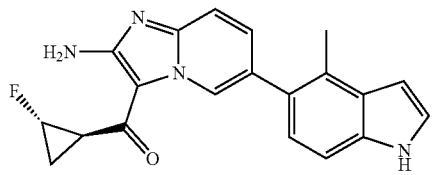<br>(2-amino-6-(4-methyl-1H-indol-5-yl)imidazo[1,2-a]pyridin-3-yl)((1R,2S)-2-fluorocyclopropyl)methanone | $^1$H NMR (400 MHz, DMSO-d$_6$) δ 11.17 (s, 1H), 9.44 (s, 1H), 7.54 (dd, J = 9.1, 1.9 Hz, 1H), 7.41-7.37 (m, 2H), 7.30 (d, J = 8.2 Hz, 1H), 6.99 (d, J = 8.2 Hz, 1H), 6.60 (s,2H), 6.52 (s, 1H), 5.08-4.91 (m, 1H), 3.09-3.00 (m, 1H), 2.40 (s, 3H), 1.63-1.55 (m, 1H), 1.37-1.32 (m, 1H); LCMS (electrospray) m/z 349.2 (M + H)+. | L |
| 162 | 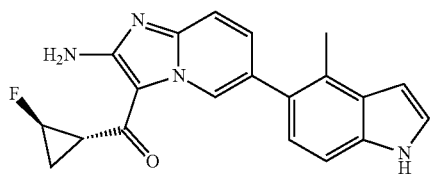<br>(2-amino-6-(4-methyl-1H-indol-5-yl)imidazo[1,2-a]pyridin-3-yl)((1S,2R)-2-fluorocyclopropyl)methanone | $^1$H NMR (400 MHz, DMSO-d$_6$) δ 11.17 (s, 1H), 9.45 (s, 1H), 7.54 (dd, J = 9.1, 1.9 Hz, 1H), 7.41-7.31 (m, 2H), 7.30 (d, J = 8.2 Hz, 1H), 6.99 (d, J = 8.2 Hz, 1H), 6.60 (s,2H), 6.52 (s, 1H), 5.07-4.91 (m, 1H), 3.09-3.00 (m, 1H), 2.40 (s, 3H), 1.64-1.56 (m, 1H), 1.37-1.32 (m, 1H); LCMS (electrospray) m/z 349.2 (M + H)+. | L |

Evaluation of Compounds

RIP2 Kinase Assay

GST-tagged recombinant human RIP2 (25 ng) is incubated with 5 µL of compounds (0.5% DMSO), 5 µL of MBP (0.5 µg/µl) and 5 µL of ATP (25 µM) in buffer (40 mM Tris, 7.5; 20 mM MgCl$_2$; 0.1 mg/ml BSA; 50 µM DTT). The assay was started by incubating the reaction mixture in a 96-well plate at 30° C. for 60 minutes. After the incubation, 25 µL ADP-Glo reagent was added, and the reaction was incubated at 30° C. for 40 minutes to stop the reaction and degrade residual ATP. The ADP product was then converted to ATP by adding 50 µL per well of detection reagent. Luminescence was detected after 30 minutes room temperature incubation with the Molecular device I3X plate reader. The IC$_{50}$ values were calculated from a series of percent inhibition values determined at a range of inhibitor concentration using software routines as implemented in the GraphPad Prism 7 software and SigmaPlot 13.0.

c-Abl Kinase Assay

ADP-Glo assay kit was purchased from Promega. Magnesium chloride (MgCl$_2$), bovine serum albumin (BSA), ethylene glycol-bis(β-aminoethyl ether)-N,N,N',N'-tetraacetic acid (EGTA), tween-20, 1,4-dithiothreitol (DTT) and dimethyl sulfoxide (DMSO) were purchased from Sigma-Aldrich. HEPES buffer was purchased from Gibco. ABL1 kinase and Abltide were purchased from Signalchem.

c-Abl kinase activity was measured by Promega's ADP-Glo™ Assay. In this assay, His-tagged recombinant human ABL1 (0.25 ng/µl) is incubated with 5 µL of compounds (0.5% DMSO), 5 µL of Abltide (0.01 µg/µl) and 5 µL of ATP (25 µM) in buffer (50 mM HEPES, 7.5; 10 mM MgCl$_2$; 1 mM EGTA; 0.05% BSA; 0.01% Tween-20; 2 mM DTT). The assay was started by incubating the reaction mixture in a 96-well plate at 30° C. for 30 min. After the incubation, 25 µL ADP-Glo reagent was added and the reaction was incubated at room temperature for 40-min to stop the reaction and degrade residual ATP. The ADP product was then converted to ATP by adding 50 µL per well of detection reagent. Luminescence was detected after 30-min room temperature incubation with the Molecular device I3X plate reader. The IC$_{50}$ values were calculated from a series of percent inhibition values determined at a range of inhibitor concentration using software routines as implemented in the GraphPad Prism 7 software and Sigma Plot 13.0.

IL-6 Secretion in BV-2 Cell

BV-2 mouse microglia cells were kindly provided from Dr. Bae in Korea Institute of Science and Technology (KIST). BV-2 cells were thawed and suspended in Dulbecco's modified eagle medium (DMEM) supplemented with 10% fetal bovine serum (FBS) and 1% Penicillin/Streptomycin. Cells were seeded into 96 well plates at 2×104 cells/well and allowed to attach for 24 hr. On the day of the experiment, various concentration of FB compounds was treated, and cells were stimulated with 10 µg/ml L18-MDP. After 24 hr incubation, supernatant was collected for cytokine assay.

Cytokine secretion was measured after 24 hr post stimulation using IL-6 ELISA kit (R&D system) as suggested by the manufacturer. Absorbance at 450 nm was measured using SpectraMax i3X microplate reader (Molecular Device). Values of media-only wells were subtracted and % inhibition for each compound concentration relative to the DMSO/L18-MDP-treated controls (100%) was calculated. The $IC_{50}$ values were calculated from a series of percent activity values using software as implemented in the Graph-Pad Prism 7 software and SigmaPlot 13.0.

Table 2 shows $IC_{50}$ values of the invented compounds which represent + for >1000 nM, ++ for 501-1000 nM, +++ for 101-500 nM, ++++ for 1-100 nM.

TABLE 2

In vitro kinase activity and IL-6 secretion in BV-2 cell.

| Example | RIP2 $IC_{50}$ (nM) | c-Abl $IC_{50}$ (nM) | IL-6 $IC_{50}$ (nM) |
|---|---|---|---|
| 1 | + | − | − |
| 2 | +++ | − | − |
| 3 | ++++ | − | + |
| 4 | + | − | − |
| 5 | ++++ | ++++ | ++ |
| 6 | +++ | − | − |
| 7 | +++ | − | − |
| 8 | +++ | − | − |
| 9 | +++ | − | − |
| 10 | + | − | − |
| 11 | ++++ | − | − |
| 12 | ++++ | − | − |
| 13 | +++ | − | − |
| 14 | ++++ | − | − |
| 15 | ++++ | − | − |
| 16 | +++ | − | − |
| 17 | +++ | − | − |
| 18 | +++ | − | − |
| 19 | +++ | − | − |
| 20 | +++ | − | − |
| 21 | +++ | − | − |
| 22 | +++ | − | − |
| 23 | ++ | − | − |
| 24 | + | − | − |
| 25 | +++ | − | − |
| 26 | +++ | − | − |
| 27 | + | − | − |
| 28 | +++ | − | − |
| 29 | +++ | − | − |
| 30 | + | − | − |
| 31 | +++ | − | − |
| 32 | ++++ | − | +++ |
| 33 | + | − | − |
| 34 | +++ | − | − |
| 35 | +++ | − | − |
| 36 | + | − | − |
| 37 | + | − | − |
| 38 | + | − | − |
| 39 | + | − | − |
| 40 | ++++ | ++++ | +++ |
| 41 | ++++ | − | +++ |
| 42 | +++ | − | − |
| 43 | +++ | − | − |
| 44 | ++++ | − | ++ |
| 45 | +++ | − | − |
| 46 | ++ | − | − |
| 47 | +++ | − | − |
| 48 | +++ | − | − |
| 49 | + | − | − |
| 50 | ++++ | − | − |
| 51 | ++++ | ++++ | +++ |
| 52 | ++ | − | − |
| 53 | +++ | − | − |
| 54 | + | − | − |
| 55 | + | − | − |
| 56 | +++ | − | − |
| 57 | ++++ | ++++ | +++ |
| 58 | ++++ | − | − |
| 59 | ++++ | − | − |
| 60 | ++++ | +++ | ++++ |
| 61 | +++ | − | − |
| 62 | +++ | − | − |
| 63 | ++++ | − | − |
| 64 | ++++ | − | +++ |
| 65 | + | − | + |
| 66 | +++ | − | − |
| 67 | ++++ | − | ++ |
| 68 | ++++ | − | +++ |
| 69 | ++++ | − | ++ |
| 70 | + | − | − |
| 71 | + | − | − |
| 72 | +++ | − | − |
| 73 | ++++ | − | +++ |
| 74 | ++++ | − | +++ |
| 75 | ++++ | − | ++ |
| 76 | ++++ | − | − |
| 77 | +++ | − | − |
| 78 | ++++ | − | − |
| 79 | ++++ | − | + |
| 80 | ++++ | − | − |
| 81 | ++++ | − | − |
| 82 | ++++ | − | + |
| 83 | ++++ | − | + |
| 84 | ++++ | − | ++ |
| 85 | ++++ | − | ++ |
| 86 | ++++ | − | + |
| 87 | + | − | − |
| 88 | +++ | − | − |
| 89 | ++++ | ++++ | +++ |
| 90 | ++++ | − | ++ |
| 91 | +++ | − | − |
| 92 | +++ | − | − |
| 93 | + | − | − |
| 94 | ++++ | − | + |
| 95 | ++++ | − | + |
| 96 | +++ | − | − |
| 97 | ++++ | − | − |
| 98 | + | − | − |
| 99 | +++ | − | − |
| 100 | ++++ | − | +++ |
| 101 | ++++ | − | ++ |
| 102 | ++++ | − | − |
| 103 | +++ | − | − |
| 104 | ++++ | ++++ | +++ |
| 105 | ++++ | ++++ | +++ |
| 106 | +++ | − | − |
| 107 | + | − | − |
| 108 | +++ | − | − |
| 109 | +++ | − | − |
| 110 | ++++ | − | ++ |
| 111 | +++ | − | − |
| 112 | + | − | − |
| 113 | ++++ | ++++ | +++ |
| 114 | ++++ | ++++ | +++ |
| 115 | ++++ | − | +++ |
| 116 | +++ | − | − |
| 117 | ++++ | − | − |
| 118 | ++++ | − | − |
| 119 | +++ | − | − |
| 120 | +++ | − | − |
| 121 | + | − | − |
| 122 | + | − | − |
| 123 | +++ | − | − |
| 124 | + | − | − |
| 125 | + | − | − |
| 126 | + | − | − |
| 127 | + | − | − |
| 128 | +++ | − | − |
| 129 | +++ | − | − |
| 130 | +++ | − | − |
| 131 | +++ | − | − |
| 132 | +++ | − | − |

TABLE 2-continued

In vitro kinase activity and IL-6 secretion in BV-2 cell.

| Example | RIP2 IC$_{50}$ (nM) | c-Abl IC$_{50}$ (nM) | IL-6 IC$_{50}$ (nM) |
|---|---|---|---|
| 133 | ++++ | − | − |
| 134 | ++++ | − | − |
| 135 | +++ | − | − |
| 136 | + | − | − |
| 137 | + | − | − |
| 138 | + | − | − |
| 139 | + | − | − |
| 140 | + | − | − |
| 141 | +++ | − | − |
| 142 | ++++ | − | − |
| 143 | + | − | − |
| 144 | +++ | − | − |
| 145 | ++++ | − | − |
| 146 | +++ | − | − |
| 147 | +++ | − | − |
| 148 | +++ | − | − |
| 149 | + | − | − |
| 150 | +++ | − | − |
| 151 | + | − | − |
| 152 | ++++ | − | +++ |
| 153 | ++++ | − | ++ |
| 154 | ++++ | − | + |
| 155 | ++++ | − | − |
| 156 | ++++ | − | − |
| 157 | ++++ | − | − |
| 158 | ++++ | − | − |
| 159 | ++++ | − | − |
| 160 | +++ | − | − |
| 161 | ++++ | − | − |
| 162 | ++++ | − | − |

−; not tested

The invention claimed is:

1. A compound of Formula (I):

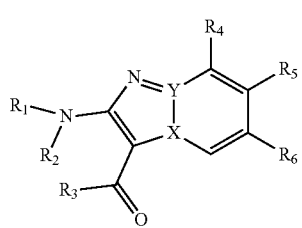

Formula I or a pharmaceutically acceptable salt thereof, wherein:

$R^1$ and $R^2$ are independently —H, $C_1$-$C_6$ alkyl, $C_3$-$C_6$ carbocyclyl, $C_1$-$C_4$ alkanoyl, —(CO) $C_3$-$C_6$ carbocyclyl, aryl, or heteroaryl, wherein each $R^1$ and $R^2$ is optionally substituted with one or more groups selected from the group consisting of halo, alkyl, hydroxyalkyl, haloalkyl, and monoalkylaminoalkyl; or $R^1$ and $R^2$ together form a 5-member heterocycle;

$R^3$ is —H, alkyl, alkoxy, cycloalkyl, heterocyclyl, aryl, heteroaryl, —O-cycloalkyl, —O— heterocyclyl, —O-aryl, —O-heteroaryl, —NR$_c$-alkyl, —NR$_c$-cycloalkyl, —NR$_c$-heterocyclyl, —NR$_c$-aryl, —NR$_c$-heteroaryl, —NR$_c$—NR$_c$ C(=O)R$_c$ or —CF$_3$, wherein $R^3$ is optionally substituted with one or more groups selected from the group consisting of halo, alkyl, hydroxyalkyl, haloalkyl, and monoalkylaminoalkyl;

$R^4$ and $R^5$ are independently —H, —OH, halo, $C_1$-$C_6$ alkyl, $C_1$-$C_6$ alkoxy, aryl, heteroaryl, heterocyclyl, heteroalkyl, amino, —SCH$_3$, or —CN;

$R^6$ is selected from the group consisting of —H, halo, $C_1$-$C_6$ alkyl, $C_1$-$C_6$ alkoxy, $C_3$-$C_6$ carbocyclyl, heterocyclyl, aryl, heteroaryl, —NR$_c$-aryl, —NR$_c$-heteroaryl, —O-aryl, —O— heteroaryl, wherein $R^6$ is optionally substituted with one or more groups selected from the group consisting of halo, hydroxyl, alkyl, alkenyl, alkynyl, haloalkyl, hydroxyalkyl, aminoalkyl, trimethylsilylethoxymethyl, morpholinyl, piperazinyl, methylpiperazinyl, alkoxyalkenyl, —NO$_2$, —NR$_a$R$_b$, —NR$_a$C(=O)R$_b$, —NR$_a$C(=O)NR$_a$R$_b$, —NR$_a$C(=O)OR$_b$, —OR$_a$, —SR$_a$, —CN, —C(=O)R$_a$, —C(=O)OR$_a$, —C(=O)NR$_a$R$_b$, —OC(=O)R$_a$, —OC(=O)OR$_a$, and —OC(=O)NR$_a$R$_b$;

$R_a$ and $R_b$ are independently —H, halo, amino, alkyl, or haloalkyl;

$R_c$ is —H, $C_1$-$C_3$ alkyl, or cyclopropyl;

X is N; and

Y is C, wherein $R^4$, $R^5$, and $R^6$ are not each —H.

2. The compound of claim 1, wherein $R^3$ is selected from the group consisting of —H, methyl, isopropyl, butyl, methoxy, pyridinyl, phenyl, cyclopropyl, cyclobutyl, pyrazolyl, azetidinyl, pyrimidinyl, pyrrolidinyl, cyclopropylamino, and indazolyl, wherein $R^3$ is optionally substituted with one or more groups selected from the group consisting of halo, alkyl, hydroxyalkyl, haloalkyl, and monoalkylaminoalkyl.

3. The compound of claim 1, wherein $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoalkyl, alkylamino, trimethylsilylethoxymethyl, morpholinyl, piperazinyl, methylpiperazinyl, and alkoxyalkenyl.

4. The compound of claim 1, which is selected from compounds of Formula (II) and pharmaceutically acceptable salts thereof:

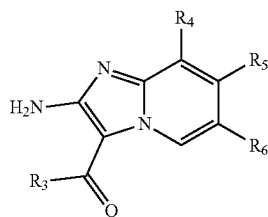

Formula II wherein $R^3$ is —H, alkyl, alkoxy, cycloalkyl, heterocyclyl, aryl, heteroaryl, —O-cycloalkyl, —O— heterocyclyl, —O-aryl, —O-heteroaryl, —NR$_c$-alkyl, —NR$_c$-cycloalkyl, —NR$_c$-heterocyclyl, —NR$_c$-aryl, —NR$_c$-heteroaryl, —NR$_c$—NR$_c$ C(=O)R$_c$ or —CF$_3$, wherein $R^3$ is optionally substituted with one or more groups selected from the group consisting of halo, alkyl, hydroxyalkyl, haloalkyl, and monoalkylaminoalkyl;

$R^4$ and $R^5$ are independently —H, —OH, halo, $C_1$-$C_6$ alkyl, $C_1$-$C_6$ alkoxy, aryl, heteroaryl, heterocyclyl, heteroalkyl, amino, —SCH$_3$, or —CN;

$R^6$ is selected from the group consisting of —H, halo, $C_1$-$C_6$ alkyl, $C_1$-$C_6$ alkoxy, $C_3$-$C_6$ carbocyclyl, heterocyclyl, aryl, heteroaryl, —NR$_c$-aryl, —NR$_c$-heteroaryl, —O-aryl, —O— heteroaryl, wherein $R^6$ is optionally substituted with one or more groups selected from the group consisting of halo, hydroxyl, alkyl, alkenyl, alkynyl, haloalkyl, hydroxyalkyl, aminoalkyl, trimethylsilylethoxymethyl, morpholinyl, piperazinyl, methylpiperazinyl, alkoxyalkenyl, —NO$_2$, —NR$_a$R$_b$, —NR$_a$C(=O)R$_b$, —NR$_a$C(=O)NR$_a$R$_b$, —NR$_a$C(=O)OR$_b$, —OR$_a$, —SR$_a$, —CN, —C(=O)R$_a$, —C(=O)OR$_a$, —C(=O)NR$_a$R$_b$, —OC(=O)R$_a$, —OC(=O)OR$_a$, and —OC(=O)NR$_a$R$_b$;

R$_a$ and R$_b$ are independently —H, halo, amino, alkyl, or haloalkyl; and

R$_c$ is —H, $C_1$-$C_3$ alkyl, or cyclopropyl.

5. The compound of claim 4, wherein $R^3$ is fluorocyclopropyl and $R^6$ is indolyl which is optionally substituted with one or more groups selected from the group consisting of halo, hydroxyl, alkyl, haloalkyl, hydroxyalkyl, aminoalkyl, and tert-butoxycarbonyl.

6. The compound of claim 5, which is selected from the group consisting of:
- (2-amino-6-(1H-indol-5-yl)imidazo[1,2-a]pyridin-3-yl)((1S,2S)-2-fluorocyclopropyl)methanone;
- (2-amino-6-(1H-indol-4-yl)imidazo[1,2-a]pyridin-3-yl)((1S,2S)-2-fluorocyclopropyl)methanone;
- (2-amino-6-(1H-indol-6-yl)imidazo[1,2-a]pyridin-3-yl)((1S,2S)-2-fluorocyclopropyl)methanone;
- (2-amino-6-(1H-indol-7-yl)imidazo[1,2-a]pyridin-3-yl)((1S,2S)-2-fluorocyclopropyl)methanone;
- (2-amino-6-(4-methyl-1H-indol-5-yl)imidazo[1,2-a]pyridin-3-yl)((1S,2S)-2-fluorocyclopropyl)methanone;
- (2-amino-8-fluoro-6-(1H-indol-5-yl)imidazo[1,2-a]pyridin-3-yl)((1S,2S)-2-fluorocyclopropyl)methanone;
- (2-amino-6-(4-chloro-1H-indol-5-yl)imidazo[1,2-a]pyridin-3-yl)((1S,2S)-2-fluorocyclopropyl)methanone;
- (2-amino-8-fluoro-6-(1H-indol-4-yl)imidazo[1,2-a]pyridin-3-yl)((1S,2S)-2-fluorocyclopropyl)methanone;
- (2-amino-6-(5-methyl-1H-indol-4-yl)imidazo[1,2-a]pyridin-3-yl)((1S,2S)-2-fluorocyclopropyl)methanone;
- (2-amino-6-(5-fluoro-1H-indol-4-yl)imidazo[1,2-a]pyridin-3-yl)((1S,2S)-2-fluorocyclopropyl)methanone;
- (2-amino-6-(5-chloro-1H-indol-3-yl)imidazo[1,2-a]pyridin-3-yl)((1S,2S)-2-fluorocyclopropyl)methanone;
- (2-amino-6-(6-fluoro-1H-indol-4-yl)imidazo[1,2-a]pyridin-3-yl)((1S,2S)-2-fluorocyclopropyl)methanone;
- (2-amino-6-(6-fluoro-5-methyl-1H-indol-4-yl)imidazo[1,2-a]pyridin-3-yl)((1S,2S)-2-fluorocyclopropyl)methanone;
- (2-amino-6-(1H-indol-5-yl)imidazo[1,2-a]pyridin-3-yl)((1R,2R)-2-fluorocyclopropyl)methanone;
- (2-amino-6-(1H-indol-5-yl)imidazo[1,2-a]pyridin-3-yl)((1R,2S)-2-fluorocyclopropyl)methanone;
- (2-amino-6-(1H-indol-5-yl)imidazo[1,2-a]pyridin-3-yl)((1S,2R)-2-fluorocyclopropyl)methanone;
- (2-amino-6-(4-methyl-1H-indol-5-yl)imidazo[1,2-a]pyridin-3-yl)((1R,2R)-2-fluorocyclopropyl)methanone;
- (2-amino-6-(4-methyl-1H-indol-5-yl)imidazo[1,2-a]pyridin-3-yl)((1R,2S)-2-fluorocyclopropyl)methanone;
- (2-amino-6-(4-methyl-1H-indol-5-yl)imidazo[1,2-a]pyridin-3-yl)((1S,2R)-2-fluorocyclopropyl)methanone;
- tert-butyl 3-(2-amino-3-((1S,2S)-2-fluorocyclopropane-1-carbonyl)imidazo[1,2-a]pyridin-6-yl)-1H-indole-1-carboxylate; and
- (2-amino-6-(1H-indol-3-yl)imidazo[1,2-a]pyridin-3-yl)((1S,2S)-2-fluorocyclopropyl)methanone.

7. The compound of claim 5, which is selected from the group consisting of:
- (2-amino-6-(4-methyl-1H-indol-5-yl)imidazo[1,2-a]pyridin-3-yl)((1S,2S)-2-fluorocyclopropyl)methanone;
- (2-amino-6-(4-chloro-1H-indol-5-yl)imidazo[1,2-a]pyridin-3-yl)((1S,2S)-2-fluorocyclopropyl)methanone;
- (2-amino-6-(1H-indol-5-yl)imidazo[1,2-a]pyridin-3-yl)((1S,2S)-2-fluorocyclopropyl)methanone;
- (2-amino-6-(6-fluoro-5-methyl-1H-indol-4-yl)imidazo[1,2-a]pyridin-3-yl)((1S,2S)-2-fluorocyclopropyl)methanone;
- (2-amino-6-(1H-indol-4-yl)imidazo[1,2-a]pyridin-3-yl)((1S,2S)-2-fluorocyclopropyl)methanone;
- (2-amino-6-(5-methyl-1H-indol-4-yl)imidazo[1,2-a]pyridin-3-yl)((1S,2S)-2-fluorocyclopropyl)methanone;
- (2-amino-6-(5-fluoro-1H-indol-4-yl)imidazo[1,2-a]pyridin-3-yl)((1S,2S)-2-fluorocyclopropyl)methanone;
- (2-amino-6-(6-fluoro-1H-indol-4-yl)imidazo[1,2-a]pyridin-3-yl)((1S,2S)-2-fluorocyclopropyl)methanone; and
- (2-amino-6-(6-fluoro-5-methyl-1H-indol-4-yl)imidazo[1,2-a]pyridin-3-yl)((1S,2S)-2-fluorocyclopropyl)methanone.

8. The compound of claim 4, wherein $R^3$ is fluorocyclopropyl, and $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoakyl, alkylamino, trimethylsilylethoxymethyl, morpholinyl, piperazyinyl, methylpieprazinyl, and alkoxyalkenyl.

9. The compound of claim 8, which is selected from the group consisting of:
- (2-amino-6-bromoimidazo[1,2-a]pyridin-3-yl)((1S,2S)-2-fluorocyclopropyl)methanone;
- (2-amino-6-(3-fluoro-2-methylphenyl)imidazo[1,2-a]pyridin-3-yl)((1S,2S)-2-fluorocyclopropyl)methanone;
- (2-amino-6-(4-fluoro-2-methylphenyl)imidazo[1,2-a]pyridin-3-yl)((1S,2S)-2-fluorocyclopropyl)methanone;
- (2-amino-6-(thiophen-2-yl)imidazo[1,2-a]pyridin-3-yl)((1S,2S)-2-fluorocyclopropyl)methanone;
- (2-amino-6-(2-(trifluoromethyl)phenyl)imidazo[1,2-a]pyridin-3-yl)((1S,2S)-2-fluorocyclopropyl)methanone;
- (2-amino-6-(3-fluoro-2-(trifluoromethyl)phenyl)imidazo[1,2-a]pyridin-3-yl)((1S,2S)-2-fluorocyclopropyl)methanone;
- (2-amino-6-(2,3-dimethylphenyl)imidazo[1,2-a]pyridin-3-yl)((1S,2S)-2-fluorocyclopropyl)methanone;
- (2-amino-6-(5-fluoro-2-methylphenyl)imidazo[1,2-a]pyridin-3-yl)((1S,2S)-2-fluorocyclopropyl)methanone;

(2-amino-6-(2,5-dimethylphenyl)imidazo[1,2-a]pyridin-3-yl)((1S,2S)-2-fluorocyclopropyl)methanone;
(2-amino-6-(2,4-dimethylphenyl)imidazo[1,2-a]pyridin-3-yl)((1S,2S)-2-fluorocyclopropyl)methanone;
(2-amino-6-(2-fluoro-6-methylphenyl)imidazo[1,2-a]pyridin-3-yl)((1S,2S)-2-fluorocyclopropyl)methanone;
(2-amino-6-(2-methyl-3-(trifluoromethyl)phenyl)imidazo[1,2-a]pyridin-3-yl)((1S,2S)-2-fluorocyclopropyl)methanone;
(2-amino-6-(4-fluoro-2-methylphenyl)imidazo[1,2-a]pyridin-3-yl)((1R,2S)-2-fluorocyclopropyl)methanone;
(2-amino-6-(2-fluoro-6-methylphenyl)imidazo[1,2-a]pyridin-3-yl)((1R,2S)-2-fluorocyclopropyl)methanone;
(2-amino-6-(furan-2-yl)imidazo[1,2-a]pyridin-3-yl)((1S,2S)-2-fluorocyclopropyl)methanone;
(2-amino-6-(5-methylthiazol-4-yl)imidazo[1,2-a]pyridin-3-yl)((1S,2S)-2-fluorocyclopropyl)methanone;
(2-amino-6-(3-methylthiophen-2-yl)imidazo[1,2-a]pyridin-3-yl)((1S,2S)-2-fluorocyclopropyl)methanone;
(2-amino-6-(thiazol-5-yl)imidazo[1,2-a]pyridin-3-yl)((1S,2S)-2-fluorocyclopropyl)methanone;
(2-amino-6-(3,4-difluoro-2-methylphenyl)imidazo[1,2-a]pyridin-3-yl)((1S,2S)-2-fluorocyclopropyl)methanone;
(2-amino-6-(1H-pyrrolo[2,3-b]pyridin-5-yl)imidazo[1,2-a]pyridin-3-yl)((1S,2S)-2-fluorocyclopropyl)methanone;
(2-amino-6-(2-chlorophenyl)imidazo[1,2-a]pyridin-3-yl)((1S,2S)-2-fluorocyclopropyl)methanone;
(2-amino-6-(3-fluoro-2-methylphenyl)imidazo[1,2-a]pyridin-3-yl)((1R,2R)-2-fluorocyclopropyl)methanone;
1-(4-(2-amino-3-((1S,2S)-2-fluorocyclopropane-1-carbonyl)imidazo[1,2-a]pyridin-6-yl)-3-methylphenyl)ethan-1-one;
(2-amino-6-(4-morpholinophenyl)imidazo[1,2-a]pyridin-3-yl)((1S,2S)-2-fluorocyclopropyl)methanone;
(2-amino-6-(4-methyl-1H-pyrrolo[2,3-b]pyridin-5-yl)imidazo[1,2-a]pyridin-3-yl)((1S,2S)-2-fluorocyclopropyl)methanone;
(2-amino-6-(4-chloro-1H-pyrrolo[2,3-b]pyridin-5-yl)imidazo[1,2-a]pyridin-3-yl)((1S,2S)-2-fluorocyclopropyl)methanone;
(2-amino-6-(3-fluoro-2-methylphenyl)imidazo[1,2-a]pyridin-3-yl)((1S,2R)-2-fluorocyclopropyl)methanone;
(2-amino-6-(3-fluoro-2-methylphenyl)imidazo[1,2-a]pyridin-3-yl)((1R,2S)-2-fluorocyclopropyl)methanone;
(2-amino-6-(2-chloro-3-fluorophenyl)imidazo[1,2-a]pyridin-3-yl)((1S,2S)-2-fluorocyclopropyl)methanone;
(2-amino-6-(2-methyl-5-(trifluoromethyl)phenyl)imidazo[1,2-a]pyridin-3-yl)((1S,2S)-2-fluorocyclopropyl)methanone;
(S)-(2-amino-6-(3-fluoro-2-methylphenyl)imidazo[1,2-a]pyridin-3-yl)(2,2-difluorocyclopropyl)methanone;
(2-amino-6-(4-(piperazin-1-yl)phenyl)imidazo[1,2-a]pyridin-3-yl)((1S,2S)-2-fluorocyclopropyl)methanone;
(2-amino-6-(4-(4-methylpiperazin-1-yl) phenyl)imidazo[1,2-a]pyridin-3-yl)((1S,2S)-2-fluorocyclopropyl)methanone;
(2-amino-6-(3-(4-methylpiperazin-1-yl) phenyl)imidazo[1,2-a]pyridin-3-yl)((1S,2S)-2-fluorocyclopropyl)methanone;
(2-amino-6-(6-fluoro-5-methyl-1H-indazol-4-yl)imidazo[1,2-a]pyridin-3-yl)((1S,2S)-2-fluorocyclopropyl)methanone;
(2-amino-6-(7-(dimethylamino)-6-fluoro-5-methyl-1H-indazol-4-yl)imidazo[1,2-a]pyridin-3-yl)((1S,2S)-2-fluorocyclopropyl)methanone;
(2-amino-6-(6-fluoro-5-methyl-7-(methylthio)-1H-indazol-4-yl)imidazo[1,2-a]pyridin-3-yl)((1S,2S)-2-fluorocyclopropyl)methanone;
(2-amino-6-(benzofuran-5-yl)imidazo[1,2-a]pyridin-3-yl)((1S,2S)-2-fluorocyclopropyl)methanone;
(2-amino-6-(5-chloro-6-fluoro-1H-indazol-4-yl)imidazo[1,2-a]pyridin-3-yl)((1S,2S)-2-fluorocyclopropyl)methanone;
(2-amino-6-(5-chloro-7-(dimethylamino)-6-fluoro-1H-indazol-4-yl)imidazo[1,2-a]pyridin-3-yl)((1S,2S)-2-fluorocyclopropyl)methanone;
(2-amino-6-(5-chloro-6-fluoro-7-(methylthio)-1H-indazol-4-yl)imidazo[1,2-a]pyridin-3-yl)((1S,2S)-2-fluorocyclopropyl)methanone;
(2-amino-6-(4-fluoro-1H-pyrrolo[2,3-b]pyridin-5-yl)imidazo[1,2-a]pyridin-3-yl)((1S,2S)-2-fluorocyclopropyl)methanone;
(2-amino-6-(3-methylisothiazol-5-yl)imidazo[1,2-a]pyridin-3-yl)((1S,2S)-2-fluorocyclopropyl)methanone;
(2-amino-6-(1H-indazol-5-yl)imidazo[1,2-a]pyridin-3-yl)((1S,2S)-2-fluorocyclopropyl)methanone;
(2-amino-6-(4-chloro-1H-indazol-5-yl)imidazo[1,2-a]pyridin-3-yl)((1S,2S)-2-fluorocyclopropyl)methanone;
(2-amino-6-(4-methyl-1H-indazol-5-yl)imidazo[1,2-a]pyridin-3-yl)((1S,2S)-2-fluorocyclopropyl)methanone;
(2-amino-8-fluoro-6-(4-methyl-1H-pyrrolo[2,3-b]pyridin-5-yl)imidazo[1,2-a]pyridin-3-yl)((1S,2S)-2-fluorocyclopropyl)methanone;
(2-amino-8-fluoro-6-(3-fluoro-2-methylphenyl)imidazo[1,2-a]pyridin-3-yl)((1S,2S)-2-fluorocyclopropyl)methanone;
(2-amino-6-(1H-benzo[d]imidazol-5-yl)imidazo[1,2-a]pyridin-3-yl)((1S,2S)-2-fluorocyclopropyl)methanone;
(2-amino-6-(4-methyl-1H-benzo[d]imidazol-5-yl)imidazo[1,2-a]pyridin-3-yl)((1S,2S)-2-fluorocyclopropyl)methanone;
(2-amino-6-(1H-pyrrolo[2,3-b]pyridin-4-yl)imidazo[1,2-a]pyridin-3-yl)((1S,2S)-2-fluorocyclopropyl)methanone;
(2-amino-6-(1,4-dimethyl-1H-pyrrolo[2,3-b]pyridin-5-yl)imidazo[1,2-a]pyridin-3-yl)((1S,2S)-2-fluorocyclopropyl)methanone;
2-amino-6-(3-fluoro-2-methylphenyl)-N-((1R,2S)-2-fluorocyclopropyl)imidazo[1,2-a]pyridine-3-carboxamide;
(2-amino-6-(1H-pyrrolo[2,3-b]pyridin-3-yl)imidazo[1,2-a]pyridin-3-yl)((1S,2S)-2-fluorocyclopropyl)methanone;
(2-amino-6-(quinolin-4-yl)imidazo[1,2-a]pyridin-3-yl)((1S,2S)-2-fluorocyclopropyl)methanone;
(2-amino-6-(quinolin-3-yl)imidazo[1,2-a]pyridin-3-yl)((1S,2S)-2-fluorocyclopropyl)methanone;
(2-amino-6-(isoquinolin-4-yl)imidazo[1,2-a]pyridin-3-yl)((1S,2S)-2-fluorocyclopropyl)methanone;
(2-amino-6-(o-tolyl)imidazo[1,2-a]pyridin-3-yl)((1S,2S)-2-fluorocyclopropyl)methanone;
(2-amino-6-(2-(2-fluoroethoxy)phenyl)imidazo[1,2-a]pyridin-3-yl)((1S,2S)-2-fluorocyclopropyl)methanone;
(2-amino-6-(3-fluoro-2-(2-fluoroethoxy)phenyl)imidazo[1,2-a]pyridin-3-yl)((1S,2S)-2-fluorocyclopropyl)methanone;
tert-butyl 2-(2-amino-3-((1S,2S)-2-fluorocyclopropane-1-carbonyl)imidazo[1,2-a]pyridin-6-yl)-1H-pyrrole-1-carboxylate;

tert-butyl 3-(2-amino-3-((1S,2S)-2-fluorocyclopropane-1-carbonyl)imidazo[1,2-a]pyridin-6-yl)-1H-pyrrole-1-carboxylate;
(2-amino-6-(3-fluoro-2-(3-hydroxypropyl)phenyl)imidazo[1,2-a]pyridin-3-yl)((1S,2S)-2-fluorocyclopropyl)methanone;
(2-amino-6-(1H-pyrrol-2-yl)imidazo[1,2-a]pyridin-3-yl)((1S,2S)-2-fluorocyclopropyl)methanone;
(2-amino-6-(1H-pyrrol-3-yl)imidazo[1,2-a]pyridin-3-yl)((1S,2S)-2-fluorocyclopropyl)methanone;
(2-amino-6-(3-fluoro-2-(2-hydroxyethyl) phenyl)imidazo[1,2-a]pyridin-3-yl)((1S,2S)-2-fluorocyclopropyl)methanone;
(2-amino-6-(3-fluoro-2-(hydroxymethyl) phenyl)imidazo[1,2-a]pyridin-3-yl)((1S,2S)-2-fluorocyclopropyl)methanone;
(2-amino-6-(2-(2-hydroxyethyl) phenyl)imidazo[1,2-a]pyridin-3-yl)((1S,2S)-2-fluorocyclopropyl)methanone;
(2-amino-6-(2-(3-hydroxypropyl)phenyl)imidazo[1,2-a]pyridin-3-yl)((1S,2S)-2-fluorocyclopropyl)methanone;
(2-amino-6-(2-(2-fluoroethyl)phenyl)imidazo[1,2-a]pyridin-3-yl)((1S,2S)-2-fluorocyclopropyl)methanone;
(2-amino-6-(3-fluoro-2-(3-fluoropropyl)phenyl)imidazo[1,2-a]pyridin-3-yl)((1S,2S)-2-fluorocyclopropyl)methanone;
(2-amino-6-(2-(3-fluoropropyl)phenyl)imidazo[1,2-a]pyridin-3-yl)((1S,2S)-2-fluorocyclopropyl)methanone;
(2-amino-6-(3-amino-5-fluoro-2-methylphenyl)imidazo[1,2-a]pyridin-3-yl)((1S,2S)-2-fluorocyclopropyl)methanone;
(2-amino-6-(4-amino-2-fluoro-5-methylphenyl)imidazo[1,2-a]pyridin-3-yl)((1S,2S)-2-fluorocyclopropyl)methanone;
(2-amino-6-(3-fluoro-2-(2-fluoroethyl) phenyl)imidazo[1,2-a]pyridin-3-yl)((1S,2S)-2-fluorocyclopropyl)methanone;
tert-butyl (2-(2-amino-3-((1S,2S)-2-fluorocyclopropane-1-carbonyl)imidazo[1,2-a]pyridin-6-yl)benzyl)carbamate;
(2-amino-6-(2-(aminomethyl)phenyl)imidazo[1,2-a]pyridin-3-yl)((1S,2S)-2-fluorocyclopropyl)methanone;
(2-amino-6-(2-(2-fluoroethyl)phenyl)imidazo[1,2-a]pyridin-3-yl)((1S,2R)-2-fluorocyclopropyl)methanone;
(2-amino-6-(2-(2-fluoroethyl) phenyl)imidazo[1,2-a]pyridin-3-yl)((1R,2S)-2-fluorocyclopropyl)methanone;
(2-amino-6-(3-fluoro-2-(2-fluoroethoxy)phenyl)imidazo[1,2-a]pyridin-3-yl)((1R,2R)-2-fluorocyclopropyl)methanone;
(2-amino-6-(5-amino-2-methylphenyl)imidazo[1,2-a]pyridin-3-yl)((1S,2S)-2-fluorocyclopropyl)methanone;
(2-amino-6-(2-amino-6-methylphenyl)imidazo[1,2-a]pyridin-3-yl)((1S,2S)-2-fluorocyclopropyl)methanone;
(2-amino-6-(3-fluoro-2-((E)-2-methoxyvinyl)phenyl)imidazo[1,2-a]pyridin-3-yl)((1S,2S)-2-fluorocyclopropyl)methanone;
(2-amino-6-(3-fluoro-2-vinylphenyl)imidazo[1,2-a]pyridin-3-yl)((1S,2S)-2-fluorocyclopropyl)methanone;
(2-amino-6-(5-fluoro-2-methyl-3-(methylamino) phenyl)imidazo[1,2-a]pyridin-3-yl) ((1S,2S)-2-fluorocyclopropyl)methanone;
(2-amino-6-(3-(dimethylamino)-5-fluoro-2-methylphenyl)imidazo[1,2-a]pyridin-3-yl) ((1S,2S)-2-fluorocyclopropyl)methanone;
(2-amino-6-((3-fluoro-2-methylphenyl)amino)imidazo[1,2-a]pyridin-3-yl)((1S,2S)-2-fluorocyclopropyl)methanone;
(2-amino-6-(3-fluoro-2-(2-fluoroethoxy)phenyl)imidazo[1,2-a]pyridin-3-yl)((1S,2R)-2-fluorocyclopropyl)methanone;
(2-amino-6-(5-amino-3-fluoro-2-methylphenyl)imidazo[1,2-a]pyridin-3-yl)((1S,2S)-2-fluorocyclopropyl)methanone; and
(2-amino-6-(3-fluoro-2-methylphen oxy)imidazo[1,2-a]pyridin-3-yl)((1S,2S)-2-fluorocyclopropyl)methanone.

10. The compound of claim 4, wherein $R^3$ is cyclopropyl and $R^6$ is selected from the group consisting of bromo, phenyl, pyridinyl, pyrimidinyl, pyridazinyl, pyrazinyl, aza-indolinyl, indolyl, pyrrolyl, pyrazolyl, imidazolyl, triazolyl, tetrazolyl, thiophenyl, furanyl, oxazolyl, thiazolyl, oxadiazolyl, thiadiazolyl, pyrrolopyridinyl, pyrrolopyrimidinyl, pyrazolopyrimidinyl, imidazolopyridinyl, imidazolopyridinyl, imidazolopyrimidinyl, imidazopyrazinyl, pyrrolotriazinyl, pyrazolopyridinyl, imidazolotriazinyl, purinyl, indazolyl, benzofuranyl, benzothiophenyl, benzooxazolinyl, benzothiazolinyl, benzoimidazolyl, oxoindolinyl, quinolinyl, aza-quinolinyl, isoquinolinyl, aza-isoquinolinyl, quinazolinyl, aza-quinazolinyl, quinoxalinyl, aza-quinoxalinyl, naphthalenyl, wherein $R^6$ is optionally substituted with one or more groups selected from the group consisting of halo, hydroxyl, alkyl, alkenyl, alkynyl, haloalkyl, haloalkoxy, hydroxyalkyl, aminoalkyl, alkylamino, trimethylsilylethoxymethyl, morpholinyl, piperazinyl, methylpiperazinyl, and alkoxyalkenyl.

11. The compound of claim 10, which is selected from the group consisting of:
(2-amino-6-bromoimidazo[1,2-a]pyridin-3-yl)(cyclopropyl)methanone;
(2-amino-6-(4-methylpyridin-3-yl)imidazo[1,2-a]pyridin-3-yl)(cyclopropyl)methanone;
(2-amino-6-(5-methyl-1H-indazol-4-yl)imidazo[1,2-a]pyridin-3-yl)(cyclopropyl)methanone; and
(2-amino-6-(3-fluoro-2-methylphenyl)imidazo[1,2-a]pyridin-3-yl)(cyclopropyl)methanone.

12. The compound of claim 4, wherein $R^3$ is selected from the group consisting of methyl, isopropyl, butyl, methoxy, pyridinyl, phenyl, cyclobutyl, pyrazolyl, azetidinyl, pyrimidinyl, pyrrolidinyl, cyclopropylamino, and indazolyl, wherein $R^3$ is optionally substituted with one or more groups selected from the group consisting of halo, alkyl, hydroxyalkyl, haloalkyl, and monoalkylaminoalkyl.

13. The compound of claim 12, which is selected from the group consisting of:
1-(2-amino-6-(3-fluoro-2-methylphenyl)imidazo[1,2-a]pyridin-3-yl)ethan-1-one;
(2-amino-6-(3-fluoro-2-methylphenyl)imidazo[1,2-a]pyridin-3-yl)(pyridin-2-yl)methanone;
(2-amino-6-(3-fluoro-2-methylphenyl)imidazo[1,2-a]pyridin-3-yl)(phenyl)methanone;
(2-amino-6-(3-fluoro-2-methylphenyl)imidazo[1,2-a]pyridin-3-yl)(cyclobutyl)methanone;
(2-amino-6-(3-fluoro-2-methylphenyl)imidazo[1,2-a]pyridin-3-yl)(1-methyl-1H-pyrazol-4-yl)methanone;
1-(2-amino-6-(3-fluoro-2-methylphenyl)imidazo[1,2-a]pyridin-3-yl)-2,2-dimethylpropan-1-one;
1-(2-amino-6-(3-fluoro-2-methylphenyl)imidazo[1,2-a]pyridin-3-yl)pentan-1-one;
tert-butyl 2-(2-amino-6-(3-fluoro-2-methylphenyl)imidazo[1,2-a]pyridine-3-carbonyl)azetidine-1-carboxylate;
(2-amino-6-(3-fluoro-2-methylphenyl)imidazo[1,2-a]pyridin-3-yl)(3,3-difluorocyclobutyl)methanone;
(2-amino-6-(3-fluoro-2-methylphenyl)imidazo[1,2-a]pyridin-3-yl)(azetidin-2-yl)methanone;

tert-butyl 3-(2-amino-6-(3-fluoro-2-methylphenyl)imidazo[1,2-a]pyridine-3-carbonyl)azetidine-1-carboxylate;
(2-amino-6-(3-fluoro-2-methylphenyl)imidazo[1,2-a]pyridin-3-yl)(azetidin-3-yl)methanone;
(2-amino-6-(1H-indol-5-yl)imidazo[1,2-a]pyridin-3-yl)(pyridin-2-yl)methanone;
(2-amino-6-(1H-pyrrolo[2,3-b]pyridin-5-yl)imidazo[1,2-a]pyridin-3-yl)(pyridin-2-yl)methanone;
(2-amino-6-(4-methyl-1H-pyrrolo[2,3-b]pyridin-5-yl)imidazo[1,2-a]pyridin-3-yl)(pyridin-2-yl)methanone;
(2-amino-6-(4-chloro-1H-pyrrolo[2,3-b]pyridin-5-yl)imidazo[1,2-a]pyridin-3-yl)(pyridin-2-yl)methanone;
(2-amino-6-(3-fluoro-2-methylphenyl)imidazo[1,2-a]pyridin-3-yl)(pyrimidin-2-yl)methanone;
(2-amino-6-(3-fluoro-2-methylphenyl)imidazo[1,2-a]pyridin-3-yl)(pyrimidin-4-yl)methanone;
(2-amino-6-(1H-pyrrolo[2,3-b]pyridin-5-yl)imidazo[1,2-a]pyridin-3-yl)(pyrimidin-4-yl)methanone;
(2-amino-6-(1H-pyrrolo[2,3-b]pyridin-5-yl)imidazo[1,2-a]pyridin-3-yl)(pyrimidin-2-yl)methanone;
(2-amino-6-(4-methyl-1H-pyrrolo[2,3-b]pyridin-5-yl)imidazo[1,2-a]pyridin-3-yl)(azetidin-3-yl)methanone;
(2-amino-6-(4-chloro-1H-pyrrolo[2,3-b]pyridin-5-yl)imidazo[1,2-a]pyridin-3-yl)(azetidin-3-yl)methanone;
(2-amino-6-(4-methyl-1H-pyrrolo[2,3-b]pyridin-5-yl)imidazo[1,2-a]pyridin-3-yl)(pyrimidin-4-yl)methanone;
(2-amino-6-(4-methyl-1H-pyrrolo[2,3-b]pyridin-5-yl)imidazo[1,2-a]pyridin-3-yl)(pyrimidin-2-yl)methanone;
(2-amino-6-(1H-pyrrolo[2,3-b]pyridin-5-yl)imidazo[1,2-a]pyridin-3-yl)(azetidin-3-yl)methanone;
(2-amino-6-(1H-pyrrolo[2,3-b]pyridin-5-yl)imidazo[1,2-a]pyridin-3-yl)(pyrrolidin-3-yl)methanone;
(2-amino-6-(4-methyl-1H-pyrrolo[2,3-b]pyridin-5-yl)imidazo[1,2-a]pyridin-3-yl)(pyrrolidin-3-yl)methanone;
(2-amino-6-(4-chloro-1H-pyrrolo[2,3-b]pyridin-5-yl)imidazo[1,2-a]pyridin-3-yl)(pyrrolidin-3-yl)methanone;
2-amino-N-cyclopropyl-6-(3-fluoro-2-methylphenyl)-N-methylimidazo[1,2-a]pyridine-3-carboxamide;
2-amino-N-cyclopropyl-6-(3-fluoro-2-methylphenyl)imidazo[1,2-a]pyridine-3-carboxamide;
N'-acetyl-2-amino-6-(3-fluoro-2-methylphenyl)imidazo[1,2-a]pyridine-3-carbohydrazide;
methyl 2-amino-6-(3-fluoro-2-methylphenyl)imidazo[1,2-a]pyridine-3-carboxylate;
2-amino-6-(5-chloro-7-(dimethylamino)-6-fluoro-1H-indazol-4-yl)-N-cyclopropylimidazo[1,2-a]pyridine-3-carboxamide; and
(3S,4R)-4-methyltetrahydrofuran-3-yl 2-amino-6-(5-chloro-6-fluoro-7-(methylthio)-1H-indazol-4-yl)imidazo[1,2-a]pyridine-3-carboxylate.

14. A compound of Formula (I):

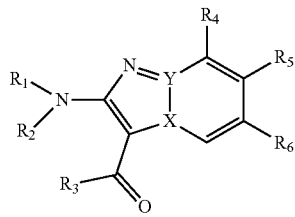

Formula I or a pharmaceutically acceptable salt thereof, wherein:
$R^1$ and $R^2$ are independently —H, $C_1$-$C_6$ alkyl, $C_3$-$C_6$ carbocyclyl, $C_1$-$C_4$ alkanoyl, —(CO) $C_3$-$C_6$ carbocyclyl, aryl, or heteroaryl, wherein each $R^1$ and $R^2$ is optionally substituted with one or more groups selected from the group consisting of halo, alkyl, hydroxyalkyl, haloalkyl, and monoalkylaminoalkyl; or $R^1$ and $R^2$ together form a 5-member heterocycle;
$R^3$ is —H, alkyl, cycloalkyl, heterocyclyl, aryl, heteroaryl, —O-cycloalkyl, —O— heterocyclyl, —O-aryl, —O-heteroaryl, —$NR_c$-alkyl, —$NR_c$-cycloalkyl, —$NR_c$-heterocyclyl, —$NR_c$-aryl, —$NR_c$-heteroaryl, —$NR_c$—$NR_c$ C(=O)$R_c$ or —$CF_3$, wherein $R^3$ is optionally substituted with one or more groups selected from the group consisting of halo, alkyl, hydroxyalkyl, haloalkyl, and monoalkylaminoalkyl;
$R^4$ and $R^5$ are independently —H, —OH, halo, $C_1$-$C_6$ alkyl, $C_1$-$C_6$ alkoxy, aryl, heteroaryl, heterocyclyl, heteroalkyl, amino, —$SCH_3$, or —CN;
$R^6$ is selected from the group consisting of —H, halo, $C_1$-$C_6$ alkyl, $C_1$-$C_6$ alkoxy, $C_3$-$C_6$ carbocyclyl, heterocyclyl, aryl, heteroaryl, —$NR_c$-aryl, —$NR_c$-heteroaryl, —O-aryl, —O-heteroaryl, wherein $R^6$ is optionally substituted with one or more groups selected from the group consisting of halo, hydroxyl, alkyl, alkenyl, alkynyl, haloalkyl, hydroxyalkyl, aminoalkyl, trimethylsilylethoxymethyl, morpholinyl, piperazinyl, methylpiperazinyl, alkoxyalkenyl, —$NO_2$, —$NR_aR_b$, —$NR_aC(=O)R_b$, —$NR_aC(=O)NR_aR_b$, —$NR_aC(=O)OR_b$, —$OR_a$, —$SR_a$, —CN, —$C(=O)R_a$, —$C(=O)OR_a$, —$C(=O)NR_aR_b$, —$OC(=O)R_a$, —$OC(=O)OR_a$, and —$OC(=O)NR_aR_b$;
$R_a$ and $R_b$ are independently —H, halo, amino, alkyl, or haloalkyl;
$R_c$ is —H, $C_1$-$C_3$ alkyl, or cyclopropyl;
X is C; and
Y is N,
wherein $R^4$, $R^5$, and $R^6$ are not each —H.

15. The compound of claim 14, which is
(2-amino-5-(1H-indol-4-yl)pyrazolo[1,5-a]pyridin-3-yl)(cyclopropyl)methanone;
(2-amino-5-(6-fluoro-5-methyl-1H-indazol-4-yl)pyrazolo[1,5-a]pyridin-3-yl)(cyclopropyl)methanone; and
(2-amino-5-(3-fluoro-2-methylphenyl)pyrazolo[1,5-a]pyridin-3-yl)(cyclopropyl)methanone.

16. The compound of claim 1, wherein $R^1$ and $R^2$ are independently —H, alkyl, acetyl, tert-butoxycarbonyl, aminoethyl, dimethylaminoethyl, or methylaminoethyl; or $R^1$ and $R^2$ together form a 5-member heterocycle.

17. The compound of claim 16, which is selected from the group consisting of:
(2-((2-(dimethylamino)ethyl)amino)-6-(3-fluoro-2-methylphenyl)imidazo[1,2-a]pyridin-3-yl)((1S,2S)-2-fluorocyclopropyl)methanone;
(2-((2-aminoethyl)amino)-6-(3-fluoro-2-methylphenyl)imidazo[1,2-a]pyridin-3-yl)((1S,2S)-2-fluorocyclopropyl)methanone;
N-acetyl-N-(3-acetyl-6-(3-fluoro-2-methylphenyl)imidazo[1,2-a]pyridin-2-yl)acetamide;
(6-(3-fluoro-2-methylphenyl)-2-(methylamino)imidazo[1,2-a]pyridin-3-yl)((1S,2S)-2-fluorocyclopropyl)methanone;
(2-(dimethylamino)-6-(3-fluoro-2-methylphenyl)imidazo[1,2-a]pyridin-3-yl)((1R,2S)-2-fluorocyclopropyl)methanone;

tert-butyl (6-(3-fluoro-2-methylphenyl)-3-((1S,2S)-2-fluorocyclopropane-1-carbonyl)imidazo[1,2-a]pyridin-2-yl)carbamate;

(6-(3-fluoro-2-methylphenyl)-2-(pyrrolidin-1-yl)imidazo[1,2-a]pyridin-3-yl)((1S,2S)-2-fluorocyclopropyl)methanone;

(6-(3-fluoro-2-methylphenyl)-2-((2-(methylamino)ethyl)amino)imidazo[1,2-a]pyridin-3-yl)((1S,2S)-2-fluorocyclopropyl)methanone;

N-(6-(3-fluoro-2-methylphenyl)-3-((1S,2S)-2-fluorocyclopropane-1-carbonyl)imidazo[1,2-a]pyridin-2-yl)acetamido; and N-(3-acetyl-6-(3-fluoro-2-methylphenyl)imidazo[1,2-a]pyridin-2-yl)acetamido.

18. The compound of claim 1, wherein the salt is hydrochloric acid salt, tartaric acid salt, phosphoric acid salt, or maleic acid salt.

19. A pharmaceutical composition comprising a therapeutically effective amount of the compound of claim 1 or a pharmaceutically acceptable salt thereof, and at least one pharmaceutically acceptable carrier.

20. The pharmaceutical composition of claim 19, further comprising one or more active ingredient that is useful to treat a neurodegenerative disease.

21. A method for treating an inflammatory and autoimmune disease in a subject, comprising:
administering to the subject in need thereof a therapeutically effective amount of the compound of claim 1 or a pharmaceutically acceptable salt thereof,
wherein the inflammatory and autoimmune disease is selected from the group consisting of α-synucleinopathy, Parkinson's disease, dementia with Lewy body, multiple system atrophy (MSA), Alzheimer's disease, and amyotrophic lateral sclerosis (ALS).

22. The method of claim 21, wherein the subject is a human.

* * * * *